United States Patent
Jackson

(10) Patent No.: US 11,751,914 B2
(45) Date of Patent: Sep. 12, 2023

(54) SOFT STABILIZATION ASSEMBLIES WITH PRETENSIONED CORDS

(71) Applicant: Roger P. Jackson, Prairie Village, KS (US)

(72) Inventor: Roger P. Jackson, Prairie Village, KS (US)

( * ) Notice: Subject to any disclaimer, the term of this patent is extended or adjusted under 35 U.S.C. 154(b) by 27 days.

(21) Appl. No.: 16/543,235

(22) Filed: Aug. 16, 2019

(65) Prior Publication Data

US 2019/0365427 A1    Dec. 5, 2019

Related U.S. Application Data

(63) Continuation of application No. 13/506,657, filed on May 7, 2012, now Pat. No. 10,383,660, which is a continuation-in-part of application No. 13/385,212, filed on Feb. 8, 2012, now Pat. No. 9,216,041, and a continuation-in-part of application No. 13/136,331, filed on Jul. 28, 2011, now abandoned, and a continuation-in-part of application No. 12/802,849, filed on Jun. 15, 2010, now abandoned, and a continuation-in-part of application No. 12/661,042, filed on Mar. 10, 2010, now abandoned, and a continuation-in-part of application No. 12/584,980, filed on Sep. 15, 2009, now Pat. No. 10,729,469, and a continuation-in-part of application No. 12/148,465, filed on Apr. 18, 2008, now Pat. No. 10,258,382.

(60) Provisional application No. 61/518,421, filed on May 5, 2011, provisional application No. 61/463,037, filed on Feb. 11, 2011, provisional application No. 61/403,915, filed on Sep. 23, 2010, provisional application No. 61/400,504, filed on Jul. 29, 2010, provisional application No. 61/396,390, filed on May 26, 2010, provisional application No. 61/395,752, filed on May 17, 2010, provisional application No. 61/395,564, filed on May 14, 2010, provisional application No. 61/336,911, filed on Jan. 28, 2010, (Continued)

(51) Int. Cl.
*A61B 17/70* (2006.01)

(52) U.S. Cl.
CPC ...... *A61B 17/7035* (2013.01); *A61B 17/7001* (2013.01); *A61B 17/702* (2013.01); *A61B 17/7004* (2013.01); *A61B 17/7005* (2013.01); *A61B 17/7008* (2013.01); *A61B 17/7025* (2013.01); *A61B 17/7032* (2013.01)

(58) Field of Classification Search
CPC .................. A61B 17/70; A61B 17/7019–7031
See application file for complete search history.

(56) References Cited

U.S. PATENT DOCUMENTS

| 5,171,279 A | 12/1992 | Mathews |
| D346,217 S | 4/1994 | Sparker et al. |

(Continued)

OTHER PUBLICATIONS

U.S. Appl. No. 15/918,181, filed Mar. 12, 2018, Jackson.

*Primary Examiner* — Eduardo C Robert
*Assistant Examiner* — Michelle C Eckman
(74) *Attorney, Agent, or Firm* — Polsinelli PC

(57) ABSTRACT

A soft dynamic stabilization assembly includes a core, typically in the form of a tensioned cord, at least one pair of bone anchors, a spacer surrounding the core located between the bone anchors, typically, at least one elastic bumper and at least one fixing or blocking member. The core is slidable with respect to at least one of the bone anchors and cooperating spacer.

20 Claims, 37 Drawing Sheets

Related U.S. Application Data provisional application No. 61/270,754, filed on Jul. 13, 2009, provisional application No. 61/268,708, filed on Jun. 15, 2009, provisional application No. 61/210,058, filed on Mar. 13, 2009, provisional application No. 61/192,312, filed on Sep. 17, 2008, provisional application No. 60/927,111, filed on May 1, 2007.

(56) References Cited

U.S. PATENT DOCUMENTS

| | | |
|---|---|---|
| 5,487,742 A | 1/1996 | Cotrel |
| 5,569,253 A | 10/1996 | Farris et al. |
| 6,132,431 A | 10/2000 | Nilsson et al. |
| 6,248,106 B1 | 6/2001 | Ferree |
| 6,251,112 B1 | 6/2001 | Jackson |
| 6,280,442 B1 | 8/2001 | Barker |
| 6,290,700 B1 | 9/2001 | Schmotzer |
| 6,565,565 B1 | 5/2003 | Yuan et al. |
| 6,997,927 B2 | 2/2006 | Jackson |
| 7,713,288 B2 | 5/2010 | Timm et al. |
| 7,815,665 B2 | 10/2010 | Jahng et al. |
| 7,828,825 B2 | 11/2010 | Bruneau et al. |
| 7,842,072 B2 | 11/2010 | Dawson |
| 7,901,437 B2 | 3/2011 | Jackson |
| 7,988,710 B2 | 8/2011 | Jahng et al. |
| 8,029,544 B2 | 10/2011 | Hested et al. |
| 8,114,133 B2 | 2/2012 | Logan |
| 8,128,667 B2 | 3/2012 | Jackson |
| 8,157,843 B2 | 4/2012 | Biederman et al. |
| 8,292,926 B2 | 10/2012 | Jackson |
| 8,366,745 B2 | 2/2013 | Jackson |
| 8,465,526 B2 | 6/2013 | Friedrich et al. |
| 9,101,404 B2 | 8/2015 | Jackson |
| 9,439,683 B2 | 9/2016 | Jackson |
| 9,451,989 B2 | 9/2016 | Jackson |
| 9,668,771 B2 | 6/2017 | Jackson |
| 9,750,540 B2 | 9/2017 | Jackson |
| 9,861,394 B2 | 1/2018 | Jackson |
| 9,931,139 B2 | 4/2018 | Jackson |
| 9,956,002 B2 | 5/2018 | Jackson |
| 10,130,393 B2 | 11/2018 | Jackson |
| 2002/0035366 A1 | 3/2002 | Walder et al. |
| 2002/0055740 A1 | 5/2002 | Lieberman |
| 2002/0107570 A1 | 8/2002 | Sybert et al. |
| 2002/0116001 A1 | 8/2002 | Schafer |
| 2002/0116065 A1 | 8/2002 | Jackson |
| 2002/0198526 A1 | 12/2002 | Shaolian et al. |
| 2003/0083657 A1 | 5/2003 | Drewry et al. |
| 2003/0212398 A1 | 11/2003 | Jackson |
| 2004/0049190 A1 | 3/2004 | Biederman et al. |
| 2004/0138662 A1 | 7/2004 | Landry et al. |
| 2004/0143265 A1 | 7/2004 | Landry et al. |
| 2004/0167523 A1 | 8/2004 | Jackson |
| 2004/0172032 A1 | 9/2004 | Jackson |
| 2004/0215191 A1 | 10/2004 | Kitchen |
| 2004/0236327 A1 | 11/2004 | Paul et al. |
| 2004/0236328 A1 | 11/2004 | Paul et al. |
| 2005/0010220 A1 | 1/2005 | Casutt et al. |
| 2005/0085815 A1 | 4/2005 | Harms et al. |
| 2005/0131407 A1 | 6/2005 | Sicvol et al. |
| 2005/0149020 A1 | 7/2005 | Jahng |
| 2005/0203514 A1 | 9/2005 | Jahng et al. |
| 2005/0203517 A1 | 9/2005 | Jahng et al. |
| 2005/0261685 A1 | 11/2005 | Fortin |
| 2005/0277919 A1 | 12/2005 | Slivka et al. |
| 2005/0277920 A1 | 12/2005 | Slivka et al. |
| 2005/0277922 A1 | 12/2005 | Trieu et al. |
| 2005/0277932 A1 | 12/2005 | Farris |
| 2005/0288671 A1 | 12/2005 | Yuan et al. |
| 2005/0288672 A1 | 12/2005 | Ferree |
| 2006/0025767 A1 | 2/2006 | Khalili |
| 2006/0036240 A1 | 2/2006 | Colleran et al. |
| 2006/0058788 A1 | 3/2006 | Hammer et al. |
| 2006/0064090 A1 | 3/2006 | Park |
| 2006/0079894 A1 | 4/2006 | Colleran et al. |
| 2006/0142760 A1 | 6/2006 | McDonnell |
| 2006/0149238 A1 | 7/2006 | Sherman et al. |
| 2006/0241602 A1 | 10/2006 | Jackson |
| 2006/0241769 A1 | 10/2006 | Gordon et al. |
| 2006/0247635 A1 | 11/2006 | Gordon et al. |
| 2006/0247779 A1* | 11/2006 | Gordon ............ A61B 17/7052 623/17.15 |
| 2006/0264937 A1 | 11/2006 | White |
| 2007/0005063 A1 | 1/2007 | Bruneau et al. |
| 2007/0032123 A1 | 2/2007 | Timm et al. |
| 2007/0100341 A1 | 5/2007 | Reglos et al. |
| 2007/0118123 A1 | 5/2007 | Strausbaugh et al. |
| 2007/0123864 A1 | 5/2007 | Walder et al. |
| 2007/0129729 A1 | 6/2007 | Petit et al. |
| 2007/0191841 A1 | 8/2007 | Justis et al. |
| 2007/0233064 A1 | 10/2007 | Holt |
| 2007/0233075 A1 | 10/2007 | Dawson |
| 2007/0270821 A1 | 11/2007 | Trieu et al. |
| 2007/0270840 A1 | 11/2007 | Chin et al. |
| 2007/0276380 A1 | 11/2007 | Jahng et al. |
| 2007/0288011 A1 | 12/2007 | Logan |
| 2008/0021469 A1 | 1/2008 | Holt |
| 2008/0051787 A1 | 2/2008 | Remington et al. |
| 2008/0058812 A1 | 3/2008 | Zehnder |
| 2008/0086125 A1 | 4/2008 | Molz et al. |
| 2008/0086130 A1 | 4/2008 | Lake |
| 2008/0161857 A1 | 7/2008 | Hestad et al. |
| 2008/0183213 A1 | 7/2008 | Veldman et al. |
| 2008/0234691 A1 | 9/2008 | Schwab |
| 2008/0234737 A1 | 9/2008 | Boschert |
| 2008/0234744 A1* | 9/2008 | Zylber ............ A61B 17/7031 606/264 |
| 2008/0262551 A1 | 10/2008 | Rice et al. |
| 2008/0262553 A1 | 10/2008 | Hawkins et al. |
| 2008/0275504 A1 | 11/2008 | Bonin et al. |
| 2008/0294198 A1 | 11/2008 | Jackson |
| 2008/0319482 A1 | 12/2008 | Jackson |
| 2008/0319486 A1 | 12/2008 | Hestad et al. |
| 2009/0005817 A1* | 1/2009 | Friedrich ............ A61B 17/7019 606/264 |
| 2009/0012562 A1 | 1/2009 | Hestad et al. |
| 2009/0036924 A1* | 2/2009 | Egli .................. A61B 17/7019 606/264 |
| 2009/0054932 A1 | 2/2009 | Butler et al. |
| 2009/0082815 A1 | 3/2009 | Zylber et al. |
| 2009/0088799 A1 | 4/2009 | Yeh |
| 2009/0093846 A1 | 4/2009 | Hestad |
| 2009/0099606 A1 | 4/2009 | Hestad et al. |
| 2009/0105757 A1 | 4/2009 | Gimbel et al. |
| 2009/0105758 A1 | 4/2009 | Gimbel et al. |
| 2009/0177231 A1 | 7/2009 | Kiester |
| 2009/0198280 A1 | 8/2009 | Spratt et al. |
| 2009/0204152 A1 | 8/2009 | Blain |
| 2009/0228045 A1 | 9/2009 | Hayes et al. |
| 2009/0240285 A1 | 9/2009 | Friedrich et al. |
| 2009/0240286 A1 | 9/2009 | Friedrich et al. |
| 2009/0259257 A1 | 10/2009 | Prevost |
| 2009/0275983 A1 | 11/2009 | Veldman et al. |
| 2009/0299411 A1 | 12/2009 | Laskowitz et al. |
| 2010/0010542 A1 | 1/2010 | Jackson |
| 2010/0010543 A1 | 1/2010 | Jackson |
| 2010/0036423 A1 | 2/2010 | Hayes |
| 2010/0137912 A1 | 6/2010 | Alcock et al. |
| 2010/0174319 A1 | 7/2010 | Jackson |
| 2010/0211105 A1 | 8/2010 | Moumene et al. |
| 2010/0228292 A1 | 9/2010 | Arnold et al. |
| 2010/0331887 A1 | 12/2010 | Jackson et al. |
| 2011/0004222 A1 | 1/2011 | Biedermann et al. |
| 2011/0301644 A1 | 12/2011 | Belliard |
| 2012/0035660 A1 | 2/2012 | Jackson |
| 2012/0053636 A1 | 3/2012 | Schmocker |
| 2012/0221054 A1 | 8/2012 | Jackson |
| 2013/0123853 A1 | 5/2013 | Seme et al. |
| 2013/0197582 A1 | 8/2013 | Prevost et al. |
| 2014/0018857 A1 | 1/2014 | Jackson |
| 2014/0039555 A1 | 2/2014 | Jackson |
| 2014/0121703 A1 | 5/2014 | Jackson |
| 2014/0222076 A1 | 8/2014 | Jackson |

(56) References Cited

U.S. PATENT DOCUMENTS

| | | |
|---|---|---|
| 2014/0343610 A1 | 11/2014 | Jackson |
| 2014/0379030 A1 | 12/2014 | Jackson |
| 2015/0216567 A1 | 8/2015 | Trautwein et al. |
| 2015/0230827 A1 | 8/2015 | Zylber et al. |
| 2015/0320449 A1 | 11/2015 | Jackson |
| 2016/0310169 A1 | 10/2016 | Jackson et al. |
| 2016/0354118 A1 | 12/2016 | Belliard et al. |
| 2017/0100165 A1 | 4/2017 | Jackson |
| 2017/0231662 A1 | 8/2017 | Jackson |
| 2018/0132901 A1 | 5/2018 | Jackson et al. |
| 2018/0168693 A1 | 6/2018 | Jackson et al. |
| 2018/0185068 A1 | 7/2018 | Jackson |
| 2018/0221063 A1 | 8/2018 | Jackson |
| 2018/0243008 A1 | 8/2018 | Jackson |
| 2019/0183534 A1 | 6/2019 | Jackson |
| 2019/0231395 A1 | 8/2019 | Jackson |
| 2019/0239925 A1 | 8/2019 | Jackson |
| 2020/0138482 A1 | 5/2020 | Jackson |
| 2021/0059721 A1 | 3/2021 | Jackson |

\* cited by examiner

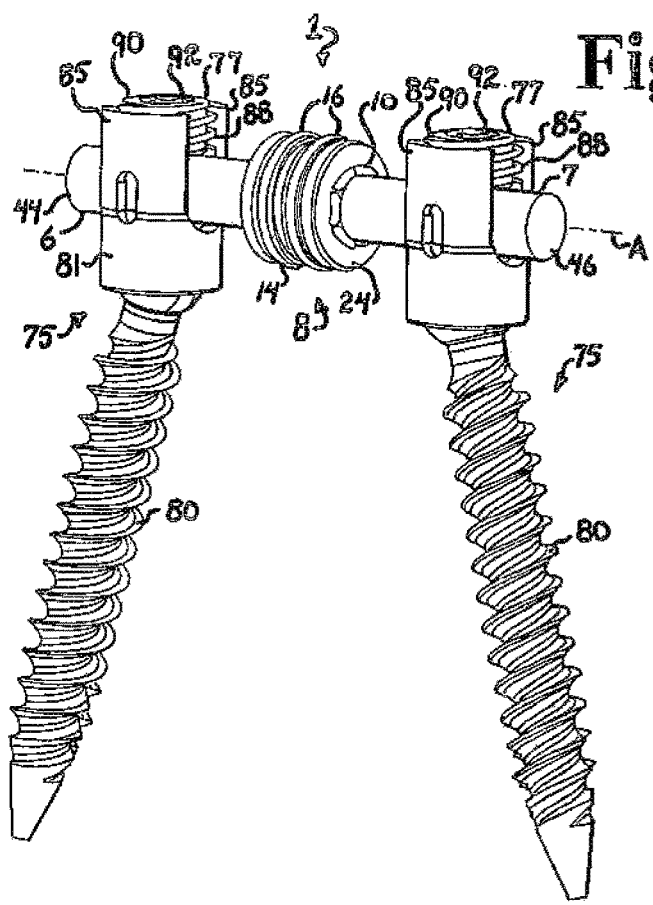
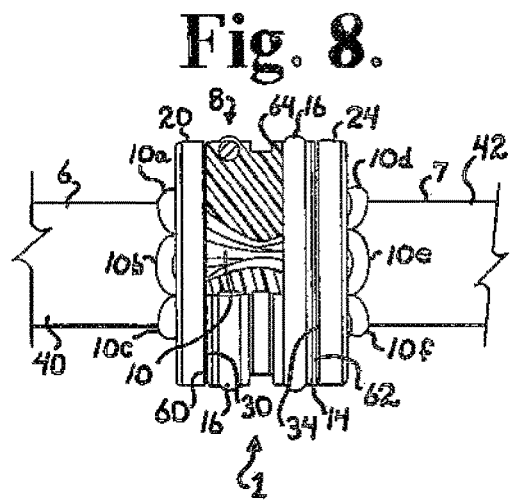
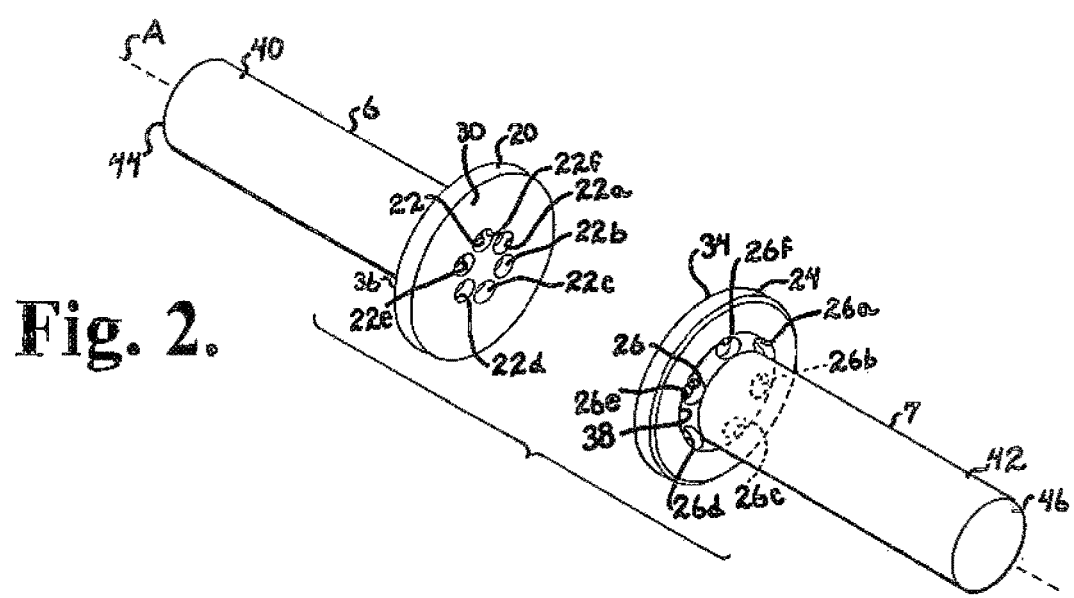

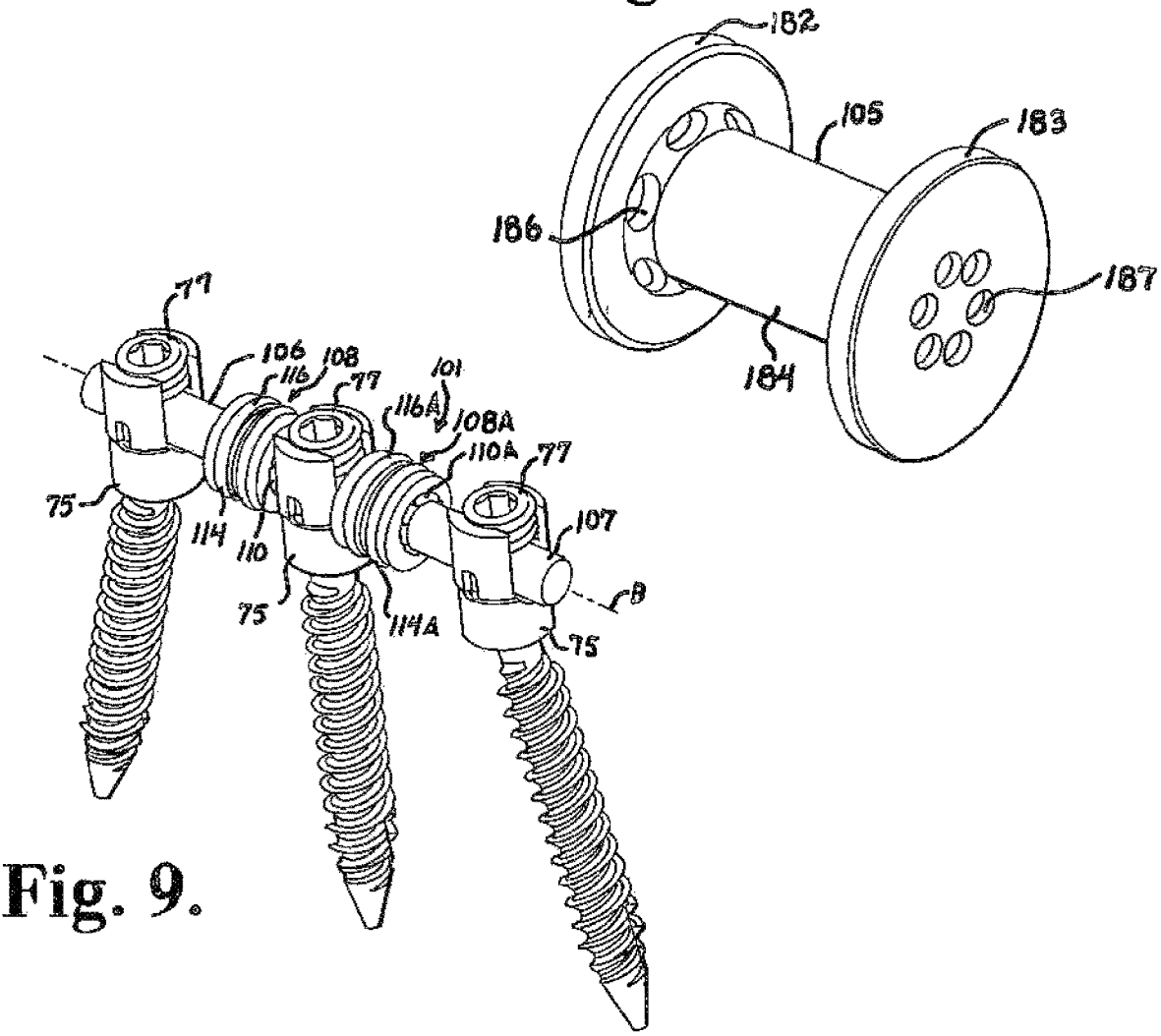
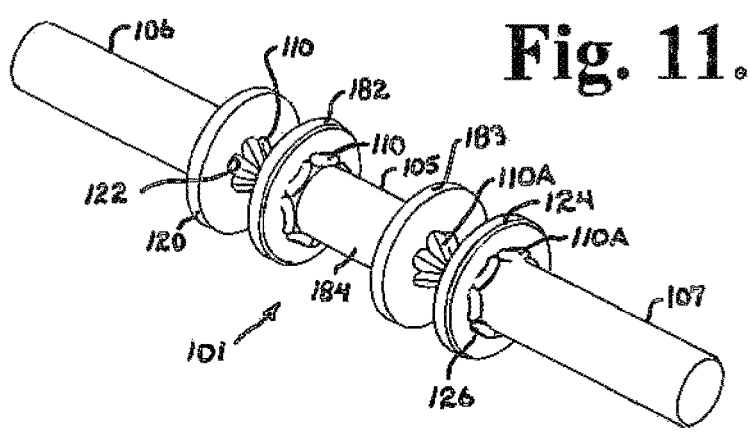

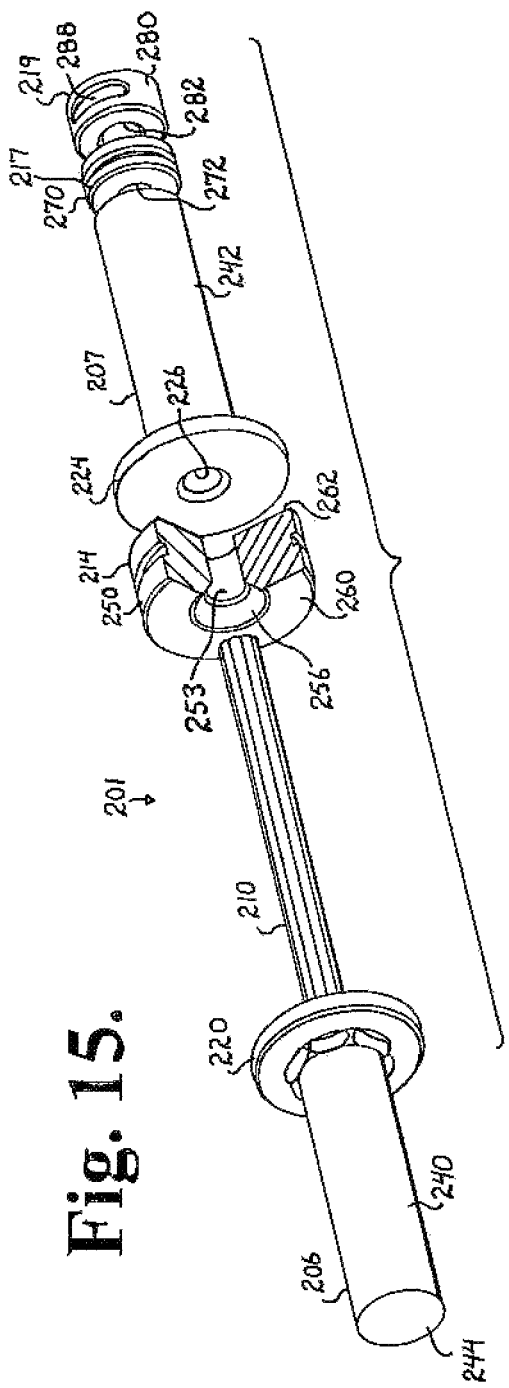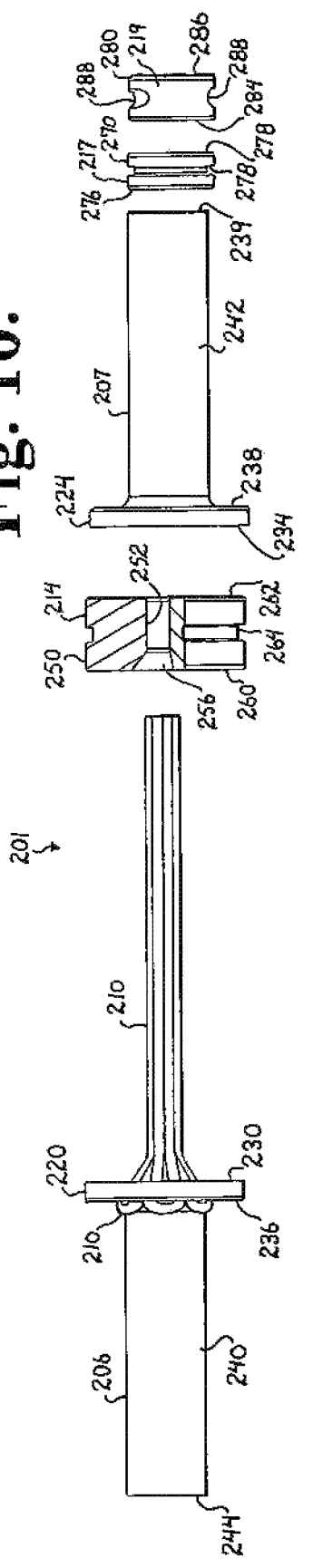

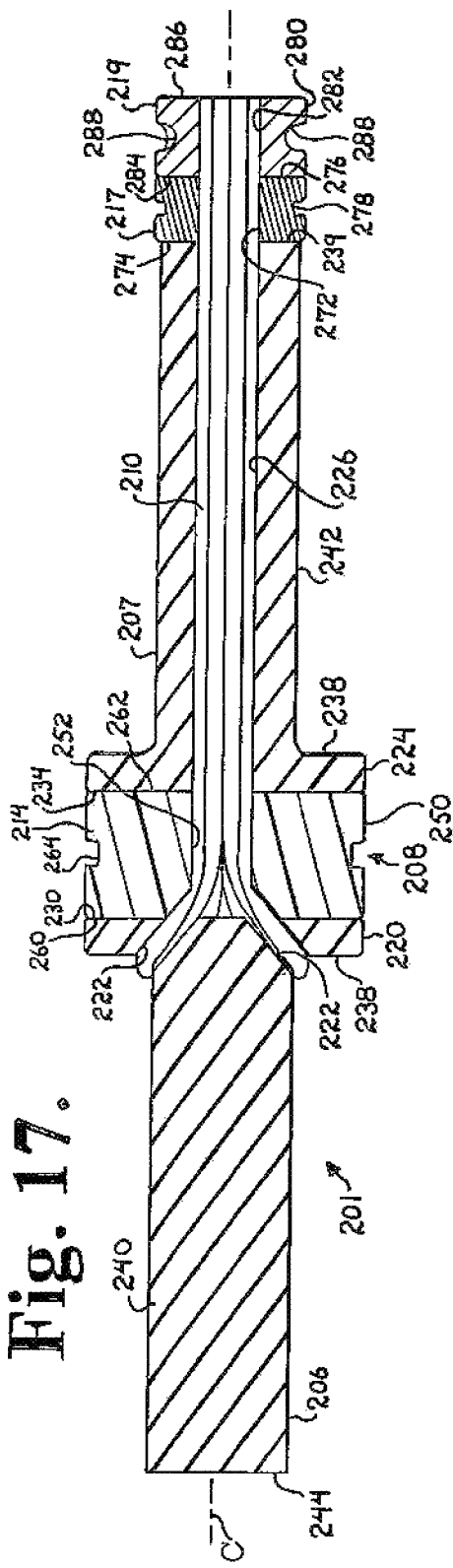
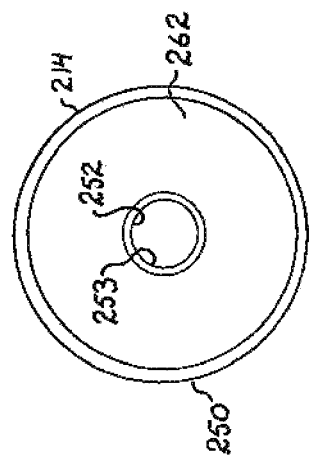
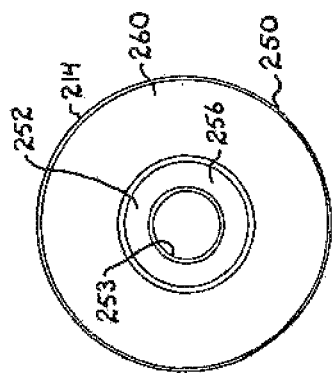

Fig. 20.
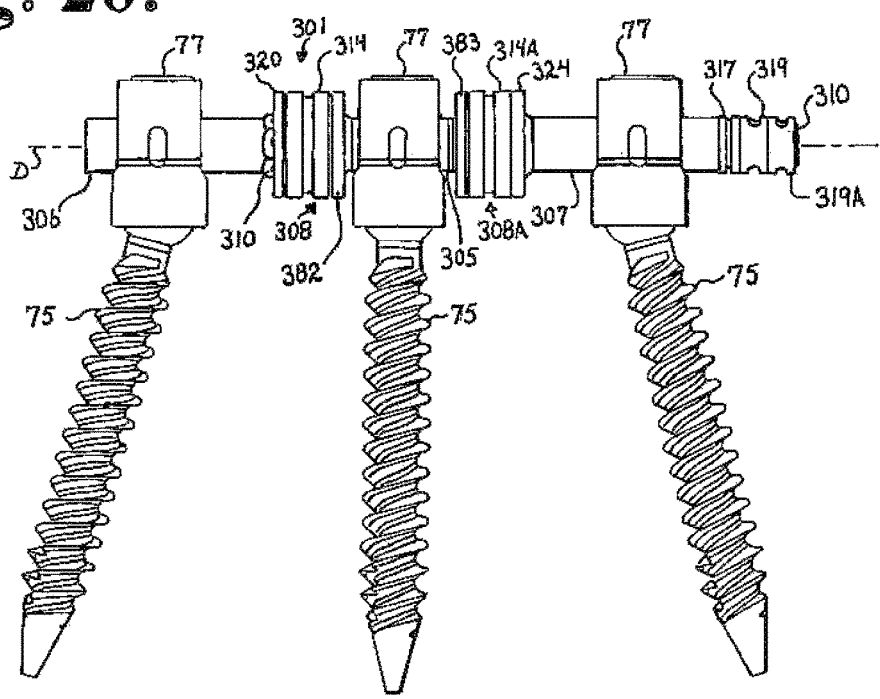
Fig. 21.
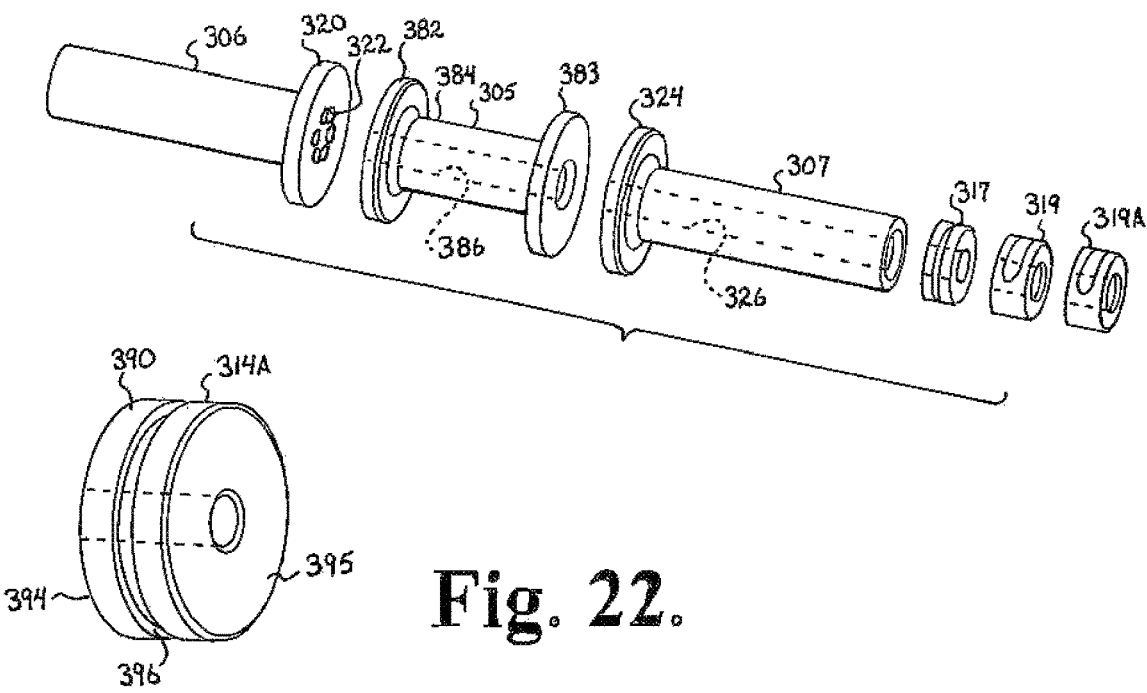
Fig. 22.

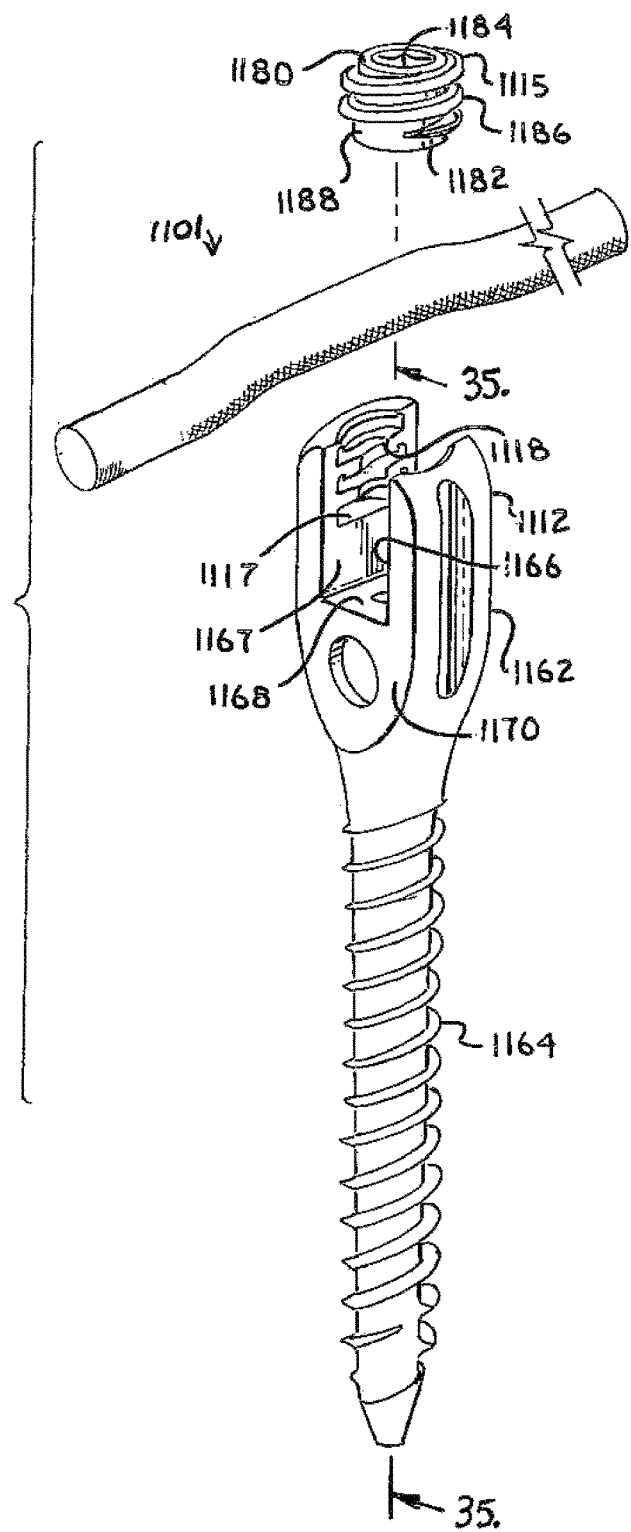
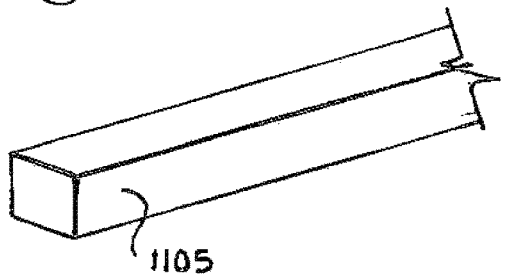
Fig. 33.
Fig. 34.

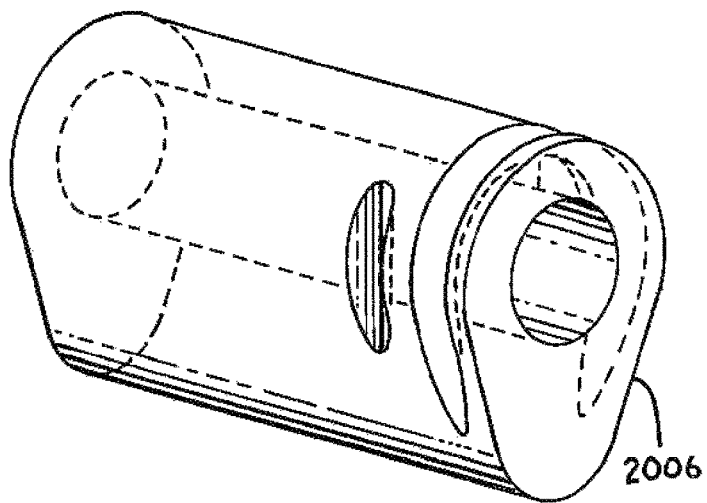
Fig.59.
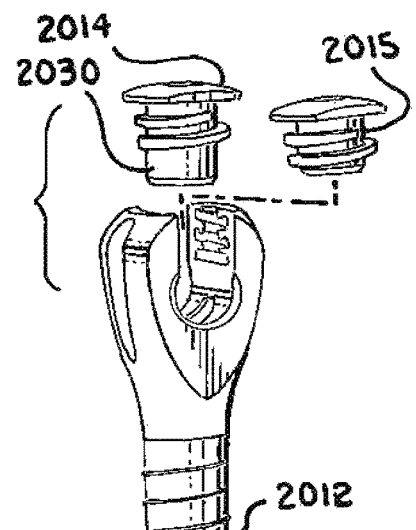
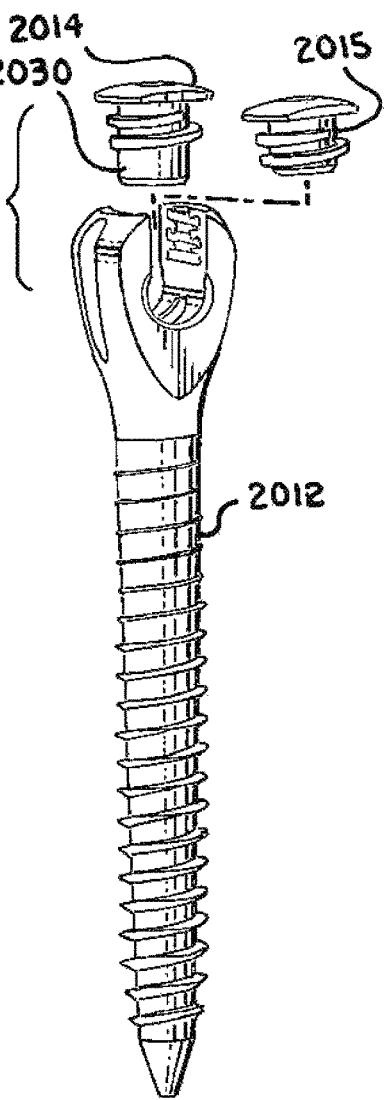
Fig.61.
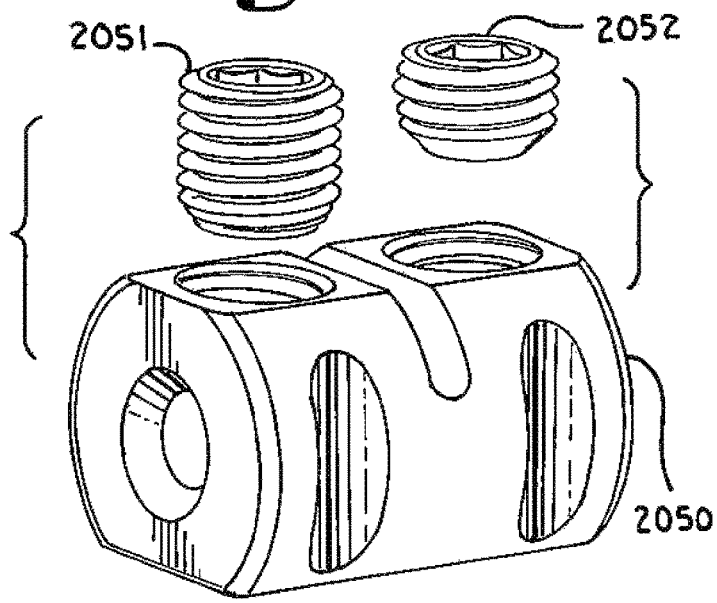
Fig.60.

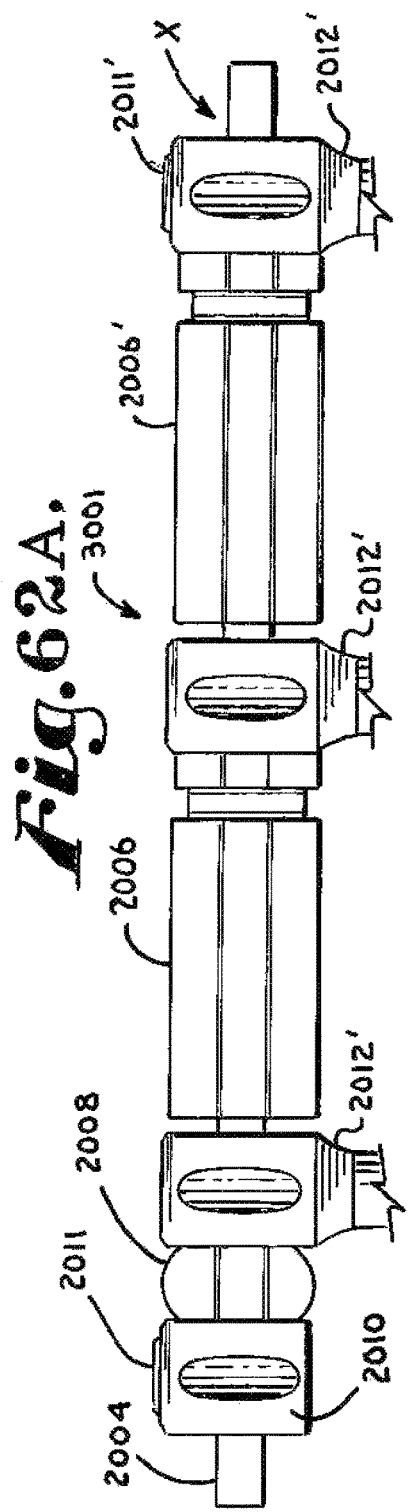
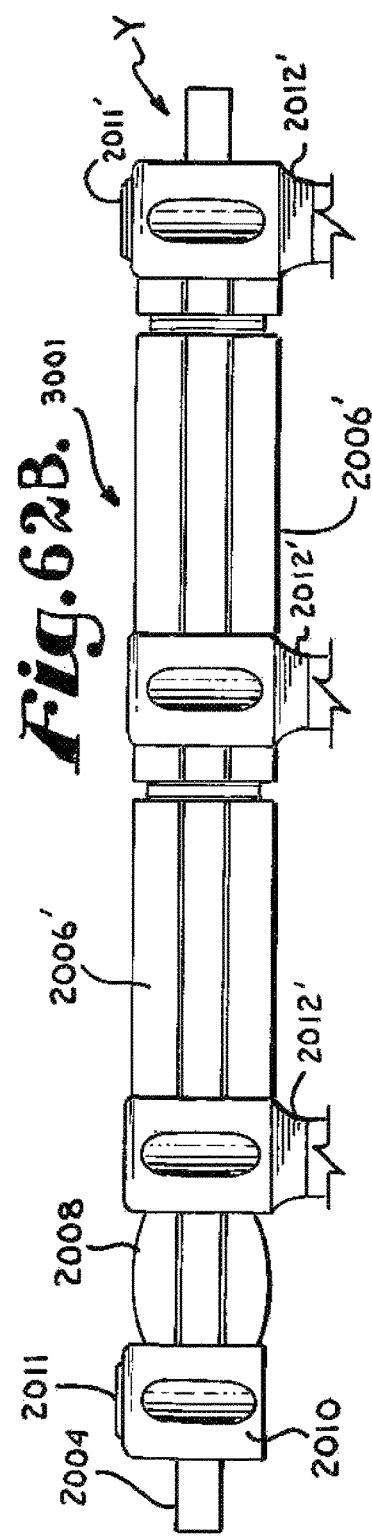
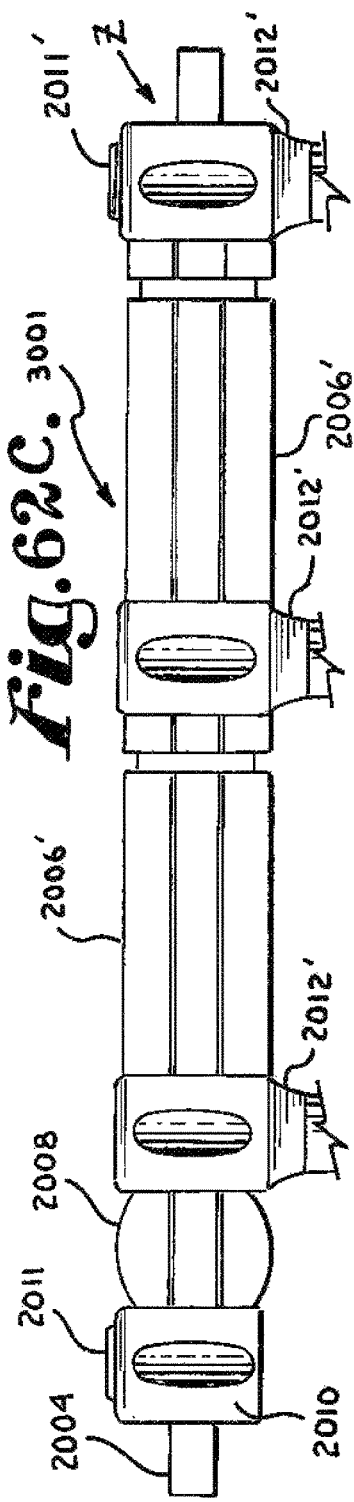

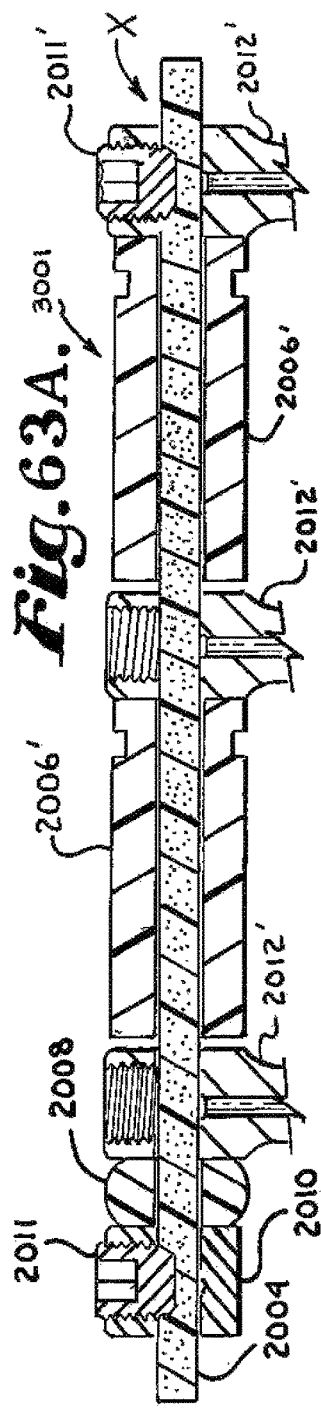
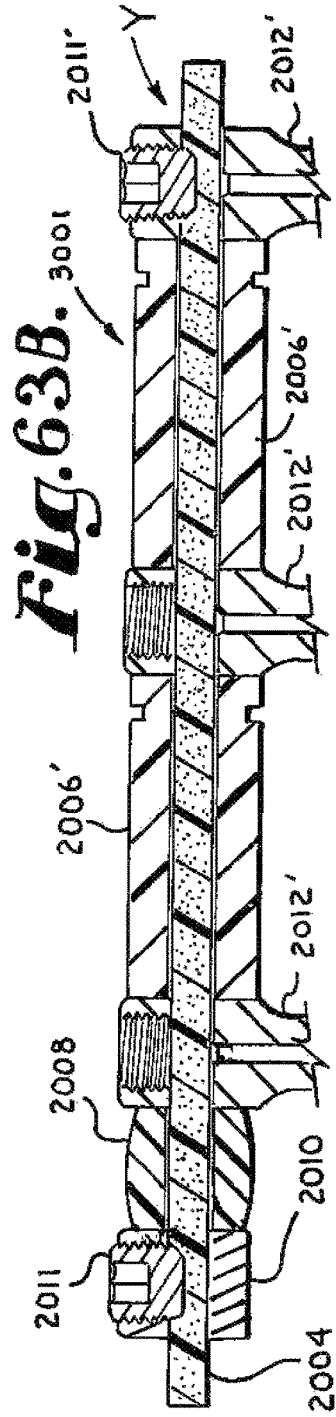
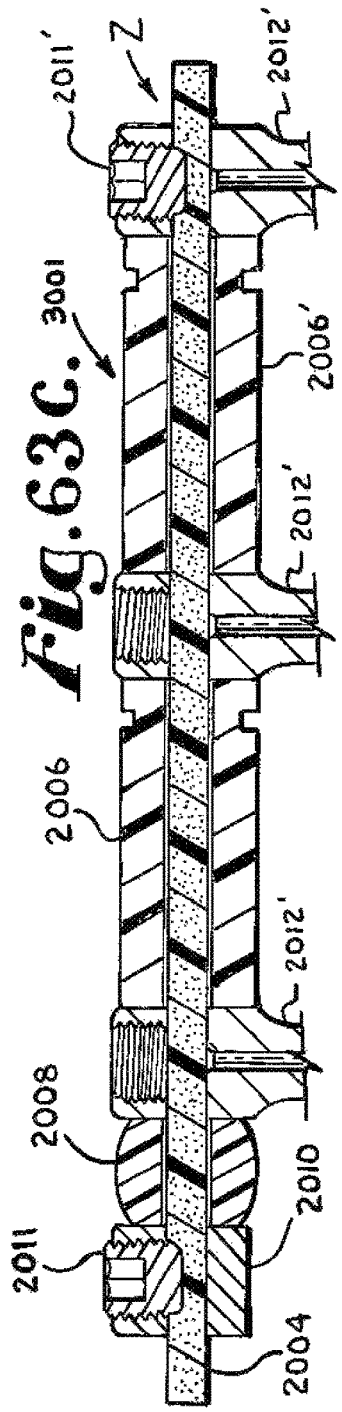

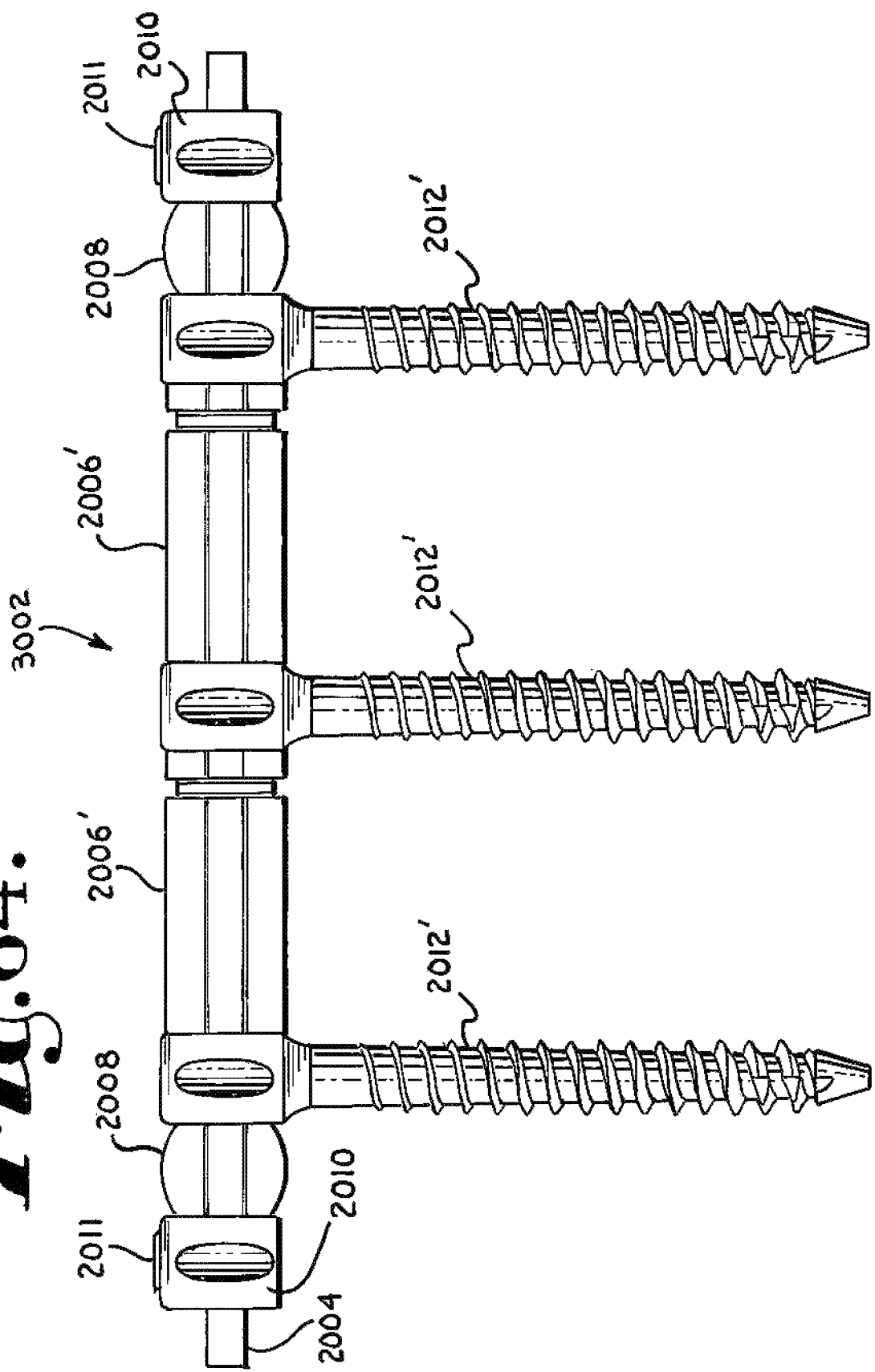

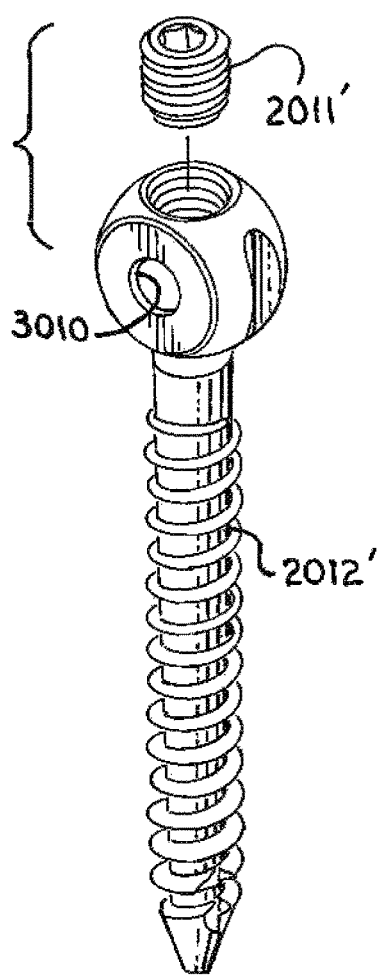
Fig. 69.
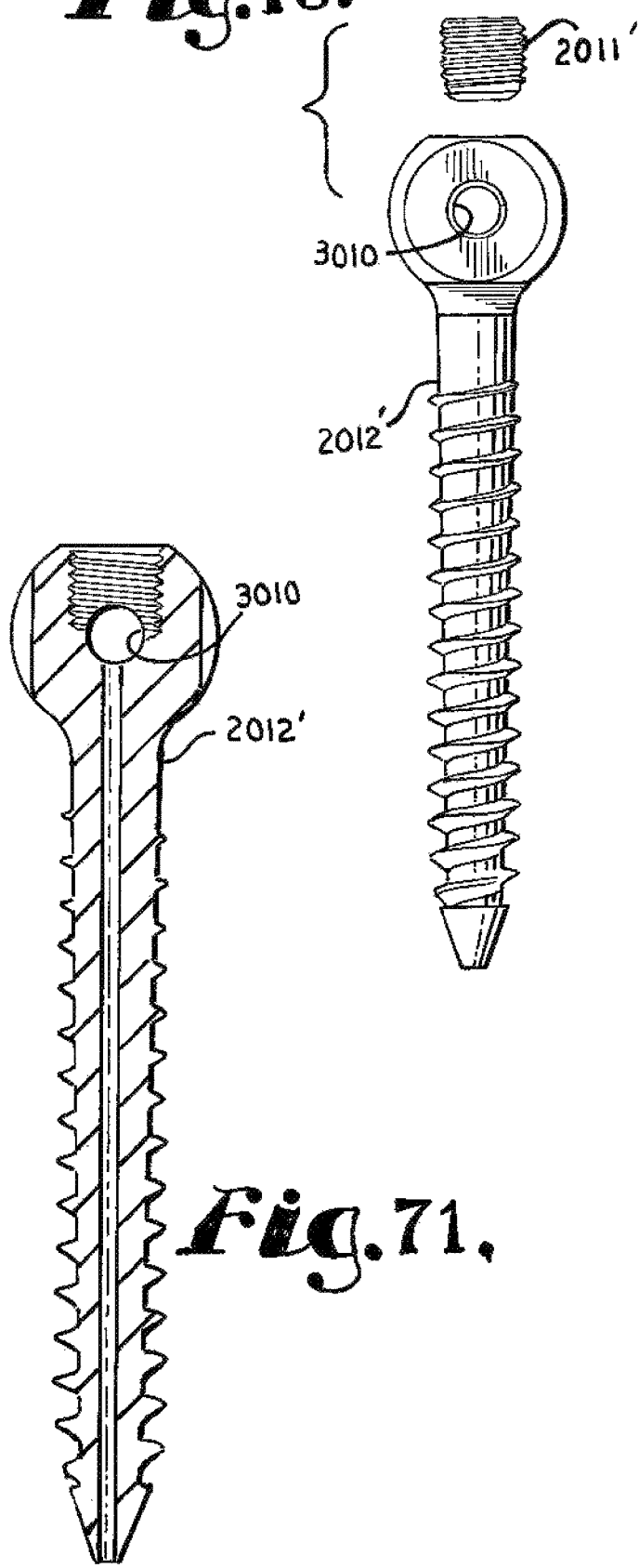
Fig. 70.
Fig. 71.

SOFT STABILIZATION ASSEMBLIES WITH PRETENSIONED CORDS

CROSS-REFERENCE TO RELATED APPLICATIONS

This application is a continuation of U.S. Nonprovisional patent application Ser. No. 13/506,657, filed May 7, 2012, which claims the benefit of U.S. Provisional Patent Application Ser. No. 61/518,421, filed May 5, 2011, both of which are fully incorporated by reference herein for all purposes. U.S. patent application Ser. No. 13/506,657 is also a continuation-in-part of U.S. patent application Ser. No. 13/385,212, filed Feb. 8, 2012, which claims the benefit of U.S. Provisional Patent Application Ser. No. 61/463,037, filed Feb. 11, 2011, both of which are incorporated by reference herein. U.S. patent application Ser. No. 13/506,657 is also a continuation-in-part of U.S. patent application Ser. No. 13/136,331, filed Jul. 28, 2011, which claims the benefit of U.S. Provisional Patent Application Ser. No. 61/400,504, filed Jul. 29, 2010, and 61/403,915, filed Sep. 23, 2010, all of which are incorporated by reference herein. U.S. patent application Ser. No. 13/506,657 is also a continuation-in-part of U.S. patent application Ser. No. 12/802,849, filed Jun. 15, 2010, which claims the benefit of the following U.S. Provisional Patent Application Ser. No. 61/268,708, filed Jun. 15, 2009; 61/270,754, filed Jul. 13, 2009; 61/336,911, filed Jan. 28, 2010; 61/395,564, filed May 14, 2010; 61/395,752, filed May 17, 2010; and 61/396,390, filed May 26, 2010; all of which are incorporated by reference herein. U.S. patent application Ser. No. 13/506,657 is also a continuation-in-part of U.S. patent application Ser. No. 12/148,465, filed Apr. 18, 2008, which claims the benefit of U.S. Provisional Patent Application Ser. No. 60/927,111, filed May 1, 2007, both of which are incorporated by reference herein. U.S. patent application Ser. No. 13/506,657 is also a continuation-in-part of U.S. patent application Ser. No. 12/584,980, filed Sep. 15, 2009, which claims the benefit of U.S. Provisional Patent Application Ser. No. 61/192,312, filed Sep. 17, 2008 and U.S. Provisional Patent Application Ser. No. 61/210,058, filed Mar. 13, 2009, all of which are incorporated by reference herein. U.S. patent application Ser. No. 13/506,657 is also a continuation-in-part of U.S. patent application Ser. No. 12/661,042, filed Mar. 10, 2010, which claims the benefit of U.S. Provisional Patent Application Ser. No. 61/210,058, filed Mar. 13, 2009, all of which are fully incorporated by reference herein for all purposes.

BACKGROUND OF THE INVENTION

The present invention is directed to soft or dynamic fixation assemblies for use in bone surgery, particularly spinal surgery, and in particular to longitudinal connecting members for such assemblies, the connecting members being attached to at least two bone fasteners.

Historically, it has been common to fuse adjacent vertebrae that are placed in fixed relation by the installation therealong of bone screws or other bone anchors and cooperating longitudinal connecting members or other elongate members. Fusion results in the permanent immobilization of one or more of the intervertebral joints. Because the anchoring of bone screws, hooks and other types of anchors directly to a vertebra can result in significant forces being placed on the vertebra, and such forces may ultimately result in the loosening of the bone screw or other anchor from the vertebra, fusion allows for the growth and development of a bone counterpart to the longitudinal connecting member that can maintain the spine in the desired position even if the implants ultimately fail or are removed. Because fusion has been a desired component of spinal stabilization procedures, longitudinal connecting members have been designed that are of a material, size and shape to largely resist flexure, extension, torsion, distraction and compression, and thus substantially immobilize the portion of the spine that is to be fused. Thus, longitudinal connecting members are typically uniform along an entire length thereof, and usually made from a single or integral piece of material having a uniform diameter or width of a size to provide substantially rigid support in all planes.

An alternative to fusion, which immobilizes at least a portion of the spine, and the use of more rigid longitudinal connecting members or other rigid structure has been a "soft" or "dynamic" stabilization approach in which a flexible loop-, S-, C- or U-shaped member or a coil-like and/or a spring-like member is utilized as an elastic longitudinal connecting member fixed between a pair of pedicle screws in an attempt to create, as much as possible, a normal loading pattern between the vertebrae in flexion, extension, distraction, compression, side bending and torsion. Another type of soft or dynamic system known in the art includes bone anchors connected by flexible cords or strands, typically made from a plastic material. Such a cord or strand may be threaded through cannulated spacers that are disposed between adjacent bone anchors when such a cord or strand is implanted, tensioned and attached to the bone anchors. The spacers typically span the distance between bone anchors, providing limits on the bending movement of the cord or strand and thus strengthening and supporting the overall system. Such cord or strand-type systems have typically required specialized bone anchors and tooling for tensioning and holding the cord or strand in the bone anchors.

The complex dynamic conditions associated with spinal movement create challenges for the design of elongate elastic longitudinal connecting members that exhibit an adequate fatigue strength to provide stabilization and protected motion of the spine, without fusion, and that allow for some natural movement of the portion of the spine being reinforced and supported by the elongate elastic or flexible connecting member. A further challenge are situations in which a portion or length of the spine requires a more rigid stabilization, possibly including fusion, while another portion or length may be better supported by a more dynamic system that allows for protective movement.

SUMMARY OF THE INVENTION

Longitudinal connecting member assemblies according to the invention for use between at least two bone anchors provide soft or dynamic, protected motion of the spine and may be extended to provide additional soft or dynamic sections or more rigid support along an adjacent length of the spine, with fusion, if desired. A longitudinal connecting member assembly according to the invention has an inner segment or core typically made from a cord or cords, the core being fixed at either end to substantially rigid segments or structures, including but not limited to rods, tubes, sleeves, blocking structures or stops. The core is typically surrounded by a spacer that is usually elastomeric but may be hard and rigid. Furthermore elastomeric bumpers may be used at locations along the connector to provide a continuous axial load. The longitudinal connecting member assembly is typically dynamically loaded prior to being operatively attached to at least a pair of bone anchors along a patient's spine. The tensioned inner core or cord and one or more compressed spacers or bumpers cooperate dynamically, such features also having some flexibility in bending, with the outer spacer protecting and limiting flexing movement of the inner core. The spacer may include one or more grooves or other features to aid in compression upon installation between the rigid elongate segments.

The illustrated inner core cords of the invention are slidable with respect to illustrated sleeves that are attached to the bone anchor. However, such cords may also may be utilized in sleeveless embodiments wherein the cord is slidable with respect to one or more bone anchor with the cord being fixed to blockers located outside of such an anchor. Thus, also, a dynamic stabilization assembly according to the invention for attachment to at least two bone anchors includes an elongate inner core, preferably a tensioned cord, with at least one spacer, typically in the form of an elastic spacer, surrounding the core, the core and spacer disposed between the at least two bone anchors. One or more elastic bumpers and one or more fixing structures or blockers are disposed on opposite sides of one of the bone anchors, (and/or between certain bone anchors) the bumper or bumpers in compression by cooperation between one or more of the bone anchors and the blocker.

In a method of one aspect of the invention, a cord and surrounding spacer are inserted between first and second implanted bone anchors with a spacer being in contact with both of the bone anchors. The cord is fixed to the first bone anchor or to a blocker located outside the bone anchor. A bumper and a fixing structure or blocker are threaded along the cord until the bumper abuts the second bone anchor and the blocker abuts the bumper. The cord is tensioned and the blocker is crimped or otherwise fixed to the cord, for example, using a set screw, resulting in a tensioned cord with both the bumper and the spacer being in compression. The cord remains in sliding engagement with the second bone anchor, or with both the first and second bone anchors when there are two blockers, advantageously allowing for some elastic distraction of the system with elongation between the screw heads once implanted, as well as compression and bending in response to spinal flexion and extension. In some embodiments according to the invention, there is no overlap between bumpers and blockers while in others, there is some overlap. In some embodiments, blockers may be utilized without bumpers. Soft stabilization assemblies according to the invention may be utilized with both open and closed monoaxial bone screws as well as polyaxial bone screws. In some embodiments, the core cord member may be replaced by relatively hard stiff rods or bars or relatively soft, deformable or non elastic rods or bars, or other longitudinal connecting members of different shapes and materials, including PEEK and other polymers and metal cables. Assemblies of the invention may include mono- and polyaxial open and closed screws that may be used with a first locking fastener or closure top that fixes against the core member (cord, cable, rod or bar), or alternatively with a second locking limited travel closure top that is fixed to the bone screw and captures the core (cord, cable, rod or bar) in the screw, but allows such core member to be in sliding engagement with the bone screw. In the case of a polyaxial screw, the polyaxial mechanism is configured to be locked by this second closure top while allowing the core to travel through the screw head. Such polyaxial screws may include inserts that cooperate directly with closure tops to press down upon the bone screw shank and lock the polyaxial mechanism without pressing on the inner core member. Open bone screws with no set screw may also be utilized.

A variety of embodiments according to the invention are possible. Rods or other substantially rigid structures having different measures of rigidity may be connected according to embodiments of the invention. Either rigid lengths or flexible cords may be of greater or lesser lengths for attaching to one or a plurality of bone anchors.

It is an object of the invention to provide a lightweight, reduced volume, low profile assembly including at least two bone anchors and a soft (or soft and hard combination) longitudinal connecting member therebetween. Furthermore, it is an object of the invention to provide apparatus and methods that are easy to use and especially adapted for the intended use thereof and wherein the apparatus are comparatively inexpensive to make and suitable for use.

Other objects and advantages of this invention will become apparent from the following description taken in conjunction with the accompanying drawings wherein are set forth, by way of illustration and example, certain embodiments of this invention.

The drawings constitute a part of this specification and include exemplary embodiments of the present invention and illustrate various objects and features thereof.

BRIEF DESCRIPTION OF THE DRAWINGS

FIG. 1 is a perspective view of a dynamic fixation longitudinal connecting member according to the invention including first and second rigid rod portions, an inner core, an outer spacer and a pair of support rings, and shown attached to a pair of polyaxial bone screws.

FIG. 2 is an enlarged exploded perspective view of the rigid rod portions of the connecting member of FIG. 1.

FIG. 8 is an enlarged and partial front elevational view of the connecting member of FIG. 1 with portions broken away to show the detail thereof.

FIG. 9 is a perspective view of a second embodiment of a dynamic fixation longitudinal connecting member according to the invention shown with three bone screws.

FIG. 10 is an enlarged perspective view of a rigid rod portion of the connecting member of FIG. 9.

FIG. 11 is an enlarged perspective view of three rigid rod portions and connecting inner core ties of the connecting member of FIG. 9.

FIG. 15 is an enlarged exploded perspective view of the connecting member of FIG. 12, the spacer having a portion broken away to show the detail thereof.

FIG. 16 is an enlarged exploded front elevational view of the connecting member of FIG. 12, the spacer having a portion broken away to show the detail thereof.

FIG. 17 is an enlarged front elevational view of the connecting member of FIG. 12 with portions broken away to show the detail thereof.

FIG. 18 is an enlarged side elevational view of the spacer shown in FIG. 12.

FIG. 19 is an opposed side elevational view of the spacer of FIG. 18.

FIG. 20 is a front elevational view of a fourth embodiment of a dynamic fixation longitudinal connecting member according to the invention shown with three bone screws.

FIG. 21 is an enlarged exploded perspective view of rigid rod portions, a bumper and a crimping ring of the connecting member of FIG. 20.

FIG. 22 is an enlarged perspective view of one of the spacers of the connecting member of FIG. 20.

FIG. 33 is an exploded perspective view of an alternative bone screw for use with the invention of FIG. 28, shown with a cord and a cord sliding limited travel closure top.

FIG. 34 is a partial perspective view of an alternative bar for use with the bone screw and closure top of FIG. 33.

FIG. 59 is an enlarged perspective view of one of the spacers shown in FIG. 44.

FIG. 60 is a reduced, exploded, perspective view of one of the open bone screws shown in FIG. 44, shown with both a slip and a grip closure top.

FIG. 61 is an enlarged, exploded perspective view of the rod/cord connector and cooperating set screws shown in FIG. 51.

FIG. 62A is a partial and enlarged front elevational view of another soft dynamic stabilization connector of the invention having an inner cord, an elastic bumper and a blocking structure, two spacers and shown, with three closed monoaxial screws, one with a cooperating set screw, the figure shows the connector in a distracted state.

FIG. 62B is a partial and enlarged front elevational view, similar to FIG. 62A, showing the connector of FIG. 62A in a compressed state.

FIG. 62C is a partial and enlarged front elevational view, similar to FIG. 62A, showing the connector of FIG. 62A in a nominal state.

FIG. 63A is a partial front elevational view with portions broken away of the connector of FIG. 62A.

FIG. 63B is a partial front elevational view with portions broken away of the connector of FIG. 62B.

FIG. 63C is a partial front elevational view with portions broken away of the connector of FIG. 62C.

FIG. 64 is a front elevational view of another soft dynamic stabilization connector of the invention having an inner cord, two elastic bumpers, two blocking structures, two spacers and shown with three closed monoaxial screws with no set screws.

FIG. 69 is a reduced, exploded, perspective view of the closed bone screw and cooperating set screw shown in FIGS. 62A-68.

FIG. 70 is an exploded side elevational view of the bone screw and set screw of FIG. 69.

FIG. 71 is an enlarged side elevational view of the bone screw of FIG. 70 with portions broken away to show the detail thereof.

DETAILED DESCRIPTION OF THE INVENTION

Figure 3:
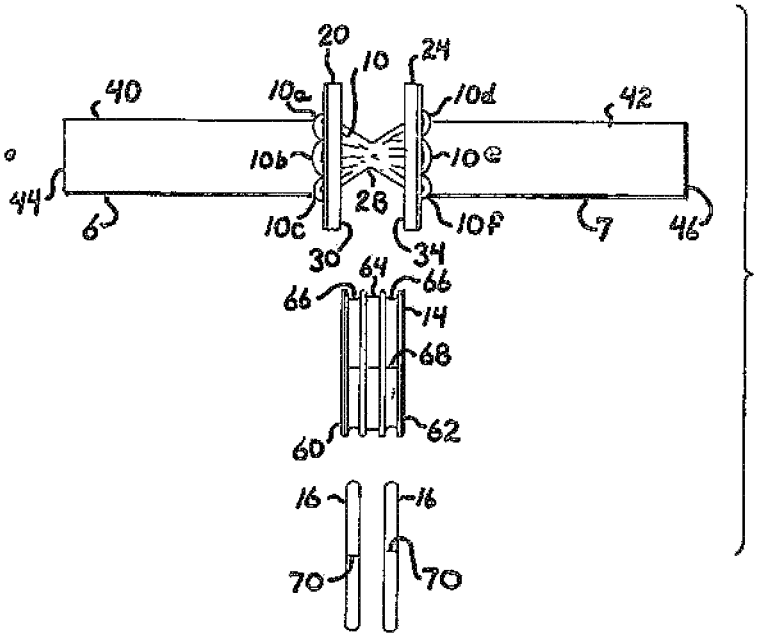
FIG. 3 is an enlarged exploded front elevational view of the connecting member of FIG. 1.
Figure 4:
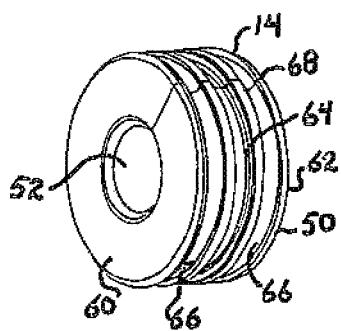
FIG. 4 is an enlarged perspective view of the spacer of FIG. 1.
Figure 5:
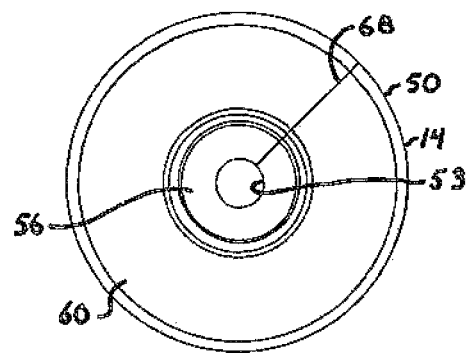
FIG. 5 is an enlarged side elevational view of the spacer of FIG. 1.
Figure 6:
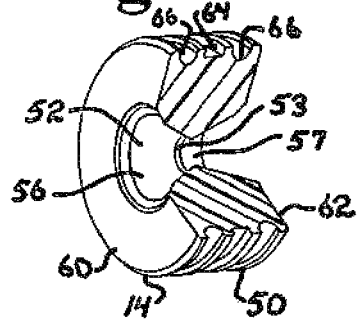
FIG. 6 is an enlarged perspective view of the spacer of FIG. 1 with portions removed to show the detail thereof.

As required, detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure. It is also noted that any reference to the words top, bottom, up and down, and the like, in this application refers to the alignment shown in the various drawings, as well as the normal connotations applied to such devices, and is not intended to restrict positioning of the connecting member assemblies of the application and cooperating bone anchors in actual use.

With reference to FIGS. 1-8, the reference numeral 1 generally designates a non-fusion dynamic stabilization longitudinal connecting member assembly according to the present invention. The connecting member assembly 1 is elongate and substantially cylindrical, having a central axis A. The connecting member assembly 1 generally includes first and second substantially rigid members 6 and 7 with a central, dynamic connection or transition portion or segment, generally 8, disposed therebetween. A tie or a plurality of ties 10 link the rigid members 6 and 7 at the central segment 8. The ties 10 may be any flexible elongate material that fastens, secures or unites the rigid members 6 and 7, including, but not limited to cords, threads, strings, bands, or fibers that may be single or multiple strands, including twisted, braided or plaited materials. The illustrated central segment 8 further includes an outer sleeve or spacer 14 and a pair of support rings 16.

Each of the illustrated rigid members 6 and 7 are substantially cylindrical with one or more circular cross-sections along a length thereof. However, it is foreseen that the members 6 and 7 may have other forms, including but not limited to oval, square and rectangular cross-sections as well as other curved or polygonal shapes. It is foreseen that the member 6 and 7 may be of different materials, different shapes or different sizes, and thus one member may be more rigid or more flexible than the other member. The members 6 and 7 each are of a length for cooperating with at least one and up to a plurality of bone attachment members, such as bone screws or hooks. The member 6 is substantially solid, rigid and cylindrical and further includes a buttress or plate 20 having a plurality of apertures in the form of through bores 22. The member 7 is also substantially solid, rigid and cylindrical and includes a buttress or plate 24 similar or identical to the plate 20. The plate 24 also has a plurality of apertures in the form of through bores 26 running therethrough that are identical or similar to the apertures 22. Each of the bores 22 and 26 extends through the respective plate 20 and 24 at an oblique angle with respect to the axis A. It is foreseen that according to the invention the bores 22 and 26 may also run parallel to the axis A. It is foreseen that the cord, cords, strands or fibers could be embedded into or adhered on the ends of the members 6 and 7.

With particular reference to FIG. 2, in the illustrated embodiment, there is shown six bores 22a, 22b, 22c, 22d, 22e and 22f and six cooperating bores 26a, 26b, 26c, 26d, 26e and 26f, each oriented substantially uniformly about the axis A. With reference to both FIGS. 2 and 3, in the illustrated embodiment, the ties 10 are in the form of six independent closed loops, 10a, 10b, 10c, 10d, 10e and 10f, oriented in a criss-cross pattern, that attach or tether the rigid members 6 and 7 together at the respective plates 20 and 24. The loops are installed individually, with the individual cords 10 being at least one of knotted, adhered, bonded or melted, to form such a closed loop after threading though two adjacent bores in each of the plates 20 and 24. For example, one looped cord 10 extends through the bores 22a and 22b, looping about the plate 20 at a location between the bores 22a and 22b, and also extends through the bores 26d and 26e, looping about the plate 24 at a location between the bores 26d and 26e. While, in similar fashion, another cord 10 loops about the plate 22 by extending through the bores 22d and 22e and also about the plate 24 by extending through the bores 26a and 26b. As illustrated in FIG. 3, orienting the individual loops 10a-10f in such a criss-cross pattern provides a resulting dynamic corded section 8 that slopes or angles inwardly toward the axis A at or near a central location 28 thereof, providing adequate clearance and ready acceptance of the spacer 14 as will be described in greater detail below. It is foreseen that the cords 10 may be individually looped in a configuration substantially parallel to the axis A or a variety of other orientations.

The ties 10 making up the individual or closed loops may be made from a variety of materials, including polyester or other plastic fibers, strands or threads, such as polyethyleneterephthalate. Such cord and cord-like materials usually are placed under axial tension prior to final installation, for example, the loops 10a-10f that are attached to the plates 20 and 24 may be tensioned along the axis A for a selected time prior to installation of the spacer 14 to allow the cords 10 to lengthen and otherwise deform during a primary creep stage. As will be described in more detail below, after the cords 10 reach secondary or steady-state creep, further tension is then placed on the cords 10 in preparation for installation of the spacer 14 between the plates 20 and 24 to ensure dynamic pre-loading of the connector 1, with the corded loops 10a-10f being in tension along the axis A while at the same time the spacer 14 is in compression along the axis A. It is also foreseen that in alternative embodiments of the invention, greater or fewer than six discrete loops or even a single tie 10 may be laced through numerous apertures in the plates 20 and 24 to connect the member 6 to the member 7.

Cords 10 of the invention typically do not illustrate elastic properties, such as any significant additional axial distraction after the assembly 1 is operatively assembled. However, it is foreseen that in some embodiments, the ties or cords 10 may be made of a plastic or rubber (natural or synthetic) having elastic properties, allowing for some further distraction of the central connection portion 8 at the ties 10 during operation thereof.

Returning to the longitudinal connecting member rigid members 6 and 7, each of the plates 20 and 24 include respective outer planar surfaces or faces 30 and 34 that operatively face toward one another. Furthermore, each plate 20 and 24 has a respective opposed face 36 and 38. The bores 22a-f open at both the faces 30 and 36 and the bores 26a-f open at both the faces 34 and 38. As illustrated in FIGS. 3 and 8, the cords 10 that form the six discrete closed loops, contact the faces 36 and 38 and attach the plate 20 to the plate 24 with the substantially planar surfaces 30 and 34 facing each other. Extending from the faces 36 and 38 are respective elongate cylindrical portions 40 and 42 of the rigid members 6 and 7. The portion 40 terminates at an end 44 and the portion 42 terminates at an end 46. The portions 40 and 42 are each sized and shaped to attach to at least one bone anchor as will be described in greater detail below. The illustrated portions 40 and 42 are approximately the same size, but it is foreseen that different sizes, lengths and shapes are possible, as well as making the portions 40 and 42 from different materials and also making the plates 20 and 24 from materials that are different than the portions 40 and 42. In the illustrated embodiment, the plates 20 and 24 are integral with respective elongate portions 40 and 42 with the members 6 and 7 being made from metal, metal alloys or other suitable materials, including plastic polymers such as polyetheretherketone (PEEK), ultra-high-molecular weight-polyethylene (UHMWP), polyurethanes and composites, including composites containing carbon fiber.

With particular reference to FIGS. 3-6 and 8, the sleeve or spacer 14 advantageously cooperates with the cords 10 of the central connection or transition portion 8, providing limitation and protection of movement of the cords 10. The spacer 14 also protects patient body tissue from damage that might otherwise occur in the vicinity of the corded central portion 8. The spacer 14 is substantially cylindrical and made from a plastic, such as a thermoplastic elastomer made from a polyurethane or polyurethane blend. The spacer 14 has an external substantially cylindrical outer surface 50 and an internal surface 52 defining a through bore. The internal surface 52 is further defined by a centrally located surface 53 having a circular cross section and a pair of outwardly extending substantially conical surfaces 56 and 57 running from the surface 53 to respective substantially planar end surfaces 60 and 62. When cooperating with the looped cords 10, the end surfaces 60 and 62 are substantially perpendicular to the axis A and the criss-cross orientation of the looped cords 10 follow the conical inner surfaces 56 and 57 of the spacer 14 with the central portion 28 of the looped cords being substantially aligned with the inner surface 53. It is foreseen that in some embodiments, the spacer may be of circular, square, rectangular or other cross-section including curved or polygonal shapes. In the illustrated embodiment, the spacer 14 further includes a compression groove 64 and a pair of grooves 66 on either side of the groove 64 sized and shaped to receive the support rings or bands 16. Spacers according to the invention may include one, none or any desired number of grooves. The illustrated grooves 64 and 66 are substantially uniform and circular in cross-section, being formed in the external surface 50 and extending radially toward the internal surface 52. The size of the internal surface 52 allows for some axially directed sliding movement of the spacer 14 with respect to the cords 10 of the section 8. The spacer 14 further includes a radially directed elongate slit or gap opening 68 extending therethrough between the outer surface 50 and the inner surface 52 and through the end surfaces 60 and 62. With reference to FIG. 3, the slit or gap 68 allows for opening the spacer 14 and placing the spacer 14 onto the cords 10 of the section 8 with the gap or slit 68 widening or expanding to receive the cords 10 and then elastically returning the spacer 14 to an original cylindrical shape as shown in FIG. 8, but now positioned with the inner cylindrical surface 52 in sliding, rotating engagement with the cords 10 of the section 8. Also, as shown in FIG. 8, when the spacer 14 is initially placed on the cords 10, the spacer 14 completely surrounds the cords 10 and abuts against the buttress plate surfaces 30 and 34. The cords 10 and cooperating compressible spacer 14 allows for some twist or turn, providing some relief for torsional stresses. The spacer 14, however limits such torsional movement as well as bending movement, providing spinal support, as well as allowing for further compression of the assembly 1 at the transition segment 8. It is noted that in addition to limiting the bendability of the central connection portion 8 and thus providing strength and stability to the assembly 1, the spacer 14 also keeps scar tissue from growing into the portion 8 through the cords 10, thus eliminating the need for a sheath-like structure to be placed, adhered or otherwise applied to the cords 10 on the central connection portion 8. In order to reduce the production of any micro wear debris, that in turn may cause inflammation, the spacer 14 inner surfaces and/or cooperating cord 10 surfaces may be coated with an ultra thin, ultra hard, ultra slick and ultra smooth coating, such as may be obtained from ion bonding techniques and/or other gas or chemical treatments.

Figure 7:
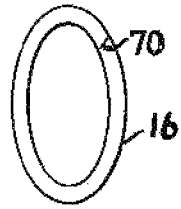
FIG. 7 is an enlarged perspective view of one of the support rings of FIG. 1.

With reference to FIGS. 3 and 7, the support rings or bands 16 are annular and sized and shaped to encircle the spacer 14 and be closely received in the grooves 66. Support rings 16 may be made from a variety of materials, including metals, metal alloys and plastics. A preferred material is tantalum. In the illustrated embodiment, the rings 16 are of circular cross-section and each include a slit or gap 70. The slit or gap 70 allows for opening the ring 16 and placing the ring 16 about the spacer 14 and into one of the grooves 66 with the gap or slit 70 widening or expanding to receive the spacer 14 and then elastically returning the ring 16 to an original circular orientation as shown in FIG. 8, but now positioned about the spacer 14 and within one of the grooves 66. A spot weld, adhesive, or other attachment is then applied to close the slit 70 and secure the ring 16 to itself and about the spacer 14. The pair of rings 16 thus uniformly surround the spacer 14 about the axis A and near each end surface 60 and 62, preventing a gap or gaps from forming at the slit 68. It is foreseen that according to the invention, the support rings or bands may be made of a tough elastic material and therefore not require the slit 70. During installation, the member 6 or 7 would be received by such a band and then the band would be stretched about the spacer 14 and allowed to return to its original form in one of the grooves 66. In a preferred connector 1 of the invention wherein the members 6 and 7 are made from PEEK and cooperate with polyethylene cords 10 and a polyurethane spacer 14, an assembly 1 that is radiolucent results. In such an embodiment, it may be desirable to make the support rings 16 from a metal or metal alloy, such as tantalum, to provide x-ray orientation markers.

The dynamic connecting member assembly 1 cooperates with at least a pair of bone anchors, such as polyaxial bone screws, generally 75, and cooperating closure structures 77 shown in FIG. 1, the assembly 1 being captured and fixed in place at the rigid end portions 40 and 42 by cooperation between the bone screws 75 and the closure structures 77. The dynamic section 8, that is pre-loaded and pre-tensioned, is disposed between the bone screws 75.

It is noted that an advantageous connecting member 1 according to the invention includes a portion 42 made from a metal alloy such as stainless steel that is elongate and intended for fusion along a major portion or section of the spine, for example, the portion 42 may be sized to extend from the sacrum to the thoracic spinal segment T10. Such an elongate portion 42 is thus connectable to a plurality of bone anchors along the spine. Such a connecting member further includes a dynamic section 8, having cords 10 and spacer 14 that is sized for placement, for example, between T9 and T8. Such an embodiment is believed to minimize rapid degeneration and compressive fractures that tend to occur near ends of such elongate connecting member assemblies.

Because the portions 40 and 42 are substantially solid and cylindrical, the connecting member assembly 1 may be used with a wide variety of bone anchors already available for cooperation with rigid rods including fixed, monoaxial bone screws, hinged bone screws, polyaxial bone screws, and bone hooks and the like, with or without compression inserts, that may in turn cooperate with a variety of closure structures having threads, flanges, or other structure for fixing the closure structure to the bone anchor, and may include other features, for example, break-off tops and inner set screws. The bone anchors, closure structures and the connecting member assembly 1 are then operably incorporated in an overall spinal implant system for correcting degenerative conditions, deformities, injuries, or defects to the spinal column of a patient.

The illustrated polyaxial bone screws 75 each include a shank 80 for insertion into a vertebra (not shown), the shank 80 being pivotally attached to an open receiver or head 81. The shank 80 includes a threaded outer surface and may further include a central cannula or through-bore disposed along an axis of rotation of the shank to provide a passage through the shank interior for a length of wire or pin inserted into the vertebra prior to the insertion of the shank 80, the wire or pin providing a guide for insertion of the shank 80 into the vertebra. The receiver 81 has a pair of spaced and generally parallel arms 85 that form an open generally U-shaped channel therebetween that is open at distal ends of the arms 85. The arms 85 each include radially inward or interior surfaces that have a discontinuous guide and advancement structure mateable with cooperating structure on the closure structure 77. The guide and advancement structure may take a variety of forms including a partial helically wound flangeform, a buttress thread, a square thread, a reverse angle thread or other thread like or non-thread like helically wound advancement structure for operably guiding under rotation and advancing the closure structure 77 downward between the receiver arms 85 and having such a nature as to resist splaying of the arms 85 when the closure 77 is advanced into the U-shaped channel. For example, a flange form on the illustrated closure 77 and cooperating structure on the arms 85 is disclosed in Applicant's U.S. Pat. No. 6,726,689, which is incorporated herein by reference.

The shank 80 and the receiver 81 may be attached in a variety of ways. For example, a spline capture connection as described in Applicant's U.S. Pat. No. 6,716,214, and incorporated by reference herein, may be used for the embodiment disclosed herein. Polyaxial bone screws with other types of capture connections may also be used according to the invention, including but not limited to, threaded connections, frictional connections utilizing frusto-conical or polyhedral capture structures, integral top or downloadable shanks, and the like. Also, as indicated above, polyaxial and other bone screws for use with connecting members of the invention may have bone screw shanks that attach directly to the connecting member portion or segment 40 or 42, or may include compression members or inserts that cooperate with the bone screw shank, receiver and closure structure to secure the connecting member assembly 1 to the bone screw and/or fix the bone screw shank at a desired angle with respect to the bone screw receiver that holds the longitudinal connecting member assembly 1. It is foreseen that if the connecting member portions 40 and 42 are fabricated from a plastic such as polyetheretherketone (PEEK), it may be desirable to utilize bone screws that include one or both upper and lower compression inserts that have a saddle or U-shape configuration to closely engage such segments within the bone screw receiver. Although the closure structure 77 of the present invention is illustrated with the polyaxial bone screw 75 having an open receiver or head 81, it is also foreseen that a variety of closure structures may be used in conjunction with any type of medical implant having an open or closed head, including monoaxial bone screws, hinged bone screws, hooks and the like used in spinal surgery.

To provide a biologically active interface with the bone, the threaded shank 80 may be coated, perforated, made porous or otherwise treated. The treatment may include, but is not limited to a plasma spray coating or other type of coating of a metal or, for example, a calcium phosphate; or a roughening, perforation or indentation in the shank surface, such as by sputtering, sand blasting or acid etching, that allows for bony ingrowth or ongrowth. Certain metal coatings act as a scaffold for bone ingrowth. Bio-ceramic calcium phosphate coatings include, but are not limited to: alpha-tri-calcium phosphate and beta-tri-calcium phosphate ($Ca_3(PO_4)_2$), tetra-calcium phosphate ($Ca_4P_2O_9$), amorphous calcium phosphate and hydroxyapatite ($Ca_{10}(PO_4)_6(OH)_2$). Coating with hydroxyapatite, for example, is desirable as hydroxyapatite is chemically similar to bone with respect to mineral content and has been identified as being bioactive and thus not only supportive of bone ingrowth, but actively taking part in bone bonding.

With reference to FIG. 1, the closure structure 77 can be any of a variety of different types of closure structures for use in conjunction with the present invention with suitable mating structure on the interior surface of the upstanding arms 85 of the receiver 81. The illustrated closure structure 77 is rotatable between the spaced arms 85, but could be a slide-in closure structure. As described above, the illustrated closure structure 77 is substantially cylindrical and includes an outer helically wound guide and advancement structure in the form of a flange form 88 that operably joins with the guide and advancement structure disposed on the interior of the arms 85. The illustrated closure structure 77 includes a lower or bottom surface that is substantially planar and may include a point and/or a rim protruding therefrom for engaging the portion 40 or 42 outer cylindrical surface. The closure structure 77 has a top surface 90 with an internal drive feature 92, that may be, for example, a star-shaped drive aperture sold under the trademark TORX. A driving tool (not shown) sized and shaped for engagement with the internal drive feature 92 is used for both rotatable engagement and, if needed, disengagement of the closure 77 from the arms 85. The tool engagement structure 92 may take a variety of forms and may include, but is not limited to, a hex shape or other features or apertures, such as slotted, tri-wing, spanner, two or more apertures of various shapes, and the like. It is also foreseen that the closure structure 77 may alternatively include a break-off head designed to allow such a head to break from a base of the closure at a preselected torque, for example, 70 to 140 inch pounds. Such a closure structure would also include a base having an internal drive to be used for closure removal.

In use, at least two bone screws 75 are implanted into vertebrae for use with the longitudinal connecting member assembly 1. Each vertebra may be pre-drilled to minimize stressing the bone. Furthermore, when a cannulated bone screw shank is utilized, each vertebra will have a guide wire or pin (not shown) inserted therein that is shaped for the bone screw cannula of the bone screw shank 80 and provides a guide for the placement and angle of the shank 80 with respect to the cooperating vertebra. A further tap hole may be made and the shank 80 is then driven into the vertebra by rotation of a driving tool (not shown) that engages a driving feature on or near a top portion of the shank 80. It is foreseen that the screws 75 and the longitudinal connecting member assembly 1 can be inserted in a percutaneous or minimally invasive surgical manner.

With particular reference to FIGS. 2, 3 and 8, the longitudinal connecting member assembly 1 is factory assembled to include the looped ties 10 that are initially tensioned to steady state and thereafter further tensioned to receive the spacer 14 that is cut to a desired size so that the spacer 14 is axially compressed between the plates 20 and 24 after insertion of the spacer 14 about the cords or ties 10 and between such plates 20 and 24. In such process, the spacer 14 is opened or expanded at the slit 68 and moved into position over the cords 10 of the central portion 8 and between the plates 20 and 24 and then allowed to elastically return to an original cylindrical form as shown in FIG. 8. The spacer 14 is also axially compressed during insertion such that the spacer 14 easily slides and is received between the surfaces 30 and 34. Thereafter, the rings or bands 16 are expanded at the respective slits 70 and moved into position in the grooves 66, followed by spot welding thereof to result in closed rings 16 encircling the spacer 14. The resulting connecting member assembly 1 is thus dynamically loaded with the cords 10 in tension and the spacer 14 in compression. In some embodiments according to the invention it may be desirable to place one or more pins through the plates 20 and 24 and into the spacer 14 to prevent rotation of the spacer 14 about the axis A relative to the plates 20 and 24. It may also be desirable to use such pins as x-ray markers.

With further reference to FIG. 1, the pre-loaded connecting member assembly 1 is eventually positioned in an open or percutaneous manner in cooperation with the at least two bone screws 75 with the cords 10 and the spacer 14 disposed between and spaced from the two bone screws 75 and with the portions 40 and 42 each being within a U-shaped channel of a cooperating bone screw 75. It is noted that the portions 40 and/or 42 near respective ends 44 and 46 may be selectively trimmed or cut to size before or at the time of surgery, or if longer, attached to the spine with additional bone anchors. Once a desired position is attained, a closure structure 77 is then inserted into and advanced between the arms 85 of each of the bone screws 75. The closure structure 77 is rotated, using a tool (not shown) engaged with the inner drive 92 until a selected pressure is reached at which point the section 40 or 42 is urged toward, but not completely seated in the U-shaped channel of the bone screw 75. For example, about 80 to about 120 inch pounds pressure may be required for fixing the bone screw shank 80 with respect to the receiver 81 at a desired angle of articulation.

The assembly 1 is thus substantially dynamically loaded and oriented relative to the cooperating vertebra, providing relief (e.g., shock absorption) and protected movement with respect to flexion, extension, distraction and compressive forces placed on the assembly 1 and the two connected bone screws 75. The looped cords 10 and the spacer 14 allow for some twisting or turning, providing some relief for torsional stresses. Furthermore, the compressed spacer 14 places some limits on torsional movement as well as bending movement, to provide spinal support. The pre-loaded cords 10 (in tension) and spacer 14 (in compression) allow for compression and some extension of the assembly 1 located between the two bone screws 75, e.g., shock absorption.

If removal of the assembly 1 from any of the bone screw assemblies 75 is necessary, or if it is desired to release the assembly 1 at a particular location, disassembly is accomplished by using the driving tool (not shown) with a driving formation cooperating with the closure structure 77 internal drive 92 to rotate and remove the closure structure 77 from the receiver 81. Disassembly is then accomplished in reverse order to the procedure described previously herein for assembly.

Eventually, if the spine requires more rigid support, the connecting member assembly 1 according to the invention may be removed and replaced with another longitudinal connecting member, such as a solid rod, having the same diameter as the portions 40 and 42, utilizing the same receivers 81 and the same or similar closure structures 77. Alternatively, if less support is eventually required, a less rigid, more flexible assembly, for example, an assembly 1 having portions 40 and 42 made of a more flexible material, but with the same diameter as the rigid portions 40 and 42, may replace the assembly 1, also utilizing the same bone screws 75.

With reference to FIGS. 9-11, an alternative longitudinal connecting member assembly according to the invention, generally 101, has a central axis B and includes rigid members 105, 106 and 107 and first and second dynamic connection portions or sections 108 and 108A. The dynamic sections 108 and 108A include respective closed looped cords 110 and 110A, respective spacers 114 and 114A and respective support rings 116 and 116A. The connecting member assembly 101 provides for two dynamic support sections between a plurality of vertebrae. The illustrated embodiment is shown attached to three bone screws 75 and cooperating closure structures 77 previously described herein. The illustrated rigid members 105, 106 and 107 are each sized for attachment to a single bone anchor or screw. However, it is noted that each such rigid member 105, 106 and 107 may be of greater length (along the axis B) for operative attachment to two or more bone anchors. Furthermore, more than one rigid member 105 may be disposed between rigid members 106 and 107 to provide a plurality of dynamic sections.

The illustrated members 106 and 107 are identical or substantially similar to respective members 6 and 7 previously described herein with respect to the connecting member 1, the member 106 having an end plate 120 and a plurality of bores 122 similar to the plate 20 and bores 22 previously described herein and the member 107 having an end plate 124 and a plurality of bores 126 similar to the plate 24 and bores 26 previously described herein with respect to the member 7. Also, the closed looped cords 110 and 110A are identical or substantially similar to the closed looped cords 10 previously described herein with respect to the connecting member 1 with the cooperating spacers 114 and 114A being identical or substantially similar to the spacer 14 previously described herein with respect to the connecting member 1. Also, the support rings 116 and 116A are identical or substantially similar to the support rings 16 previously described herein with respect to the connecting member 1. However, in the connecting member 101, rather than having closed looped cords that directly attach the members 106 and 107 as previously described with respect to the members 6 and 7, the closed looped cords 110 attach the member 105 with the member 106 and the closed looped cords 110A attach the member 105 with the member 107 in a manner substantially identical to what has been described herein with respect to the close looped cords 10 of the connecting member 1.

Thus, the member 105 may also be considered to be an extender member that is disposed between the members 106 and 107 and is attached to each of such members with the respective closed looped cords 110 and 110A to provide an additional dynamic segment to the assembly 101. The illustrated member 105 includes a pair of opposed end plates 182 and 183 and an integral cylindrical mid-portion 184 extending therebetween. The end plates 182 and 183 are identical or substantially similar to the plates 20 and 24 previously described herein with respect to the members 6 and 7. Thus, the end plates 182 and 183 include respective apertures or through bores 186 and 187 for receiving the respective closed looped cords 110 and 110A. In the illustrated embodiment there are six bores 186 cooperating with the six bores 122 of the member 6 and six bores 187 for cooperating with the six bores 126 of the member 107. The looped cords 110 loop through the bores 122 and the bores 186 while the looped cords 110A loop through the bores 126 and the bores 187. The illustrated cylindrical mid-portion 184 is sized to be received between arms 85 of at least one bone screw 75.

In use, the closed looped cords 110 and 110A are installed in the same manner as previously described herein with respect to the closed looped cords 10 and the spacers 114 and 114A and cooperating support rings 116 and 116A are installed in the same manner as previously described herein with respect to the spacer 14 and the rings 16. Thereafter, the pre-tensioned, pre-compressed connecting member 101 is positioned in an open or percutaneous manner in cooperation with the at least three bone screws 75 with the cords 110 and 110A and cooperating spacers 114 and 114A each disposed between and spaced from such bone screws 75 and portions of the members 105, 106 and 107 each being within a U-shaped channel of a cooperating bone screw 75. A closure structure 77 is then inserted into and advanced between the arms 85 of each of the bone screws 75 to capture and lock the connecting member 101 in a desired location and position along the spine. Disassembly, removal and replacement of the connecting member assembly 101 with a more or less rigid connecting member may be performed in a manner as previously described herein with respect to the connecting member assembly 1.

With reference to FIGS. 12-19, another alternative longitudinal connecting member assembly according to the invention, generally 201 is elongate and substantially cylindrical, having a central axis C. The connecting member assembly 201 generally includes a first rigid anchor member 206 and a second rigid terminal member 207. A central, dynamic connection or transition portion or segment, generally 208, is disposed between the members 206 and 207. A tie, cord or a plurality of ties or cords 210 loop about and through apertures of the anchor member 206 and extend through a bore in the terminal member 207. The ties 210 may be any flexible elongate material that fastens, secures or unites the rigid members 206 and 207, including, but not limited to cords, threads, strings, bands, or fibers that may be single or multiple strands, including twisted, braided or plaited materials. The illustrated central segment 208 further includes a closed, non-slitted outer sleeve or spacer 214. The assembly 201 further includes an elastic bumper 217 and a crimping ring 219.

Each of the illustrated rigid members 206 and 207 are substantially cylindrical with one or more circular cross-sections along a length thereof. However, it is foreseen that the members 206 and 207 may have other forms, including but not limited to oval, square and rectangular cross-sections as well as other curved or polygonal shapes. It is foreseen that the members 206 and 207 may be of different materials, different shapes or different sizes, and thus one member may be more rigid or more flexible than the other member. The members 206 and 207 each are of a length for cooperating with at least one and up to a plurality of bone attachment members, such as bone screws or hooks.

Figures 12, 13, 14:
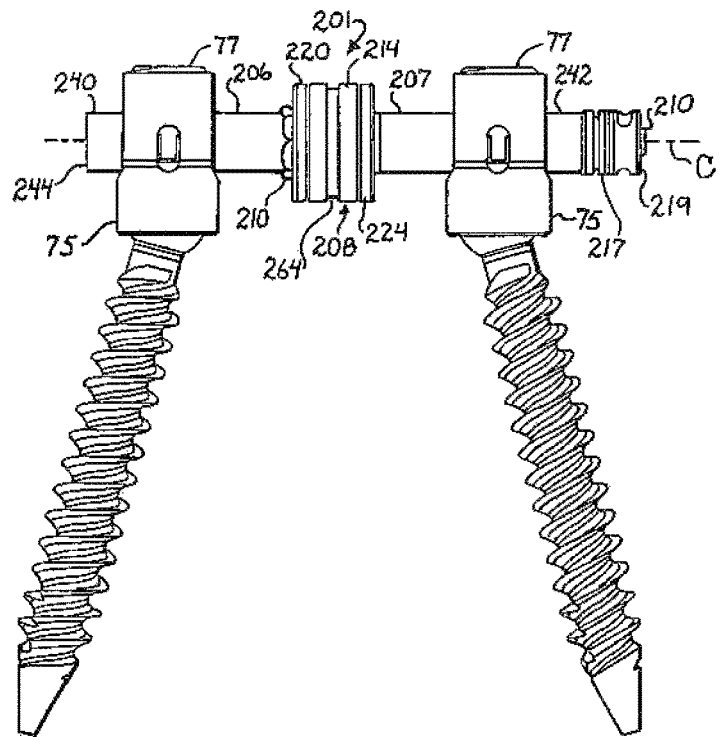
FIG. 12 is a front elevational view of a third embodiment of a dynamic fixation longitudinal connecting member according to the invention including first and second rigid rod portions, an inner core, an outer spacer, an elastic bumper and a crimping ring, and shown attached to a pair of polyaxial bone screws.
FIG. 13 is an enlarged perspective view of the first rigid rod portion of FIG. 12.
FIG. 14 is an enlarged perspective view of the second rigid rod portion of FIG. 12.

With particular reference to FIGS. 12, 13 and 17, the anchor member 206 is substantially solid, rigid and cylindrical and further includes a buttress or plate 220 having a plurality of apertures in the form of through bores 222. The member 206 is identical or substantially similar to the member 6 previously described herein with respect to the connecting member assembly 1. The illustrated anchor member 206 has six bores 222 that extend through the plate 220 at an oblique angle with respect to the axis C as best shown in FIG. 17. It is foreseen that according to the invention the bores 222 may also run parallel to the axis C. The ties or cords 210 are in the form of six independent open loops installed individually by looping through pairs of adjacent bores 222 and then extending outwardly away from the plate 220 as shown in FIGS. 15 and 16. Similar to the cords 10 discussed previously herein, the cords 210 are placed under axial tension along the axis C for a selected time prior to final, fixed installation with the other components 214, 207, 217 and 219 to lengthen and otherwise deform the cords 210 during a primary creep stage. After the cords 210 reach secondary or steady-state creep, further tension is then placed on the cords 210 in preparation for final tightening and crimping of the ring 219 as will be described in greater detail below. It is also foreseen that in alternative embodiments of the invention, greater or fewer than six discrete open loops may be laced through apertures in the plate 220 and pulled through the member 207.

The cords 210 of the invention typically do not illustrate elastic properties, such as any significant additional axial distraction after the assembly 201 is operatively assembled. However, it is foreseen that in some embodiments, the ties or cords 210 may be made of a plastic or rubber (natural or synthetic) having elastic properties, allowing for some further distraction of the central connection portion 208 at the ties 210 during operation thereof.

With particular reference to FIG. 14, the terminal member 207 includes a buttress or plate 224 and in inner surface 226 that forms a through bore extending through the entire member 207 in an axial direction, sized and shaped for receiving a length of the bundled cords 210. When operatively connected to the member 206, the bore formed by the inner surface 226 extends along the axis C. With further reference to FIGS. 15-17, each of the plates 220 and 224 include respective outer planar surfaces or faces 230 and 234 that operatively face toward one another. Furthermore, each plate 220 and 224 has a respective opposed face 236 and 238. The bores 222 open at both the faces 230 and 236. The inner surface 226 forming the bore of the member 207 opens at the outer planar surface 234 and also at an end 239. The cords 210 that form the discrete open loops, loop about and contact the face 236, extend along the axis C within the inner surface 226 and extend through the end 239. Extending from and integral to the faces 236 and 238 are respective elongate cylindrical portions 240 and 242 of the respective anchor member 206 and the terminal member 207. The portion 240 terminates at an end 244. The open cords 210 extend completely through the elongate cylindrical portion 242 and into the bumper 217 and the crimping ring 219.

The portions 240 and 242 are each sized and shaped to attach to at least one bone anchor as will be described in greater detail below. The illustrated portions 240 and 242 are approximately the same size and length, but it is foreseen that different sizes, lengths and shapes are possible, as well as making the portions 240 and 242 from different materials and also making the plates 220 and 224 from materials that are different than the portions 240 and 242. In the illustrated embodiment, the plates 220 and 224 are integral with respective elongate portions 240 and 242 with the members 206 and 207 being made from metal, metal alloys or other suitable materials, including plastic polymers such as polyetheretherketone (PEEK), ultra-high-molecular weight-polyethylene (UHMWP), polyurethanes and composites, including composites containing carbon fiber.

With particular reference to FIGS. 15-19, the sleeve or spacer 214 advantageously cooperates with the cords 210 of the central connection or transition portion 208, providing limitation and protection of movement of the cords 210. The spacer 214 also protects patient body tissue from damage that might otherwise occur in the vicinity of the corded central portion 208. The spacer 214 is substantially cylindrical and made from a plastic, such as a thermoplastic elastomer made from a polyurethane or polyurethane blend. The spacer 214 has an external substantially cylindrical outer surface 250 and an internal surface 252 defining a through bore. The internal surface 252 is further defined by a substantially cylindrical surface 253 having a circular cross section and an outwardly extending substantially conical surface 256 running from the surface 253 to a substantially planar end surface 260. The spacer 214 further includes an opposed planar end surface 262. The inner cylindrical surface 253 opens to the end surface 262.

When operatively cooperating with the looped cords 210, the end surfaces 260 and 262 of the spacer 214 are substantially perpendicular to the axis C. Also, when installed within the inner cylindrical surface 226, the cords 210 are drawn inwardly from the bores 222 and toward the axis C. The conical inner surface 256 of the spacer 214 provides clearance for the cords 210 at the plate surface 230 while the cylindrical inner surface 253 aligns the cords 210 with the inner bore formed by the inner surface 226 of the terminal member 207. It is also foreseen that the cords 210 may be twisted or otherwise connected to form a substantially cylindrical unit prior to insertion in the spacer 214 and the terminal member 207. It is foreseen that in some embodiments, the spacer 214 may be of circular, square, rectangular or other cross-section including curved or polygonal shapes. In the illustrated embodiment, the spacer 214 further includes a compression groove 264. Spacers according to the invention may include one, none or any desired number of grooves. The illustrated groove 264 is substantially uniform and circular in cross-section, being formed in the external surface 250 and extending radially toward the internal surface 252. The size of the internal surface 252 allows for some axially directed sliding movement of the spacer 214 with respect to the cords 210. The cords 210 and cooperating compressible spacer 214 allow for some twist or turn, providing some relief for torsional stresses. The spacer 214, however limits such torsional movement as well as bending movement, providing spinal support, as well as allowing for further compression of the assembly 1 at the flexible central connection portion 208. It is noted that in addition to limiting the bendability of the central connection portion 208 and thus providing strength and stability to the assembly 201, the spacer 214 also keeps scar tissue from growing into the portion 208 through the cords 210, thus eliminating the need for a sheath-like structure to be placed, adhered or otherwise applied to the cords 210 on the central connection portion 208. In order to reduce the production of micro wear debris, that in turn may cause inflammation, the spacer 214 inner surfaces and/or cooperating cord 210 surfaces may be coated with an ultra thin, ultra hard, ultra slick and ultra smooth coating, such as may be obtained from ion bonding techniques and/or other gas or chemical treatments.

With particular reference to FIGS. 15 to 17, the bumper 217 is substantially cylindrical, including an outer surface 270 and an inner surface 272 forming a substantially cylindrical through bore that opens at planar end surfaces 274 and 276 and operatively extends along the axis C. The bumper 217 further includes a compression groove 278 that is similar in form and function to the compression groove 264 of the spacer 214. The bumper 217 is sized and shaped to receive the elongate cords 210 through the inner surface 272. The bumper 217 is preferably made from an elastomeric material such as polyurethane. The bumper 217 provides axial elastic distraction of the cords 210 as will be described in greater detail below.

Also with reference to FIGS. 15 to 17, the crimping ring 219 is substantially cylindrical and includes an outer surface 280 and an inner surface 282 forming a substantially cylindrical through bore that opens at planar end surfaces 284 and 286 and operatively extends along the axis C. The crimping ring 219 is sized and shaped to receive the elongate cords 210 through the inner surface 282. The crimping ring 219 further includes a pair of crimp or compression grooves 288 that are pressable and deformable inwardly toward the axis C upon final tensioning of the cords 210 during assembly of the connector 201 to engage and hold the cords 210 in tension and thereby transmit compressive force to the elastic spacer 214. The crimping ring 219 is preferably made from a stiff, but deformable material, including metals and metal alloys. As will be discussed with respect to a further embodiment of the invention described below, the cords 210 may be threaded through two crimping rings 219 placed adjacent to one another, with a preliminary crimping ring being at a terminal end of the assembly 201. Such a preliminary ring is crimped to initially lock the assembly together with the cords 210 in tension. If further creep and deformation of the cords 210 decreases the axial tension on the cords 210 within the assembly 201, the cords 210 may be re-tensioned and locked into place with the second or final crimping ring. The preliminary crimping ring may then be sliced off of the assembly 201 and discarded.

With reference to FIG. 12, the dynamic connecting member assembly 201 cooperates with at least a pair of bone anchors, such as the polyaxial bone screws, generally 75, and cooperating closure structures 77 described previously herein, the assembly 201 being captured and fixed in place at the rigid portions 240 and 242 by cooperation between the bone screws 75 and the closure structures 77. The dynamic section 208, that is pre-loaded and pre-tensioned, is disposed between the bone screws 75.

With particular reference to FIGS. 12 and 15-17, the longitudinal connecting member assembly 201 is factory assembled by looping six ties 210 about and through the bores 222 of the plate 220 of the anchor member 207 to form the twelve strands or cords 210 that are then threaded through the remaining components of the assembly 201. It is noted that the ties 210 may be initially tensioned to steady state and thereafter further tensioned after assembly with the other components. Alternatively, the twelve cords or strands 210 that are anchored to the member 206 are initially passed through the spacer 214 inner surface 252, followed by the terminal member 207 internal surface 226, then the bumper 217 inner surface 272 and finally the crimping ring 219 inner surface 282 and out the end 286. Thereafter, the spacer 214, the terminal member 207, the bumper 217 and the crimping ring 219 are snugged up against the plate 220 of the anchor member 206 and tension is applied to the bundle of twelve cords 210. Tension is increased on the cord bundle 210 until the elastic spacer 214 and the elastic bumper 217 are compressed and the cords 210 have stopped stretching. Thereafter, the crimping ring 219 is crimped using a tool (not shown) that presses on the opposed grooves 288 and deforms toward the axis C to make contact and firmly grip the cords 210, keeping the cords 210 in the desired tension and locking the components of the assembly 201 in place. The resulting connecting member assembly 201 is thus dynamically loaded with the cords 210 in tension and the spacer 214 and elastic bumper 217 in compression. In some embodiments according to the invention it may be desirable to place one or more pins through the plates 220 and 224 and into the spacer 214 to prevent rotation of the spacer 214 about the axis C relative to the plates 220 and 224. It may also be desirable to use such pins as x-ray markers.

With further reference to FIG. 12, the pre-loaded connecting member assembly 201 is eventually positioned in an open or percutaneous manner in cooperation with the at least two bone screws 75 with the spacer 214 disposed between and spaced from the two bone screws 75 and with the portions 240 and 242 each being within a U-shaped channel of a cooperating bone screw 75. A closure structure 77 is then inserted into and advanced between the arms 85 of each of the bone screws 75. The closure structure 77 is rotated, using a tool (not shown) engaged with the inner drive 92 until a selected pressure is reached at which point the section 240 or 242 is urged toward, but not completely seated in the U-shaped channel of the bone screw 75. For example, about 80 to about 120 inch pounds pressure may be required for fixing the bone screw shank 80 with respect to the receiver 81 at a desired angle of articulation.

The assembly 201 is thus substantially dynamically loaded and oriented relative to the cooperating vertebra, providing relief (e.g., shock absorption) and protected movement with respect to flexion, extension, distraction and compressive forces placed on the assembly 201 and the two connected bone screws 75. The looped cords 210 and the spacer 214 allow for some twisting or turning, providing some relief for torsional stresses. Furthermore, the compressed spacer 214 places some limits on torsional movement as well as bending movement, to provide spinal support. The pre-loaded cords 210 (in tension) and spacer 214 (in compression) allow for compression and some extension of the assembly 201 located between the two bone screws 75, e.g., shock absorption. Disassembly, removal and replacement of the connecting member assembly 201 with a more or less rigid connecting member may be performed in a manner as previously described herein with respect to the connecting member assembly 1.

With reference to FIGS. 20-22, another longitudinal connecting member assembly according to the invention, generally 301, has a central axis D and includes an intermediate rigid member 305, a rigid anchor member 306, a rigid terminal member 307 and first and second dynamic connection portions or sections 308 and 308A. An open loop cord bundle 310 extends through both the sections 308 and 308A. The dynamic sections 308 and 308A further include respective spacers 314 and 314A. The connecting member assembly 301 provides for two dynamic support sections between a plurality of vertebrae. The illustrated embodiment is shown attached to three bone screws 75 and cooperating closure structures 77 previously described herein. The illustrated rigid members 305, 306 and 307 are each sized for attachment to a single bone anchor or screw. However, it is noted that each such rigid member 305, 306 and 307 may be of greater length (along the axis D) for operative attachment to two or more bone anchors. Furthermore, more than one rigid member 305 may be disposed between rigid members 306 and 307 to provide a plurality of dynamic sections.

The connecting member assembly 301 is substantially similar to the connecting member assembly 201 previously described herein with the exception of three components: the additional intermediate rigid member 305, the additional spacer 314A and the additional crimping ring 319A. The illustrated members 306 and 307 are identical or substantially similar to respective members 206 and 207 previously described herein with respect to the connecting member 201, the member 306 having an end plate 320 and a plurality of bores 322 similar to the plate 220 and bores 222 previously described herein and the member 307 having an end plate 324 and a through bore 326 similar to the plate 224 and bore 226 previously described herein with respect to the member 207. Also, the open looped cord bundle 310 is identical or substantially similar to the open looped cord bundle 210, with the exception that the bundle 310 is of greater axial length (along the axis D) as compared to the corded bundle 210 previously described herein with respect to the connecting member 201. The spacer 314 that is disposed between the member 306 and the member 305 is identical or substantially similar to the spacer 214 previously described herein with respect to the connecting member 201. Also, the elastic bumper 317 and both crimping rings 319 and 319A are identical or substantially similar to the respective bumper 217 and crimping ring 219 previously described herein with respect to the connecting member 201.

With particular reference to FIGS. 20 and 21, the intermediate rigid member 305 is disposed between the members 306 and 307 and provides for an additional dynamic connection section 308A. In particular, the member 301 includes a pair of opposed end plates 382 and 383 and an integral cylindrical mid-portion 384 that extends therebetween. The end plates 382 and 383 are identical or substantially similar to the plate 324 of the member 307. The member 305 further includes a through bore 386 running through the entire member 305, from the end plate 382 to the end plate 383 and axially centrally through the cylindrical mid-portion 384. The illustrated cylindrical mid-portion 384 is sized to be received between arms 85 of at least one bone screw 75.

The spacer 314 receives the cord bundle 310 at a location between the plate 320 of the anchor member 306 and the plate 382 of the intermediate rigid member 305. The spacer 314A receives the cord bundle 310 at a location between the plate 383 of the member 305 and the plate 324 of the terminal member 307. The illustrated spacer 314A is substantially similar to the spacer 314 and the spacer 214 previously described herein with respect to the connecting member assembly 201, having an outer cylindrical surface 390, an inner surface 392 defining a through bore running between planar surfaces 394 and 395 and at least one outer compression groove 396. However, unlike the spacers 214 and 314, the inner surface 392 of the spacer 314A is cylindrical and defines a bore of constant circular cross-section sized and shaped to receive a length of the cord bundle 310.

In use, the open looped cord bundle 310 is installed on the anchor member 306 by looping through the apertures 322 in the same manner as previously described herein with respect to the installation of the open looped cord bundle 210 through the apertures 222. The twelve cords or strands 310 that are anchored to the member 306 are initially passed through the bore in the spacer 314, followed by the bore formed by the intermediate member 305 internal cylindrical surface 386, then the bore formed by the spacer 314A internal surface 392, followed by the bore formed by the terminal member 307 internal surface 326, then the bore of the bumper 317, the bore of the crimping ring 319 and finally through the bore of the crimping ring 319A. Thereafter, the spacer 314, the intermediate member 305, the spacer 314A, the terminal member 307, the bumper 317, the crimping ring 319 and the crimping ring 319A are snugged up against the plate 320 of the anchor member 306 and tension is applied to the bundle of twelve cords 310. Tension is increased on the cord bundle 310 until the elastic spacers 314 and 314A and the elastic bumper 317 are compressed and the cords 310 have stopped stretching. Thereafter, the end crimping ring 319A is crimped using a tool (not shown) that presses on opposed grooves of the ring 319A and deforms the ring toward the axis D to make contact and firmly grip the cords 310. If viscoelastic changes decrease the axial tension in the cord bundle 310, the assembly 301 may be re-tensioned by pulling the cords 310 away from the anchor member 306 until a desired tension is again reached. At that time, the other crimping ring 319 is crimped using a tool (not shown) that presses on opposed grooves of the ring 319 and deforms the ring toward the axis D to make contact and firmly grip the cords 310. Thereafter, the crimping ring 319A is sliced off of the assembly 301. The resulting connecting member assembly 301 is thus dynamically loaded with the cords 310 in tension with the spacers 314 and 314A and the elastic bumper 317 in compression.

With further reference to FIG. 20, the pre-loaded connecting member assembly 301 is eventually positioned in an open or percutaneous manner in cooperation with the at least three bone screws 75 with the spacers 314 and 314A disposed between and spaced from the bone screws 75 and with cylindrical portions of each of the members 305, 306 and 307 being within a U-shaped channel of a cooperating bone screw 75. A closure structure 77 is then inserted into and advanced between the arms 85 of each of the bone screws 75. The closure structure 77 is rotated, using a tool (not shown) engaged with the inner drive 92 until a selected pressure is reached, for example, about 80 to about 120 inch pounds pressure may be required for fixing the bone screw shank 80 with respect to the receiver 81 at a desired angle of articulation.

The assembly 301 is thus substantially dynamically loaded and oriented relative to the cooperating vertebra, providing relief (e.g., shock absorption) and protected movement with respect to flexion, extension, distraction and compressive forces placed on the assembly 301 and the three connected bone screws 75. The cords 310 and the spacers 314 and 314A allow for some twisting or turning, providing some relief for torsional stresses. Furthermore, the compressed spacers 314 and 314A place some limits on torsional movement as well as bending movement, to provide spinal support. The pre-loaded cords 310 (in tension) and spacers 314 and 314A (in compression) allow for compression and some extension of the assembly 301 located between the two bone screws 75, e.g., shock absorption. Disassembly, removal and replacement of the connecting member assembly 301 with a more or less rigid connecting member may be performed in a manner as previously described herein with respect to the connecting member assembly 1.

Figure 23:
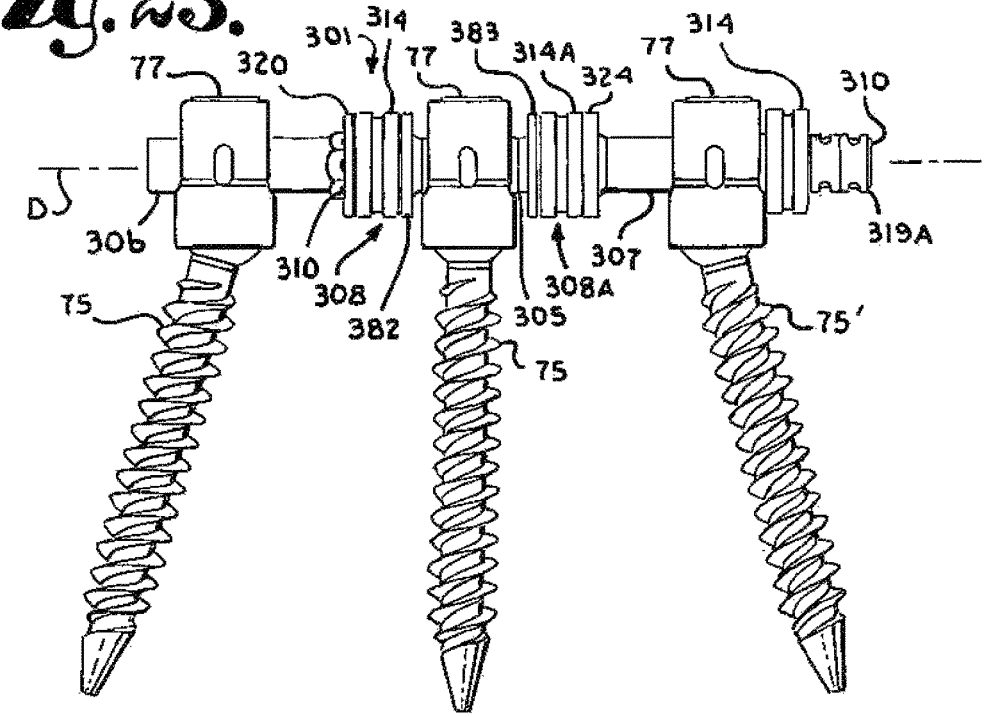
FIG. 23 is a front elevational view of a fifth embodiment of a dynamic fixation longitudinal connecting member according to the invention, similar to that shown in FIG. 20, but including an additional spacer.
Figure 24:
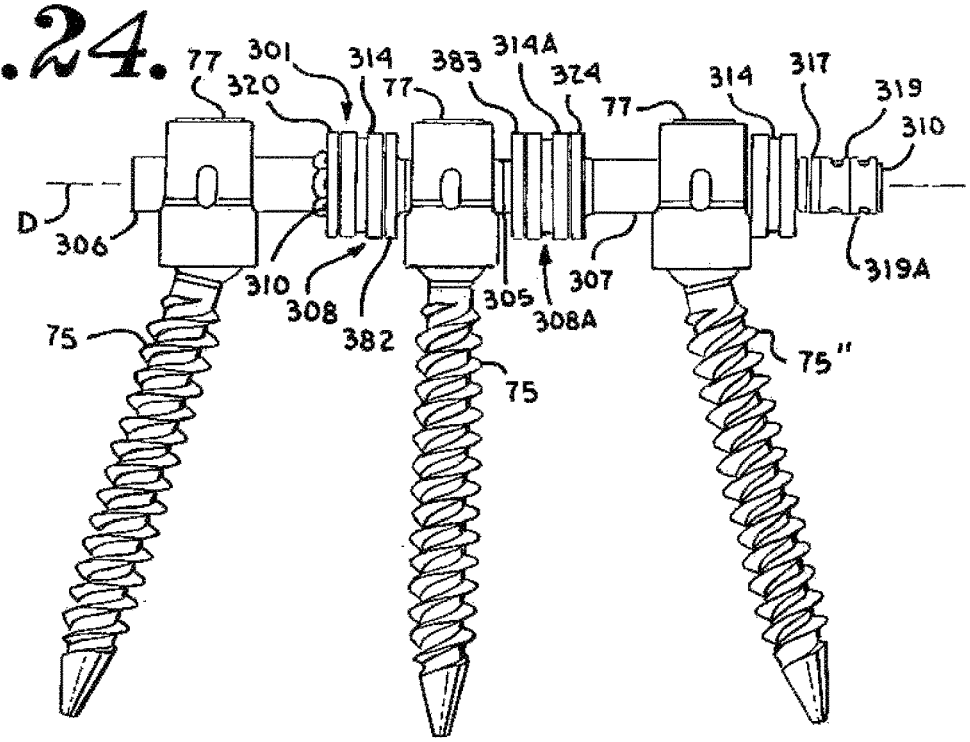
FIG. 24 is a front elevational view of a sixth embodiment of a dynamic fixation longitudinal connecting member according to the invention, also similar to that shown in FIG. 20, but including an additional spacer and bumper.

With reference to FIGS. 23 and 24, dynamic or soft stabilization assemblies are shown that are almost identical to that shown in FIG. 20 with some exceptions. FIG. 23 shows the use of an additional spacer 314 located outside of the bone screw 75'. FIG. 24 illustrates both an additional spacer 314 and an additional elastomeric bumper 317 located outside of the bone screw 75".

Figure 25A:
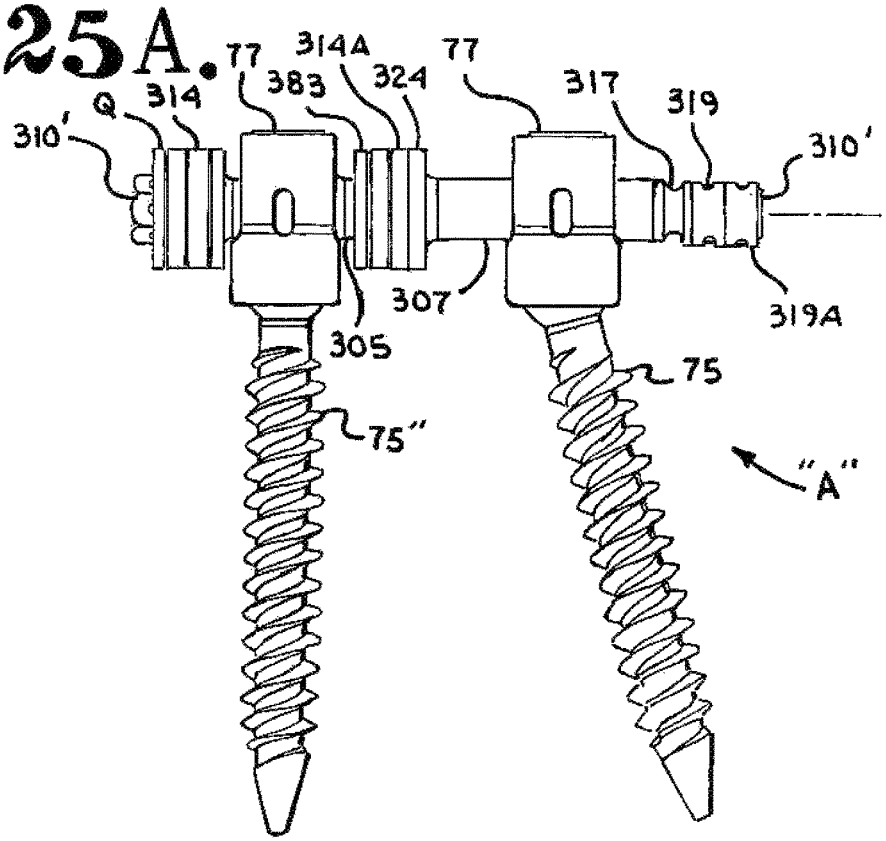
FIG. 25A is a front elevational view of a seventh embodiment of a dynamic fixation longitudinal connecting member according to the invention, shown in a first state or position.
Figure 25B:
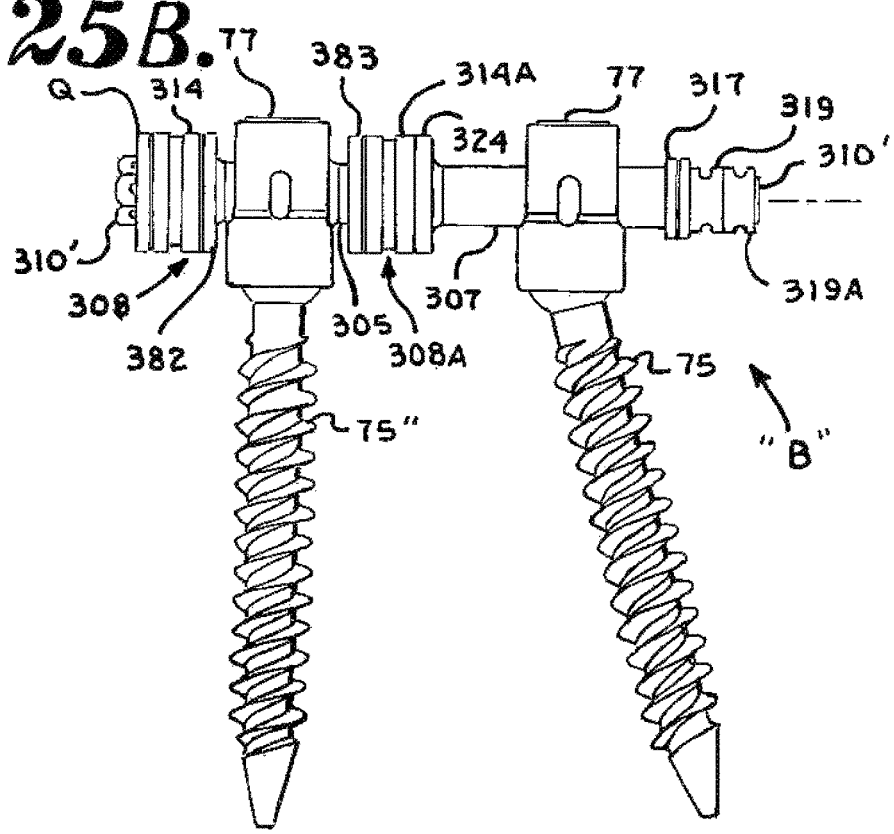
FIG. 25B is another front elevational view of the seventh embodiment of a dynamic fixation longitudinal connecting member according to the invention, shown in a second state or position.

With reference to FIGS. 25A and 25B, a soft stabilization assembly is shown that is substantially similar to that shown in FIG. 20, with the exception that only two bone screws are shown and the member 306 is replaced by a plate Q that fixes the cord or cord bundle 310' at an end of the assembly while the cord is allowed to be slidable with respect to the bone screw 75". FIGS. 25A and B illustrate the assembly in two states of dynamic stabilization that occur without the cord 310' changing length. In state "A" shown in FIG. 25A, both the spacers 314 are compressed, while the bumper 317 is allowed to expand to a neutral state. In state "B" shown in FIG. 25B, the bumper 317 is compressed and the spacers 314 are in an expanded state.

Figure 26A:
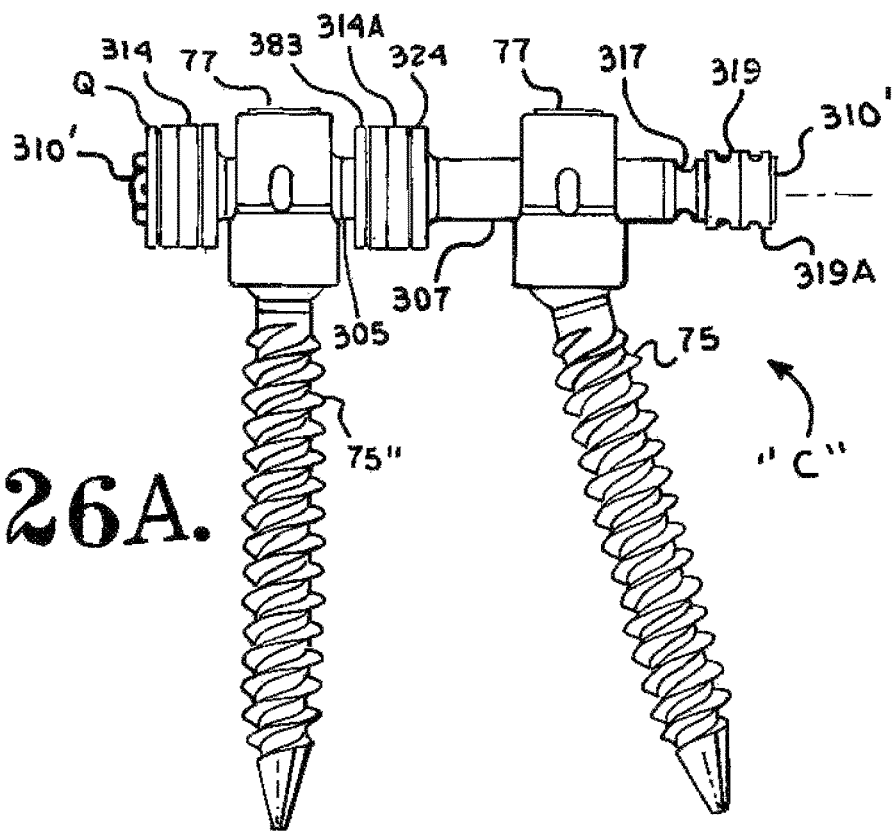
FIG. 26A is another front elevational view of the embodiment shown in FIGS. 25A and B, showing the embodiment in another state or position.
Figure 26B:
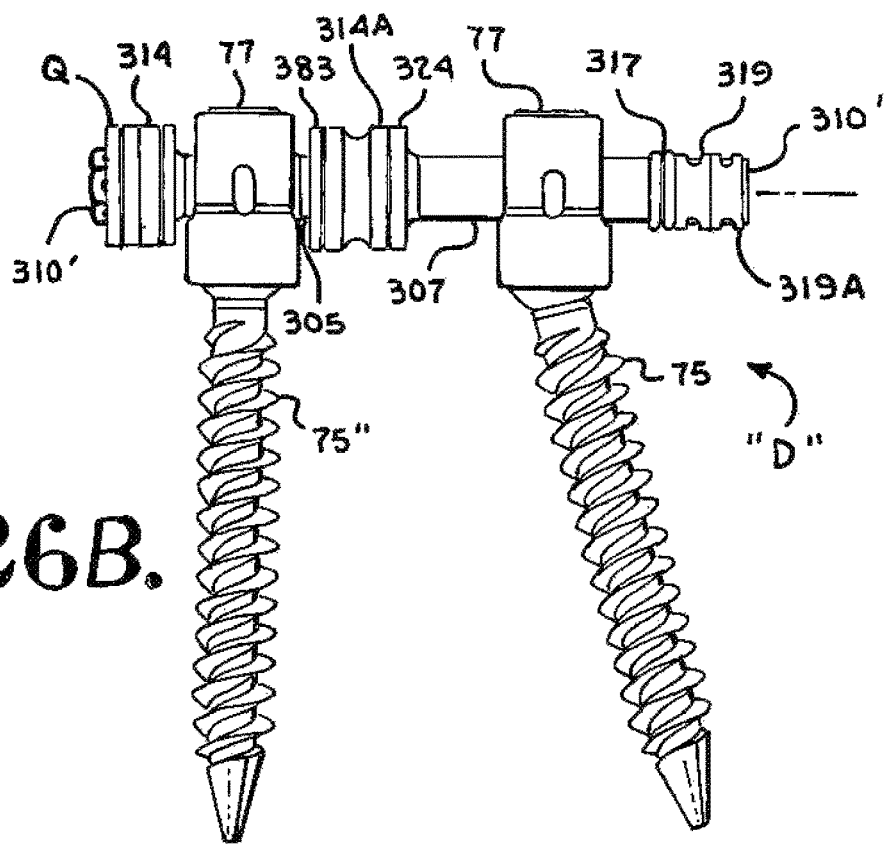
FIG. 26B is another front elevational view of the embodiment shown in FIGS. 25A and B and 26A, showing the embodiment in another state or position.

FIGS. 26A and 26B illustrate the same assembly as in FIGS. 25A and 25B, also in two states of dynamic stabilization. In state "C" shown in FIG. 26A, the bumper 317 is expanded or neutral and both of the spacers 314 are compressed. In state "D" shown in FIG. 26B, the bumper 317 is compressed while the central spacer 314 expands to a neutral or near neutral state, while the end spacer 314 remains compressed.

Figure 27A:
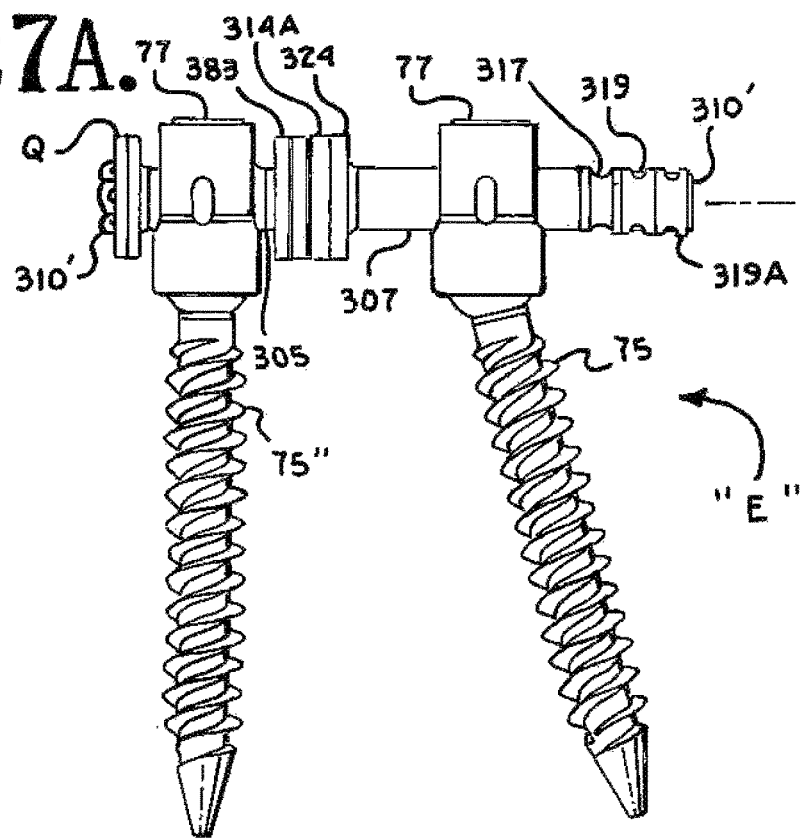
FIG. 27A is a front elevational view of an eighth embodiment of a dynamic fixation longitudinal connecting member according to the invention, shown in a first state or position.
Figure 27B:
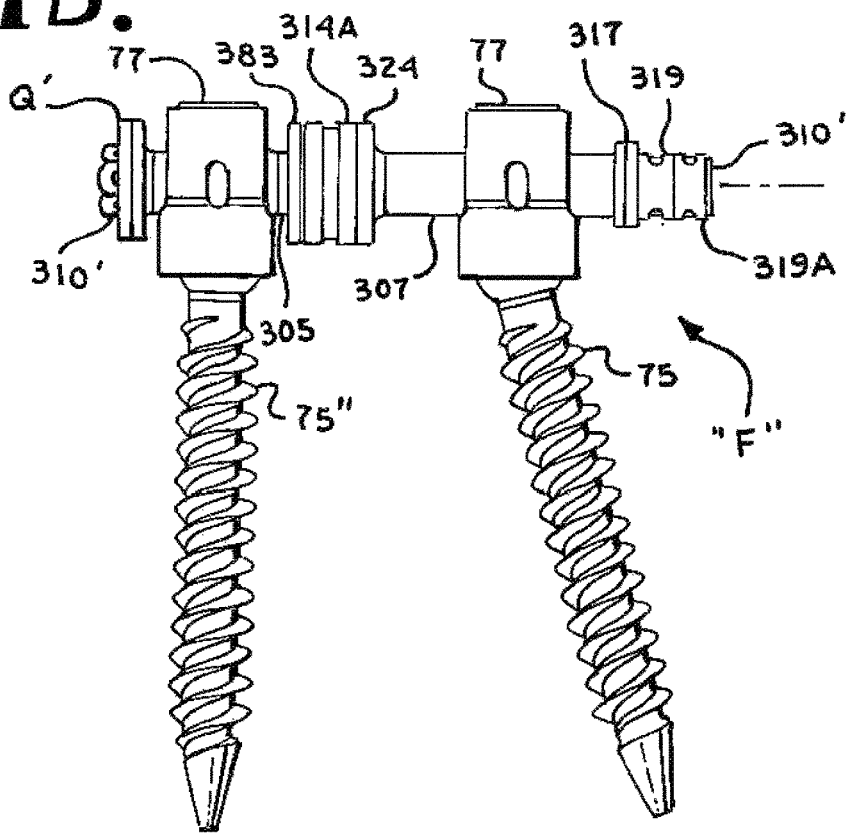
FIG. 27B is a front elevational view of the eighth embodiment of a dynamic fixation longitudinal connecting member according to the invention, shown in a second state or position.

With reference to FIGS. 27A and 27B, a soft stabilization assembly is shown that is substantially similar to that shown in FIGS. 25A and B, with the exception that there is no end spacer 314 and an alternative plate or fixer/blocker member Q' fixes the cord or cord bundle 310' at an end of the assembly adjacent one of the bone screws 75". FIGS. 27A and B illustrates the assembly in two states of dynamic stabilization that occur without the cord 310' changing length. In state "E" shown in FIG. 27A, the spacer 314A is compressed, while the bumper 317 is allowed to expand to a neutral state. In state "F" shown in FIG. 27B, the bumper 317 is compressed and the spacer 314A expands.

Figure 28:
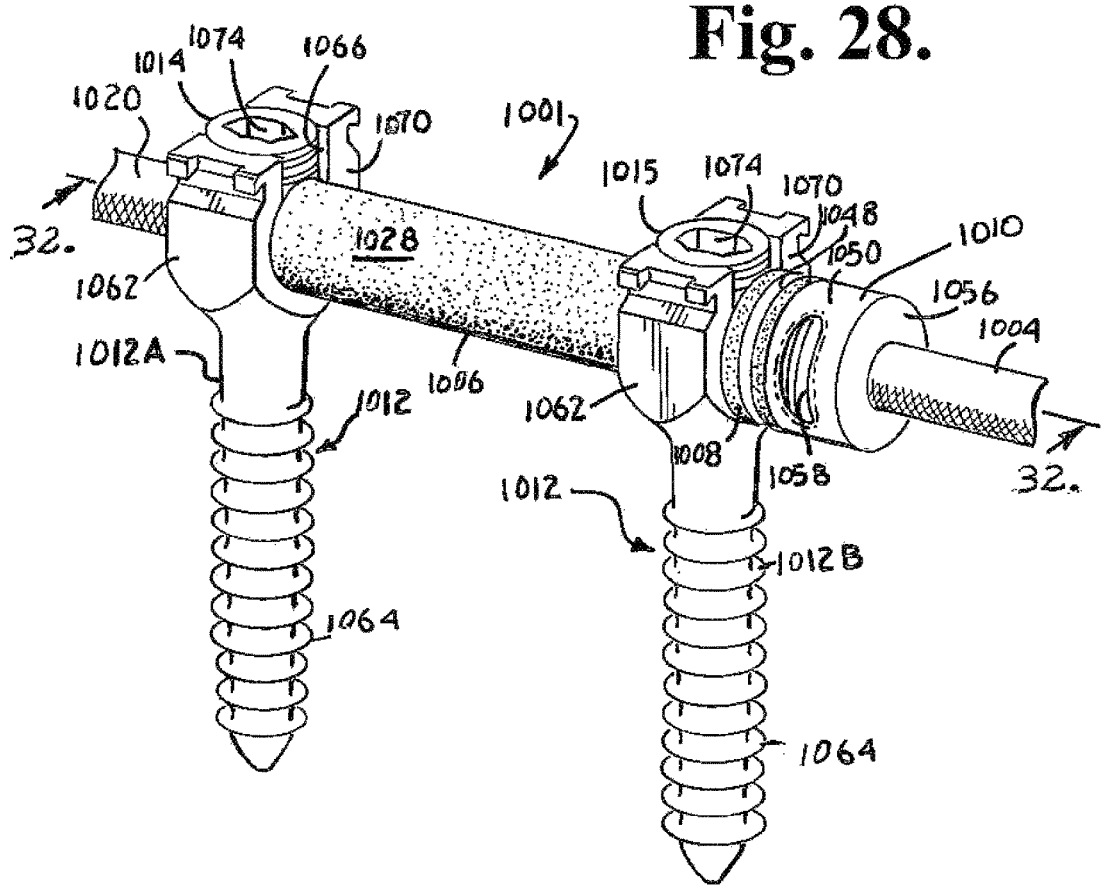
FIG. 28 is a partial perspective view of another soft dynamic stabilization connector of the invention having an inner cord, an outer spacer, an elastic bumper and a fixing structure or blocker, shown as a crimping structure, the connector shown with a pair of open monoaxial bone screws, one with a cord travel or sliding closure top and one with a cord compressing and locking closure top.
Figure 30:
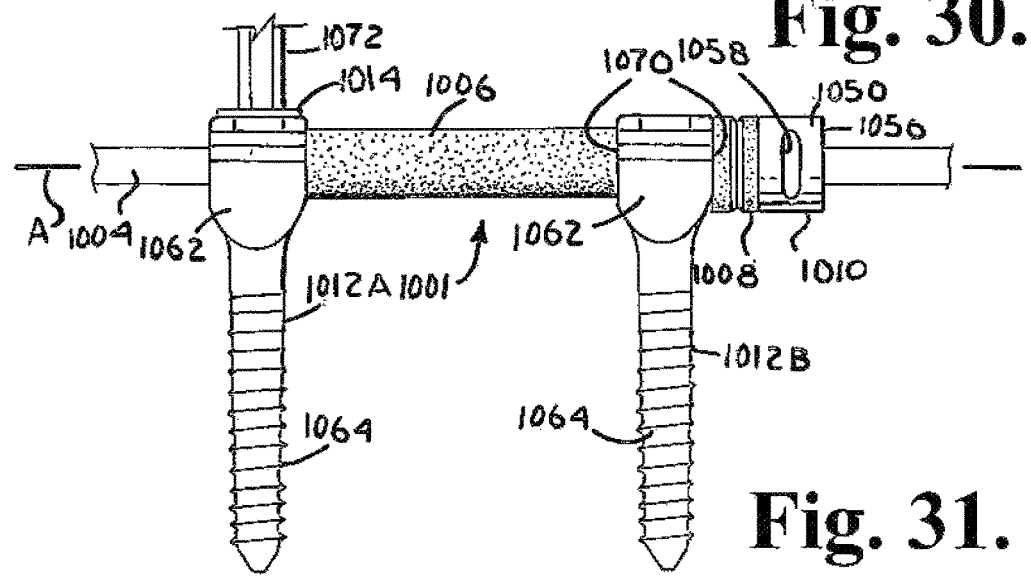
FIG. 30 is a partial front elevational view, similar to FIG. 29 showing a stage of assembly of the connector and bone screws of FIG. 28, showing use of a driving tool for fixing one of the first closure tops against the cord.
Figure 31:
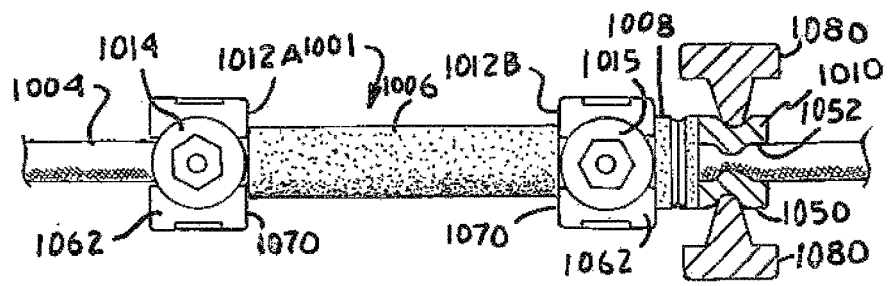
FIG. 31 is a partial top plan view with portions broken away to show the detail thereof, showing use of a crimping tool in a further stage of assembly of the connector and bone screws of FIG. 28.
Figure 32:
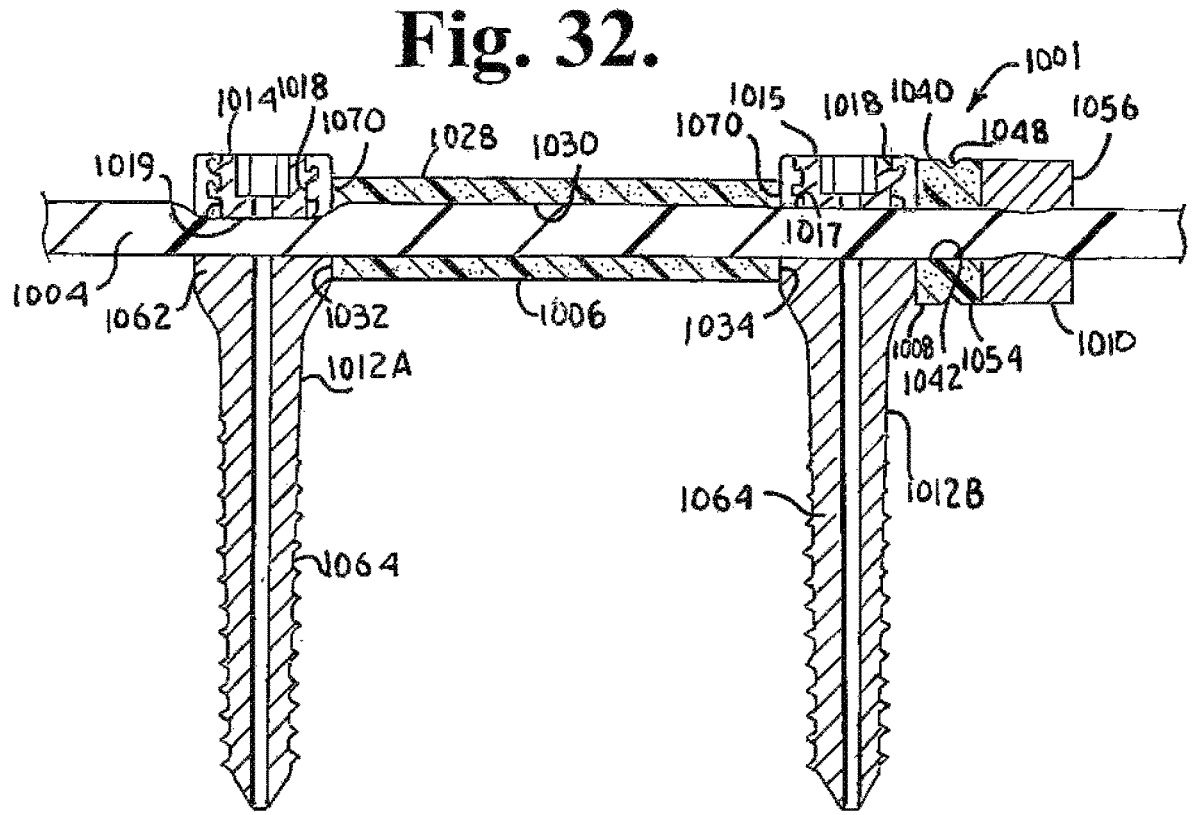
FIG. 32 is an enlarged and partial cross-sectional view taken along the line 32-32 of FIG. 28.

With reference to FIGS. 28-32, the reference numeral 1001 generally designates a non-fusion, soft or dynamic longitudinal stabilization connector assembly of the invention. The illustrated assembly 1001 includes the following components: an elongate bendable and flexible core in the form of a cord 1004; at least one cannulated spacer 1006; an elastic bumper 1008; and a fixing structure or blocking member, such as a crimping structure 1010. The assembly 1001 is shown with a pair of open monoaxial bone screws, generally 1012, the assembly 1001 extending substantially linearly along a central axis A in FIG. 30, for example. For purposes of this application, the identical bone screws 1012 are identified as 1012A and 1012B as the one bone screw 1012A cooperates with a first locking and cord pressing closure top 1014 and the other bone screw 1012B cooperates with a second locking limited travel closure top 1015 that allows for slip or slide of the cord 1004 within the bone screw 1012B. The closure tops 1014 and 1015 are substantially similar to one another with the exception that the top 1015 is sized and shaped to bottom out on a lower seating surface 1017 of a run-out of an inner guide and advancement structure 1018 of the bone screw 1012 that mates with the outer guide and advancement structure of the closure top 1014 or the closure top 1015. The closure top 1014 further includes an end or bottom portion 1019 that extends beyond the run-out seating surface 1017 and abuts against and fixes the cord to the bone screw. The guide and advancement run-out seating surface 1017 is best shown and described with respect to an alternative bone screw 1112 and 1112' described in greater detail below with reference to FIGS. 33-41. Also, as will be described in more detail below, the bone screw 1012A cooperates with the closure top 1014 to fix a portion of the cord 1004 to the bone screw 1012A while the bone screw 1012B engages and fixes the closure top 1015 to the screw 1012B to capture a portion of the cord 1004 within the bone screw 1012B, but allow for sliding movement of the cord 1004 with respect to the bone screw 10123. The elongate inner cord core 1004 is slidingly received within the spacer 1006 and the bumper 1008, and initially within the blocker or crimping structure 1010, as will be described in greater detail below. The cord 1004 is eventually tensioned and fixed in such tensioned state by the crimping structure or blocker 1010 and the bone screw 1012A. In other embodiments according to the invention, the structure 1010 may include a threaded aperture (not shown) and further include a cooperating set screw in addition to or in lieu of crimping. In such embodiments, as shown in other embodiments of the invention described in more detail below, the set screw rotatably mates with the structure 1010 at the threaded aperture and is rotated until a bottom surface of the screw presses against and, in some embodiments, penetrates the cord, fixing the cord within the structure 1010. As will be described in greater detail below, when fully assembled and all the components are fixed in position as shown in FIGS. 28 and 32, for example, the cord 1004 is in tension, the spacer 1006 may be in compression or in a neutral state, and the bumper 1008 is in compression.

It is noted that in other embodiments according to the invention, both the bone screws 1012A and 1012B may be mated with a locking limited travel closure top 1015 and at least one additional blocker or crimping structure is included generally opposite the crimping structure 1010 in the overall assembly to result in a cord that is tensioned along the assembly but in sliding cooperation with two or more bone anchors of such assembly. It is also noted that additional spacers 1006 and bone screws 1012 cooperating with closure tops 1015 may be utilized according to the invention, providing longer assemblies of the invention with one of the spacers 1006 placed between each bone screw and the bumper 1008 and the crimping structure 1010 placed at one or both ends of such assembly next to a bone screw 1012 cooperating with a closure top 1015 or two such closure tops 1015. Also, as described in greater detail below, bone screws, spacers, bumpers and crimping structures or other blockers of the invention may be sized, shaped and used with hard or deformable rods and bars, alternatively to the cord 1004.

Although the screws 1012 are illustrated, it is noted that the assembly 1001 may cooperate with a variety of bone screws and other bone anchors, including closed bone screws, hinged bone screws, polyaxial bone screws, with or without compression inserts, and bone hooks that may in turn cooperate with a variety of closure structures having threads, flanges, or other structure for fixing the closure structure to the bone anchor, and may include other features, for example, external or internal drives, break-off tops and inner set screws. A closed bone anchor with or without a set screw may also be used in the invention to capture the cord 1004 in sliding, but not fixed engagement. The bone anchors, closure structures and the connecting member 1001 are then operably incorporated in an overall spinal implant system for correcting degenerative conditions, deformities, injuries, or defects to the spinal column of a patient.

The connecting member assembly 1001 is elongate, with the inner core 1004 being any soft elongate material including, but not limited to cords, threads, strings, bands, cables or fibers that may be single or multiple strands, including twisted, braided or plaited materials. The illustrated cord 1004 has a substantially uniform body 1020 of substantially circular cross-section, a first end 1022 and an opposed second end 1024, the cord 1004 being cut to length as required by the surgeon. Initially, the cord 1004 is typically of a length longer than shown in the drawings to allow for gripping of the cord 1004 during assembly with the other components of the assembly 1001 and also for tensioning and attachment to the bone screws 1012A and 1012B as will be described in greater detail below. The cord 1004 may be made from a variety of materials, including polyester or other plastic fibers, strands or threads, such as polyethylene-terephthalate. The cord 1004 may be placed under axial tension prior to final installation between the bone screws 1012A and 1012B, for example by being tensioned along the axis A for a selected time to lengthen and otherwise deform the cord 1004 during a primary creep stage. After the cord 1004 reaches a secondary or steady-state creep, further tension is placed on the cord 1004 in preparation for fixing between the bone screw 1012A and the crimping structure 1010 as will be described in greater detail below. It is noted that the cord 1004 typically does not illustrate elastic properties, such as any significant additional lengthening with axial traction, after the assembly 1001 is operatively assembled within a human body, but the elastic bumper 1008 will allow for relative movement between the fully stretched cord 1004 and the bone screw 1012B in response to spinal flexion, extension and any movement that may draw the bone screw 1012B away from the bone screw 1012A.

Figure 29:
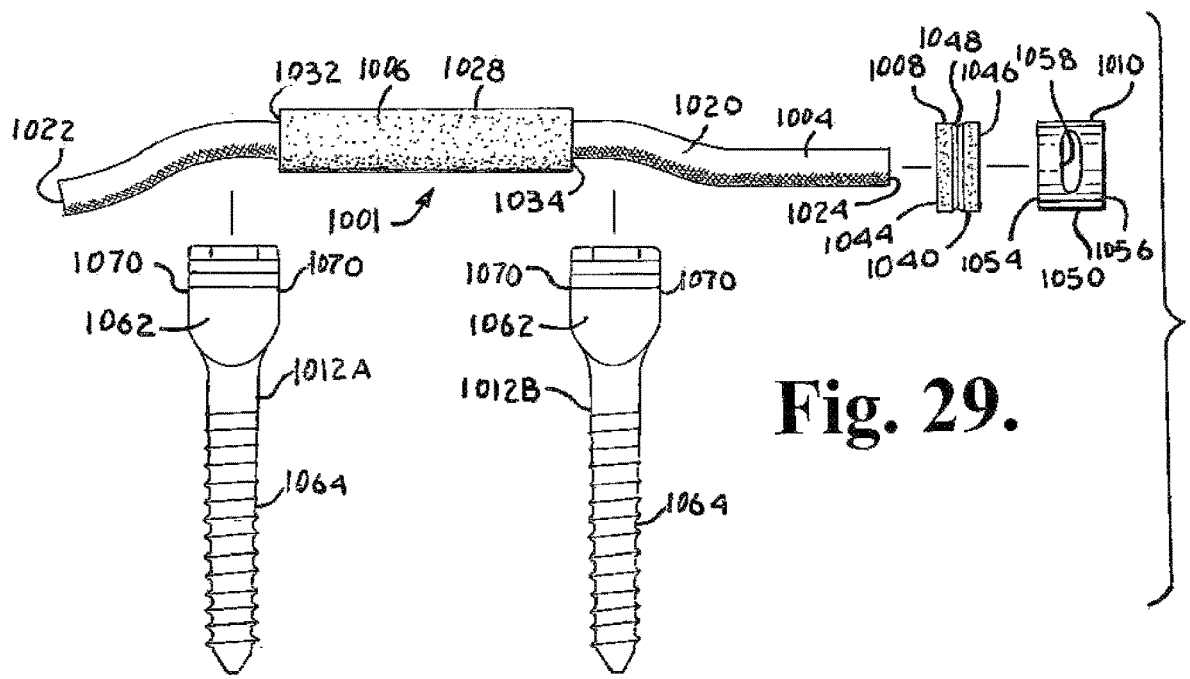
FIG. 29 is a partial and reduced and exploded front elevational view of the connector and bone screws of FIG. 28, shown without the closure tops.

With particular reference to FIGS. 28, 29 and 32, the spacer 1006 is sized and shaped to be slidingly received over the cord 1004 and may be made from a variety of elastic and more rigid materials, including, but not limited to natural or synthetic elastomers such as polyisoprene (natural rubber), and synthetic polymers, copolymers, and thermoplastic elastomers, for example, polyurethane elastomers such as polycarbonate-urethane elastomers. In order to have low or no wear debris, the spacer 1006 inner and side surfaces may be coated with an ultra thin, ultra hard, ultra slick and ultra smooth coating, such as may be obtained from ion bonding techniques and/or other gas or chemical treatments. The illustrated spacer 1006 has an external substantially cylindrical outer surface 1028 and an internal substantially cylindrical surface 1030. The surface 1030 is sized and shaped to closely cooperate and fit about the cord 1004 and yet allow some sliding movement of the cord 1004 with respect to the spacer 1006 along the axis A. The spacer 1006 includes opposed substantially planar and annular end surfaces 1032 and 1034 that are sized and shaped to abut against planar surfaces of the bone screws 1012A and 1012B, respectively. When initially assembled with the other components of the connecting member assembly 1001, the surfaces 1032 and 1034 are substantially perpendicular to the axis A. It is foreseen that in some embodiments, the spacer 1006 may be of smaller or larger outer circular cross section, or of a square, rectangular or other inner or outer cross-section including other curved or polygonal shapes. The spacer 1006 may further include one or more compression grooves that allow for some additional compression of the spacer 1006 when pressed upon in an axial direction between the bone anchors 1012A and 1012B. Typically, such a compression groove is substantially uniform and circular in cross-section, being formed in the external surface 1028 and extending radially toward the internal surface 1030. The spacer can have an off-axial lumen.

Also with particular reference to FIGS. 28, 29 and 32, the elastic bumper 1008 is annular and includes an outer cylindrical surface 1040, an inner cylindrical surface 1042, an end surface 1044 and an opposed end surface 1046. The illustrated bumper 1008 further includes a compression groove 1048 that allows for some additional compression of the bumper 1008 when pressed upon in an axial direction A between the bone anchor 1012B and the crimping ring 1010. The compression groove 1048 is substantially uniform and circular in cross-section, being formed in the external surface 1040 and extending radially toward the internal surface 1042. Bumpers of the invention may include one, none or a plurality of compression grooves. The inner cylindrical surface 1042 forms a bore sized and shaped for closely receiving the cord 1004 therethrough as shown, for example, in FIG. 32. The end surfaces 1044 and 1046 are substantially parallel to one another, but can also be non-parallel.

The bumper 1008 may be made from a variety of elastic materials, including, but not limited to natural or synthetic elastomers such as polyisoprene (natural rubber), and synthetic polymers, copolymers, and thermoplastic elastomers, for example, polyurethane elastomers such as polycarbonate-urethane elastomers. The bumper 1008 is typically shorter in length and more elastic than the spacer 1006, but may be equal to or longer than the spacer and of the same, greater or lesser durometer than the spacer 1006. In order to have low or no wear debris, the bumper 1008 inner and side surfaces may also be coated with an ultra thin, ultra hard, ultra slick and ultra smooth coating, such as may be obtained from ion bonding techniques and/or other gas or chemical treatments.

The fixing structure or blocker, illustrated as the crimping structure or ring 1010 is substantially cylindrical and includes an outer surface 1050 and an inner surface 1052 forming a substantially cylindrical through bore that opens at planar end surfaces 1054 and 1056 and operatively extends along the axis A. The crimping ring 1010 is sized and shaped to receive the elongate cord 1004 through the inner surface 1052. The crimping ring 1010 further includes a pair of opposed crimp or compression grooves 1058 that are pressable and deformable inwardly toward the axis A upon tensioning of the cord 1004 and pre-compression of the bumper 1008 during assembly of the assembly 1001. The crimping ring 1010 is preferably made from a stiff, but deformable material, including metals and metal alloys. It is foreseen that in lieu of or addition to the crimping surface, the blocker could include a threaded aperture and a mating locking set screw for engaging and pressing into the cord 1004.

The bone screws generally 1012, and in particular the illustrated screws 1012A and 1012B are open, fixed, mono-axial screws, each having an upper cord receiving portion 1062 integral with a threaded bone attachment portion or shank 1064. The portion 1062 further includes a substantially U-shaped channel 1066 for closely receiving the cord 1004 therethrough, the channel 1066 further having an upper closure top receiving portion with the helically wound guide and advancement structure 1018 thereon for receiving and mating with the closure top 1014 or the closure top 1015. The upper, receiving portion 1062 further includes opposed, substantially parallel side surfaces 1070 that abut against side surfaces of the spacer 1006 or the bumper 1008. However, it is foreseen that according to the invention, other embodiments of the invention may include side surfaces 1070 that angle away or towards one another for lordosing or kyphosing controlling embodiments as previously described in applicant's application U.S. Ser. No. 11/328, 481, incorporated by reference herein.

To provide a biologically active interface with the bone, the threaded shanks 1064 of the bone screws 1012A and 1012B may be coated, perforated, made porous or otherwise treated. The treatment may include, but is not limited to a plasma spray coating or other type of coating of a metal or, for example, a calcium phosphate; or a roughening, perforation or indentation in the shank surface, such as by sputtering, sand blasting or acid etching, that allows for bony ingrowth or ongrowth. Certain metal coatings act as a scaffold for bone ingrowth. Bio-ceramic calcium phosphate coatings include, but are not limited to: alpha-tri-calcium phosphate and beta-tri-calcium phosphate ($Ca_3(PO_4)_2$), tetra-calcium phosphate ($Ca_4P_2O_9$), amorphous calcium phosphate and hydroxyapatite ($Ca_{10}(PO_4)_6(OH)_2$). Coating with hydroxyapatite, for example, is desirable as hydroxyapatite is chemically similar to bone with respect to mineral content and has been identified as being bioactive and thus not only supportive of bone ingrowth, but actively taking part in bone bonding.

With particular reference to FIGS. 28, 29 and 32, the closure structures 1014 and 1015 can be any of a variety of different types of closure structures for use in conjunction with the present invention with suitable mating structure on the interior surface of the receiver 1062 of the open bone screws 1012. The illustrated closure structures 1014 and 1015 are each rotatable between the spaced arms forming the receiver 1062 and are substantially cylindrical, including an outer helically wound guide and advancement structure in the form of a flange form that operably joins with the guide and advancement structure 1018. A driving tool 1072 illustrated in FIG. 30 is sized and shaped for engagement with an internal drive feature 1074 and is used for both rotatable engagement and, if needed, disengagement of the closure 1014 and/or closure 1015 from one of the receivers 1062. The internal drive feature 1074 may take a variety of forms and may include, but is not limited to, a hex shape (as shown), TORX or other features or apertures, such as slotted, tri-wing, spanner, two or more apertures of various shapes, and the like. As stated above, the closure 1014 and the closure 1015 are substantially identical with the exception of a height or depth dimension in the form of the portion or knob 1019 that extends operatively perpendicular to the axis A. The closure structure 1014 that includes the portion 1019 is sized and shaped to be long enough to compress against the cord 1004 and frictionally fix the cord 1004 in the receiver 1062 when fully seated and mated with the guide and advancement structure 1018. (See, e.g., FIG. 41 that shows a similar closure 1114 that abuts against a run-out seat 1117' and has an extended portion 1119 for pressing down on a core, such as a cord or rod or bar). The illustrated closure top 1014 may further include points or projections for piercing into the cord 1004 to provide enhanced contact and fixing of the cord 1004 to the receiver 1062. The closure 1015 is sized and shaped to be long enough to fully seat within the receiver 1062 and mate with the guide and advancement structure 1018 run-out seating surface 1017 in order to fix the closure 1015 in the bone screw and capture the cord 1004 within the receiver 1062. However, the closure 1015 is too short to fix the cord 1004 against the receiver 1062. Rather, when the closure 1015 is fully seated and mated in the receiver 1062, the cord 1004 remains in slidable relationship with the bone screw 1012B and is not fixed against a surface of the receiver 1062. See, e.g., FIG. 36 that shows a similar closure 1115 that abuts against a run-out seat 1117 and is spaced from or in sliding engagement with a core, such as a cord or cable or rod or bar. In other embodiments, the closure 1115 may include an upper stop or cap portion 1187 (shown in phantom) and the receiver run-out seat 1117 need not extend inwardly to the extent shown in FIG. 36. In such an alternative embodiment, the cap portion 1187 abuts the receiver top surface which keeps the closure in a desired location spaced from or in sliding engagement with a cord, cable, rod or bar.

In use, the two bone screws 1010 and 1012 are implanted into vertebrae for use with the dynamic connecting member 1001. Each vertebra may be pre-drilled to minimize stressing the bone. Furthermore, if a cannulated bone screw shank and/or closure top is utilized (as illustrated), each vertebra will have a guide wire or pin (not shown) inserted therein that is shaped for the bone screw cannula of the bone screw shank 1064 and provides a guide for the placement and angle of the shank 1064 with respect to the cooperating vertebra. A further tap hole may be made and the shank 1064 is then driven into the vertebra by rotation of a driving tool (not shown) that engages a driving feature on or near the top portion 1062 of the screw 1012. It is foreseen that the screws 1012A and 1012B and the dynamic connector 1001 can be inserted in a percutaneous or minimally invasive surgical manner.

With particular reference to FIGS. 29-31, the dynamic connector assembly 1001 is assembled by inserting the cord 1004 into the through bore formed by the internal surface 1030 of the spacer 1006. Also as indicated in FIGS. 29 and 30, the cord 1004 is first received into the U-shaped opening 1066 of the open bone screw 1012A and the U-shaped opening 1066 of the bone screw 1012B, with the spacer 1006 being disposed between facing surfaces 1070 of bone screws 1012A and 10123. The closure top 1014 is rotated and driven into the receiver 1062 of the bone screw 1012A until the closure top 1014 frictionally engages the cord 1004 and fixes the cord 1004 to the screw 1012A. Before or after the closure top 1014 is tightened, the closure top 1015 may be inserted and rotated into the receiver 1062 of the bone screw 1012B until the top 1015 is fully seated and engaged with such receiver run-out surface 1017, capturing but not fixing the cord 1004 to the bone screw 1012B. The bumper 1008 is threaded along the cord 1004 with the cord sliding through the through-bore formed by the inner surface 1042 until the bumper face 1044 abuts against the surface 1070 of the bone screw 10123 located opposite the spacer 1006. The crimping structure or blocker 1010 is threaded along the cord 1004 with the cord sliding through the through-bore formed by the inner surface 1052 until the crimper face 1054 abuts against the bumper face 1046.

The cord 1004 is tensioned and the bumper 1008 is compressed against the bone screw 1012B by axial movement of the crimping structure 1010 against the bumper 1008, squeezing the bumper 1008 between the bone screw 1012B and the crimping structure 1010. The spacer 1006 also may be compressed at this time. With particular reference to FIG. 31, a crimping tool 1080 is used to frictionally attach the tensioned cord 1004 to the crimping structure 1010, thereby holding the cord 1004 in tension between the bone screw 1012A and the crimping structure 1010 and also compressing the bumper 1008 against the bone screw 1012B.

The resulting connecting member assembly 1001 is loaded with the cord 1004 in tension and the bumper 1008 and optionally the spacer 1006 in compression. The assembly 1001 is thus substantially dynamically loaded and oriented relative to the cooperating vertebra, providing relief (e.g., shock absorption) and protected movement in response to spinal flexion and extension, and further responding to distractive or tensioning forces as well as to compressive forces.

If removal of the dynamic connector assembly 1001 from the bone screws 1012A and/or 1012B is necessary, or if it is desired to release the assembly 1001 at a particular location, disassembly is accomplished by using the driving tool 1072 with a driving formation cooperating with the closure tops 1014 and 1015 to rotate and remove the closure top from the bone screw 1012A and/or 1012B. Disassembly is then accomplished in reverse order to the procedure described previously herein for assembly.

With reference to FIGS. 33-36, a bone screw 1112 is illustrated that is identical to the bone screw 1012 of the assembly 1001 with the exception that the U-shaped channel 1066 formed by inner surfaces of the screw 1012 has been replaced with a substantially rectangular channel 1166 formed by opposed planar surfaces 1167 and a bottom planar surface 1168. The bone screw 1112 has a receiver 1162 and a shank 1164, the receiver 1162 having a discontinuous guide and advancement structure 1118 that is formed in the opposed surfaces 1167. The bone screw 1112 may be utilized in an assembly 1101 substantially similar to the assembly 1001 that includes a cord 1104 identical or substantially similar to the cord 1004 and further includes the spacer 1006, elastic bumper 1008, crimping structure 1010 of the assembly 1001 previously described herein. Because of the squared off shape of the channel 1166, the bone screw 1112 may also be readily used with other longitudinal connecting members, such as the bar 1105 shown in FIG. 34 and the rod 1106 shown in FIG. 37. The bar 1105 and the rod 1106 may be made of a variety of materials ranging from deformable plastics to hard metals, depending upon the desired application. Thus, bars and rods of the invention may be made of materials including, but not limited to metal, metal alloys or other suitable materials, plastic polymers such as polyetheretherketone (PEEK), ultra-high-molecular weight-polyethylene (UHMWP), polyurethanes and composites, including composites containing carbon fiber, natural or synthetic elastomers such as polyisoprene (natural rubber), and synthetic polymers, copolymers, and thermoplastic elastomers, for example, polyurethane elastomers such as polycarbonate-urethane elastomers. Whether the longitudinal connecting member of the invention is a cord, rod or bar; hard-surfaced or soft and deformable; or elastic or non-elastic, the combination of a limited travel closure top that allows the connecting member some movement within the bone screw further cooperating with a bumper and a connector holding structure or blocker such as the crimping structure 1010, advantageously allows for limited movement of the connector with respect to the bone screw, creating a dynamic connection between spinal assembly and cooperating vertebrae.

Figure 35:
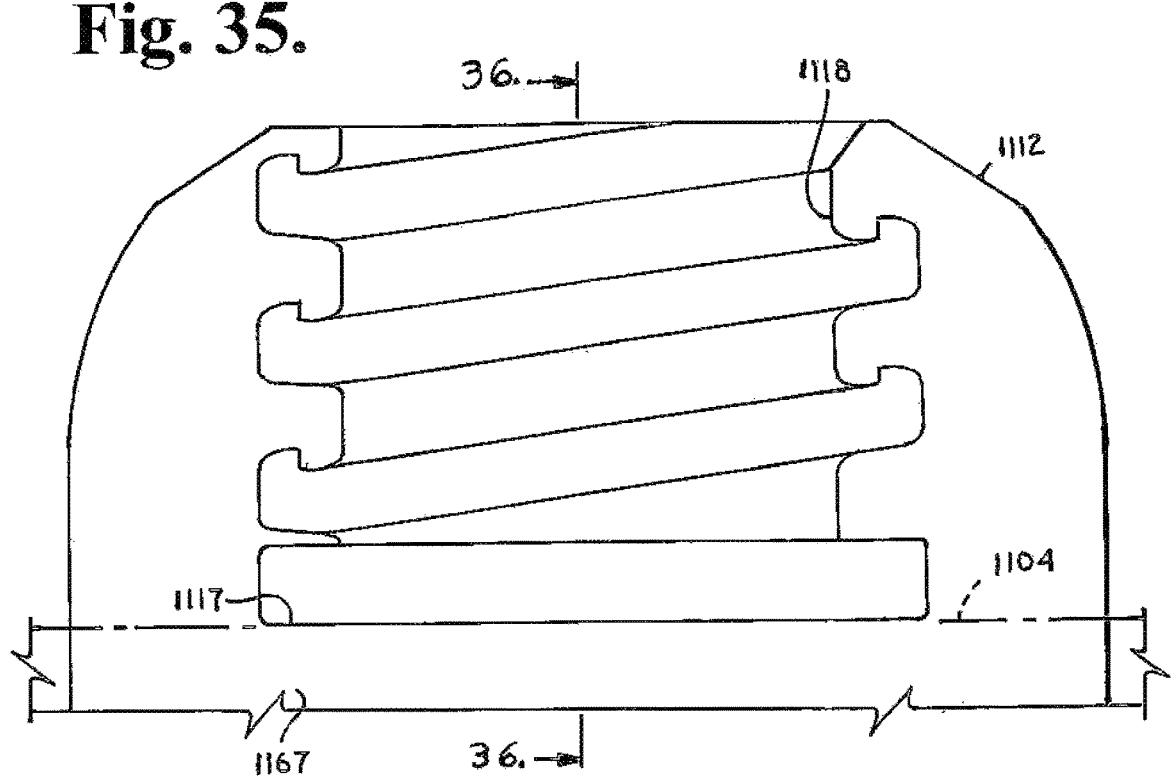
FIG. 35 is an enlarged and partial cross-sectional view of the bone screw of FIG. 33 taken along the line 35-35 of FIG. 33 and showing a portion of the cord in phantom.
Figure 36:
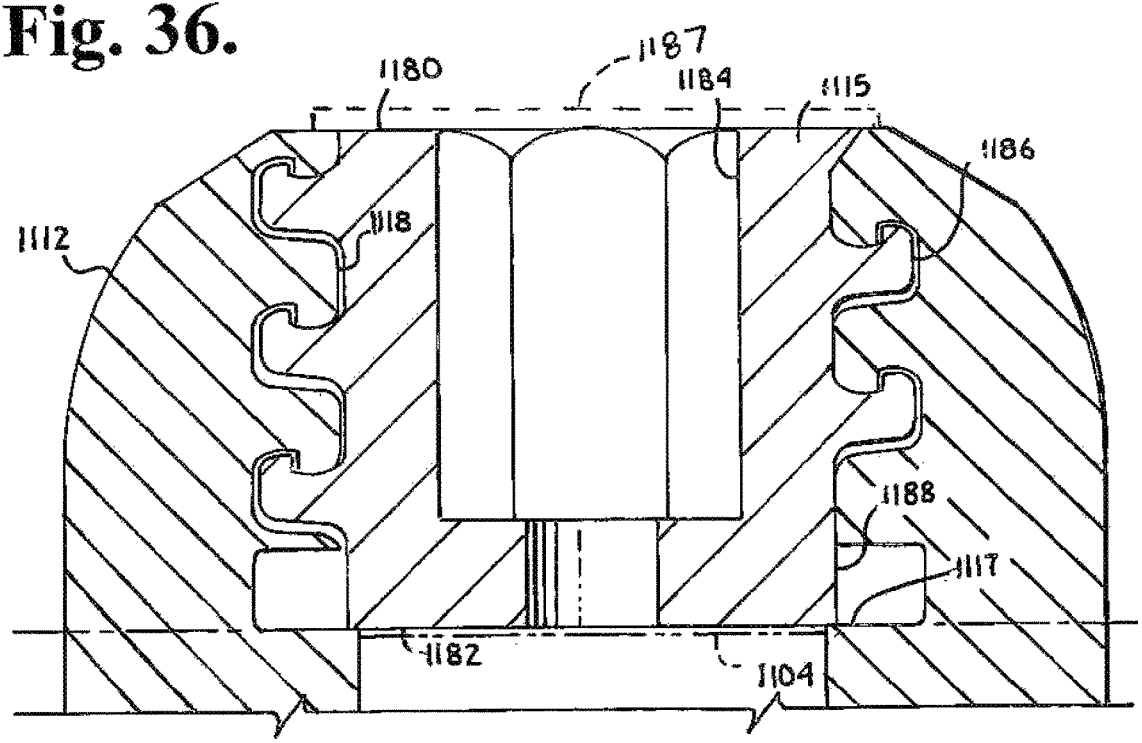
FIG. 36 is an enlarged and partial cross-sectional view taken along the line 36-36 of FIG. 35 and also showing the mated closure top in cross section, a portion of the cord in phantom and an alternative closure top possibility, such top having an upper cap or stop shown in phantom.
Figure 37:
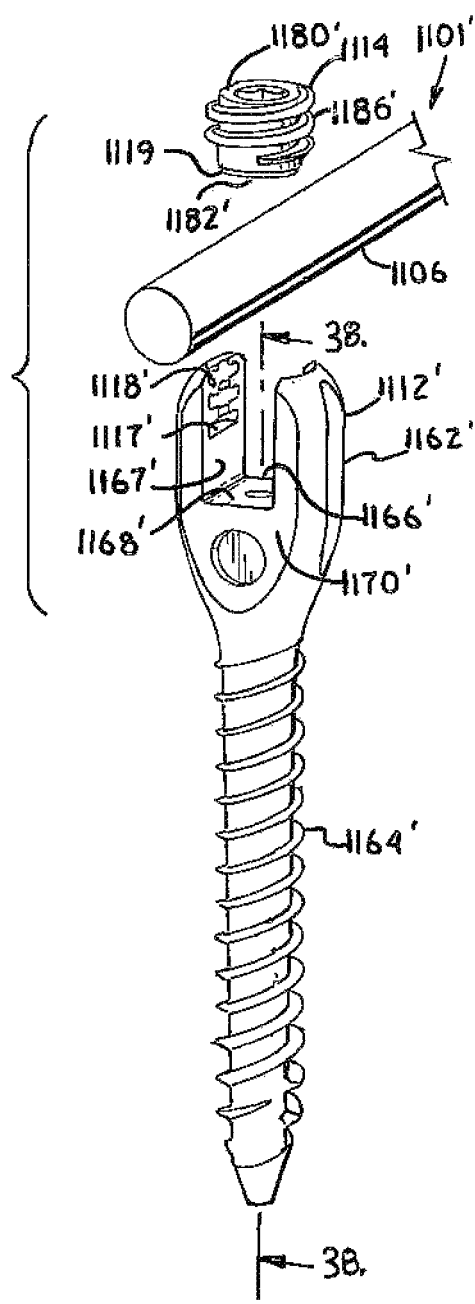
FIG. 37 is an exploded perspective view of the bone screw of FIG. 33 shown with a second locking closure top and a deformable rod.
Figure 38:
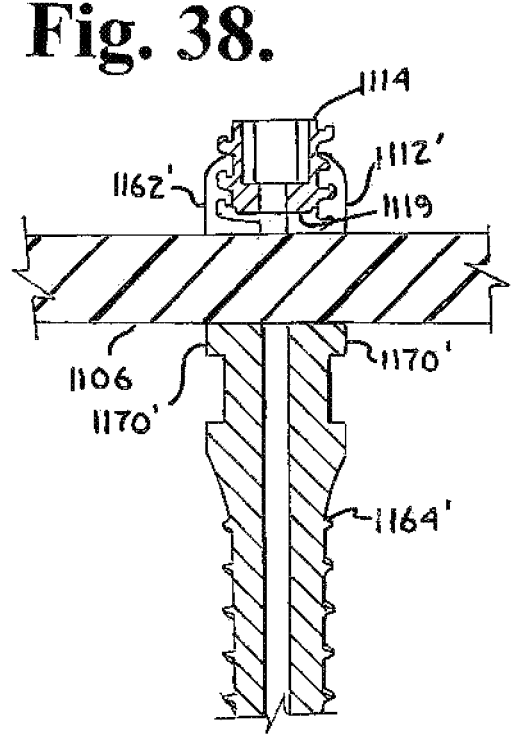
FIG. 38 is a partial cross-sectional view taken along the line 38-38 of FIG. 37 and showing the second locking closure top in an early stage of assembly.

With particular reference to FIGS. 35 and 36, the bone screw 1112 guide and advancement structure 1118 that receives and mates with the limited travel closure 1115 includes a run-out aperture or groove partially defined by a bottom or lower seating surface 1117 sized and shaped for frictional engagement with a portion of the closure 1115. As shown in FIG. 36, the closure 1115 minor diameter is slightly bigger than the run-out groove so the closure 1115 abuts against the surface 1117 when driven downward into the receiver. The seating surface 1117 terminates at the opposed planar surfaces 1167.

With further reference to FIG. 33, the bone screw receiver 1162 further includes opposed, substantially parallel outer side surfaces 1170. It is foreseen that according to the invention, other embodiments of the invention may include side surfaces that angle away or towards one another for lordosing or kyphosing controlling embodiments as previously described in applicant's application U.S. Ser. No. 11/328,481, the disclosure of which is incorporated by reference herein. It is also noted that the bone screw 1112 is identical or substantially similar to the bone screws described in described in detail in Applicant's U.S. patent application Ser. No. 12/584,980, the disclosure of which is incorporated by reference herein.

Specifically, the closure top 1115 is substantially cylindrical and includes a top surface 1180, a bottom surface 1182, a drive feature 1184 formed in the top surface 1180 and an outer guide and advancement structure 1186 sized and shaped to mate with the guide and advancement structure 1118 of the bone screw 1112. A cylindrical surface 1188 represents the minor diameter of a major portion of the closure 1115. The illustrated closure top 1115 is rotatable between the spaced arms forming the receiver 1162 of the screw 1112. The illustrated helically wound guide and advancement structure 1186 is in the form of a flange form that operably joins with respective guide and advancement structure 1118. A driving tool or tools (not shown) sized and shaped for engagement with the internal drive feature 1184 is used for both rotatable engagement and, if needed, disengagement of the closure 1115 from the screw 1112. The internal drive feature 1184 may take a variety of forms and may include, but is not limited to, a hex shape, TORX or other features or apertures, such as slotted, tri-wing, spanner, two or more apertures of various shapes, and the like.

With particular reference to FIG. 36, the closure top 1115 is sized and shaped to cooperate with the run-out surface 1117 to lock the closure 1115 on the bone screw 1112 independent of any pressure being placed by the closure 1115 on the cord 1104. Due to the size of the surface 1188, the bottom surface 1182 near the surface 1188 forms a radially extending shelf or abutment seat. When the closure 1115 is tightened by rotation into the screw 1112, the bottom 1182 abuts against the surface 1117, allowing the closure to be tightened in the screw receiver 1162 independent of whatever size cord 1104 or other core, such as the bar 1105 might be. Stated in another way, the closure 1115 is prohibited from entering the space between the planar surfaces 1167 that support the cord 1104 or other core therebetween. Thus, it is not possible for the closure 1115 to press upon the cord 1104, allowing such cord to slide between the closure top 1115 and the surfaces 1167 and 1168. Also shown in FIG. 36 is an alternative feature or cap portion 1187 (shown in phantom) that may be used in lieu of providing the surface 1117 of the bone screw 1112. In such an embodiment, the cap portion 1187 of the closure 1115 abuts against a top surface of the bone screw 1112 when the closure 1115 is fully mated and locked with the bone screw 1112 guide and advancement structure 1118, prohibiting the closure 1115 from being wound down into contact with a cord or other inner core member.

With reference to FIGS. 37-41, a bone screw 1112' is illustrated that is identical to the bone screw 1112, having a receiver 1162', a shank 1164', a rectangular channel 1166' formed by opposed planar surfaces 1167' and a bottom surface 1168', the same or substantially similar to the receiver 1162, shank 1164, channel 1166, opposed planar surfaces 1167 and bottom surface 1168 previously described herein with respect to the bone screw 1112. Further, the bone screw 1112' includes a lower seat 1117' of a guide and advancement structure 1118' and side surfaces 1170', the same or similar to the lower seat 1117, guide and advancement structure 1118 and side surfaces 1170 of the bone screw 1112. The bone screw 1112 is shown with the plastic, deformable rod 1106 and a locking closure top 1114 having a lower extension portion 1119 that is the same or similar to the closure top 1014 having the extended bottom portion 1019 previously described herein with respect to the assembly 1001.

The closure top 1114 is substantially cylindrical and includes a top surface 1180', a bottom surface 1182', a drive feature 1184' formed in the top surface 1180' and an outer guide and advancement structure 1186' sized and shaped to mate with the guide and advancement structure 1118' of the bone screw 1112'. A cylindrical surface 1188' represents the minor diameter of a major portion of the closure 1114. The illustrated closure top 1114 is rotatable between the spaced arms forming the receiver 1162' of the screw 1112'. The illustrated helically wound guide and advancement structure 1186' is in the form of a flange form that operably joins with respective guide and advancement structure 1118'. A driving tool or tools (not shown) sized and shaped for engagement with the internal drive feature 1184' is used for both rotatable engagement and, if needed, disengagement of the closure 115 from the screw 1112. The internal drive feature 1184 may take a variety of forms and may include, but is not limited to, a hex shape, TORX or other features or apertures, such as slotted, tri-wing, spanner, two or more apertures of various shapes, and the like.

Figure 39:
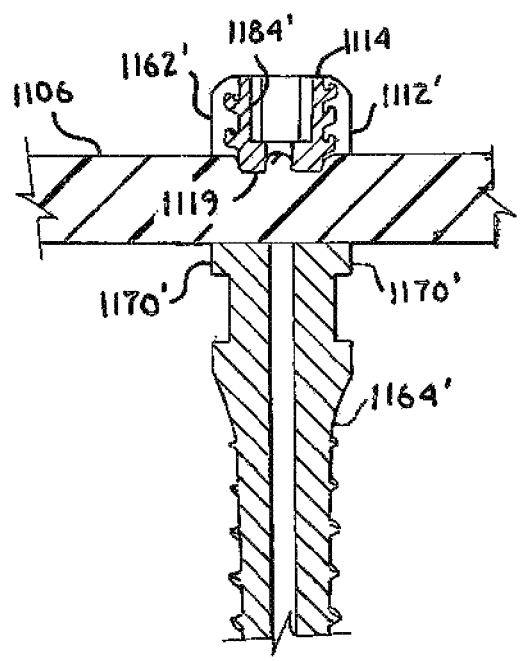
FIG. 39 is a partial cross-sectional view, similar to FIG. 38, showing the second closure top fully assembled within the bone screw and engaged with and compressing a deformable rod.
Figure 40:
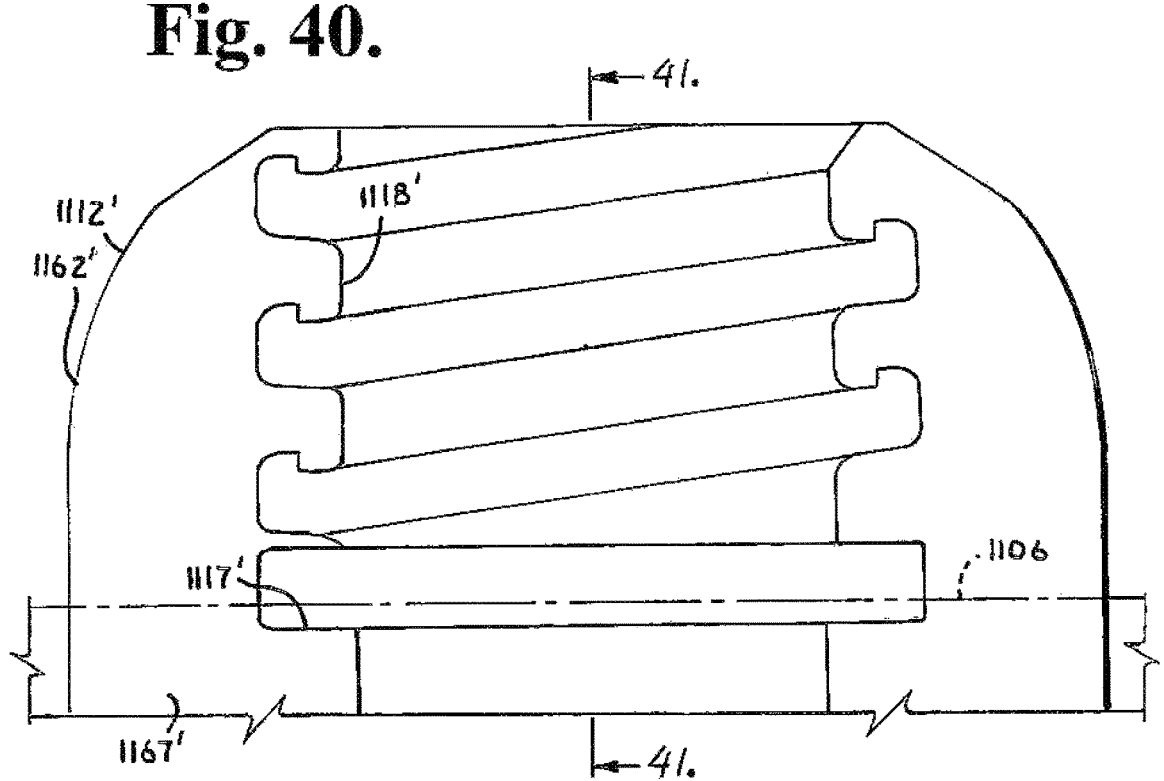
FIG. 40 is an enlarged and partial cross-sectional view of the bone screw of FIG. 37 taken along the line 38-38, with a portion of the deformable rod being shown in phantom.
Figure 41:
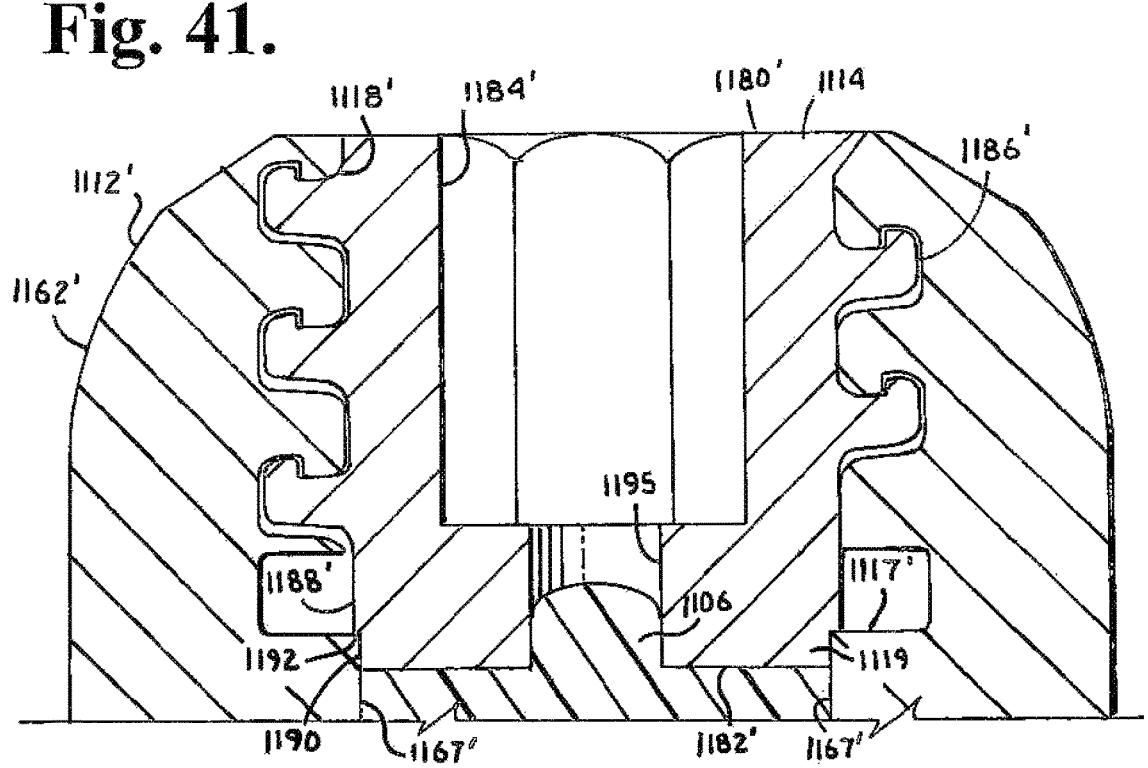
FIG. 41 is an enlarged and partial cross-sectional view, taken along the line 41-41 of FIG. 40, also showing the mated closure top and a portion of the deformable rod in cross-section.

With particular reference to FIG. 41, the closure top 1114 is sized and shaped to cooperate with the run-out surface of the guide and advancement structure 1118' to lock the closure 1114 on the bone screw 1112' independent of any pressure being placed by the closure 1114 on the deformable rod 1106. In the illustrated embodiment, the closure 1114 includes a second cylindrical surface 1190 located adjacent to and below the surface 1188' that defines the minor diameter of most of the closure 1114. The second cylindrical surface 1190 has a second diameter smaller than the minor diameter of the surface 1188'. The outer surface 1190 partially defines the extended portion 1119. The surface 1190 is located near the bottom surface 1182' of the closure 1114 that contacts and presses against the deformable rod 1106 or other longitudinal connecting member core located within the bone screw receiver 1162' during operation. As shown in FIGS. 39 and 41, the portion 1119 presses against and partially deforms the rod 1106. A radially extending shelf or abutment seat 1192 is formed between the cylindrical surface 1188' and the cylindrical surface 1190. When the closure 1114 is tightened by rotation into the screw 1112', the seat 1192 abuts against the surface 1117', allowing the closure to be tightened in the screw receiver 1162' independent of the rod 1106. The rod 1106 is pressed upon and held in place by the bottom surface 1182' of the screw, with some deformation of the rod 1106 being acceptable and even desirable. In the illustrated embodiment, some of the rod material is allowed to flow up into an inner bore 1195 of the closure 1114. However, because of the cooperation between the seat 1192 and the screw surface 1117', the rod 1106 is protected against over-deformation or crushing that might lead to instability and failure. Furthermore, if the rod 1106 exhibits creep or other deformation during operation, loosening or lessening of the contact engagement between the closure bottom surface 1182' and the rod 1106 will not result in loosening of the closure 1114 from the screw 1112'.

Figure 42:
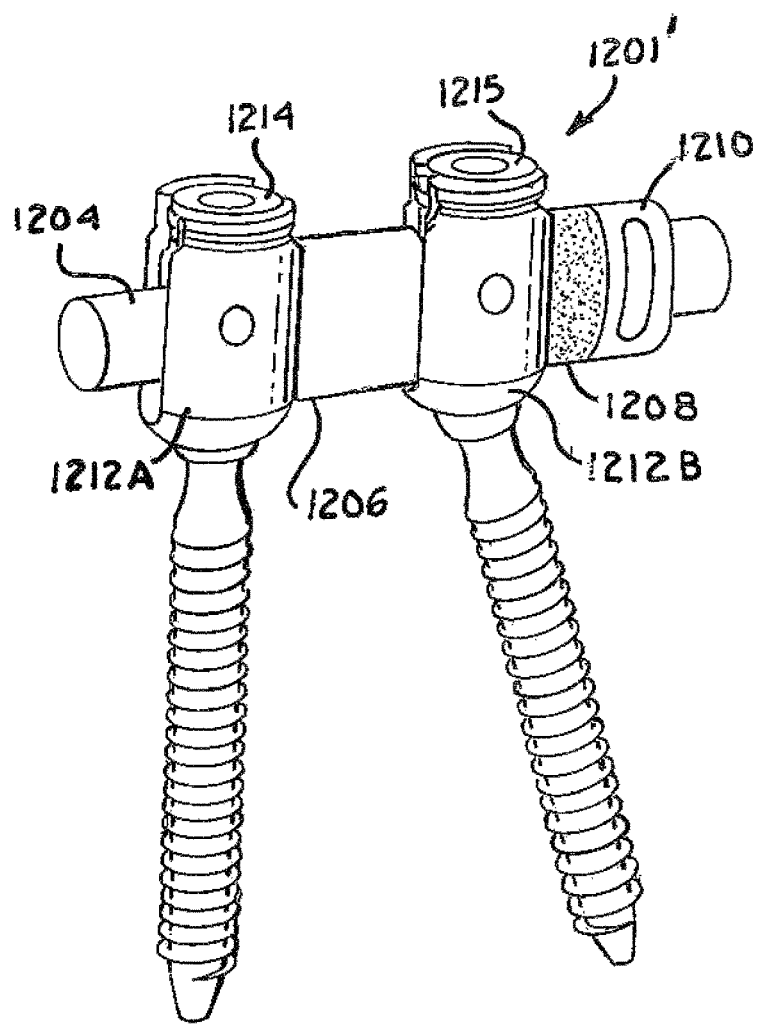
FIG. 42 is a perspective view of another alternative embodiment of a soft dynamic stabilization connector of the invention having an inner rod, an elastic bumper and a blocking structure, the connector shown with a pair of open polyaxial bone screws.
Figure 43:
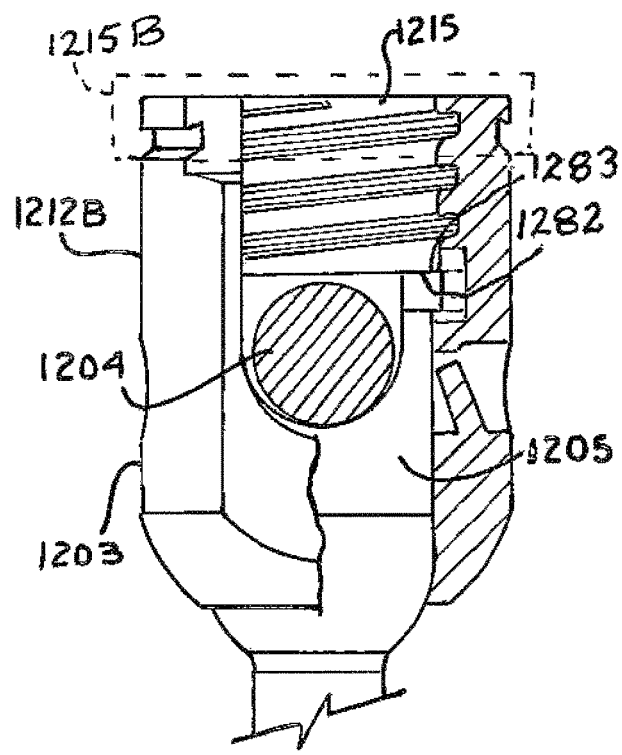
FIG. 43 is an enlarged and partial side elevational view of one of the bone screws of the embodiment of FIG. 42 with portions broken away to show the detail thereof and also showing an alternative cap portion in phantom.

With reference to FIGS. 42 and 43, an assembly 1201' according to the invention is illustrated that provides for dynamic stabilization similar to the assembly 1001 utilizing polyaxial bone screws. The illustrated assembly 1201 includes a solid, hard-surfaced rod 1204, a spacer 1206, an elastic bumper 1208, a crimping structure 1210 and a pair of polyaxial bone screws 1212A and 1212B. The bone screws 1212A and 1212B are identical or substantially similar to those described in Applicant's U.S. patent application Ser. No. 12/229,207, filed Aug. 20, 2008 entitled "Polyaxial Bone Anchor Assembly With One-Piece Closure, Pressure Insert and Plastic Elongate Member," (hereafter, the '207 application), the disclosure of which is incorporated by reference herein. A closure top 1214 fixes the rod 1204 in the bone screw 1212A and a closure top 1215 captures the rod 1204 in the bone screw 1212B, but a bottom surface 1282 thereof does not fix the rod 1204 with respect to the bone screw 1212B as illustrated in FIG. 43. (See, e.g., FIGS. 15-18 of the '207 application for illustrations of fixing of a rigid or deformable rod with a bone screw the same or similar to the screw 1212A). Each screw 1212A and 1212B further includes a receiver 1203 for slidingly pivotally receiving a bone screw shank upper portion, and a lower pressure insert 1205 having surfaces for engaging the shank upper portion and surfaces for closely receiving the rod 1204. With reference to FIG. 43, the closure top 1215 lower surface 1282 engages upper arm surfaces 1283 of the pressure insert 1205 to capture the rod 1204 and lock the polyaxial mechanism of the bone screw 1212B. Thus, the captured rod 1204 is in sliding engagement with the screw 1212B. The spacer 1206, elastic bumper 1208 and the blocker crimping structure 1210 are the same or similar in form and function to the spacer 1006, bumper 1008 and crimping structure 1010 previously described herein with respect to the assembly 1001, with the crimping structure 1210 directly engaging the rod 1204. In alternative embodiments, a cord or deformable rod may be utilized in lieu of the illustrated rigid rod 1204. The pressure insert 1205 may also be configured to receive a square or rectangular bar. Also, FIG. 43 illustrates an alternative cap closure 1215B (shown in phantom) having an upper outer portion that extends about a top portion of the receiver 1212B and cooperates with a lip thereof to lock the closure to the receiver 1212B at a desired position with the lower surface 1282 of the closure pressing down on the pressure insert 1205 to lock the polyaxial mechanism without pressing of the rod, cord or other longitudinal connecting member captured between the insert and the closure.

With reference to FIGS. 44-49, the reference numeral 2001 generally designates another non-fusion, soft or dynamic longitudinal stabilization connector assembly of the invention. The illustrated assembly 2001 includes the following components: an elongate bendable and soft, flexible core in the form of a cord 2004; at least one cannulated spacer 2006; an elastic bumper 2008; and a fixing structure or blocking member, such as a blocker 2010 with cooperating set screw 2011. The assembly 2001 is shown with three open monoaxial bone screws, generally 2012, the assembly 2001 extending substantially linearly along a central axis AA. The assembly 2001 is also shown with two different closure tops for cooperating with the bone screws 2012: a cord gripping closure top 2014 and a non-gripping closure top 2015. The bone screws 2012 and closure tops 2014 and 2015 are also shown in greater detail in FIG. 60. Furthermore, the blocker 2010 and cooperating set screw 2011 are shown in greater detail in FIGS. 55-58. The spacer 2006 is also shown in FIG. 59. It is noted that the spacers 2006 and bumper 2008 are shown as being made from a transparent plastic. However, in some embodiments of the invention, spacers and bumpers may also be opaque.

The cord 2004 is identical or substantially similar in form, function and materials to the cord 1004 previously described herein and the cord or cord bundles previously described herein with respect to the assembly 1. Similarly, the spacers 2006 are the same or similar in form, function and materials to the spacers 1006 and the spacers 214 and 314 previously described herein with the exception that, as best shown in FIG. 59, the spacer 2006, although tubular, is also shaped to provide more spacer material below the cord 2004. Spacers of the invention could also be cylindrical or have other shapes. The bumper 2008 is a cylindrical tube and is the same or similar in form, function and materials as the bumper 1008 previously described herein.

The blocker 2010 and set screw 2011 combination functions similarly to the crimping blocking member 1010, for example, previously described herein and may also be made from the same hard materials. Rather thank crimping the blocker 1010 to attach the blocker to the cord, the blocker 2010 is attached to the cord 2004 by action of the set screw 2011 being rotated and moved downwardly against the cord 2004 until the cord 2004 is fixed against the blocker 2010. With reference to FIGS. 55-58, the blocker 2010 advantageously includes opposed grooves 2020 that allow for ease in holding the blocker 2010 during assembly and also during surgery. The blocker 2010 advantageously has a more narrow profile as measured along the length of the cord 2004 than the crimping blocker 1010 previously described herein as the set screw 2011 rather than blocker material is required for pressing against the cord 2004. The blocker 2010, bumper 2008, bone screws 2012 and spacers 2006 advantageously include planar end surfaces that are also space saving and provide easy compatibility, changeability and substitution between the assembly components.

The open bone screws 2012 are the same or similar to the bone screws 1012 previously described herein. Each bone screw 2012 is compatible with the gripping closure top 2014 that includes a lower projection 2030 for pressing against the cord 2004 and also compatible with the slipping closure top 2015 that does not have a projection 2030, but otherwise locks in the screw 2012 in a manner previously described herein with respect to the screws 1012 and the closure top 1015. The bone screw 2012 also cooperates with a closure top 2016 that further includes a point or a point and rim for cooperating with a hard rod as shown, for example, in FIG. 50.

Figure 44:
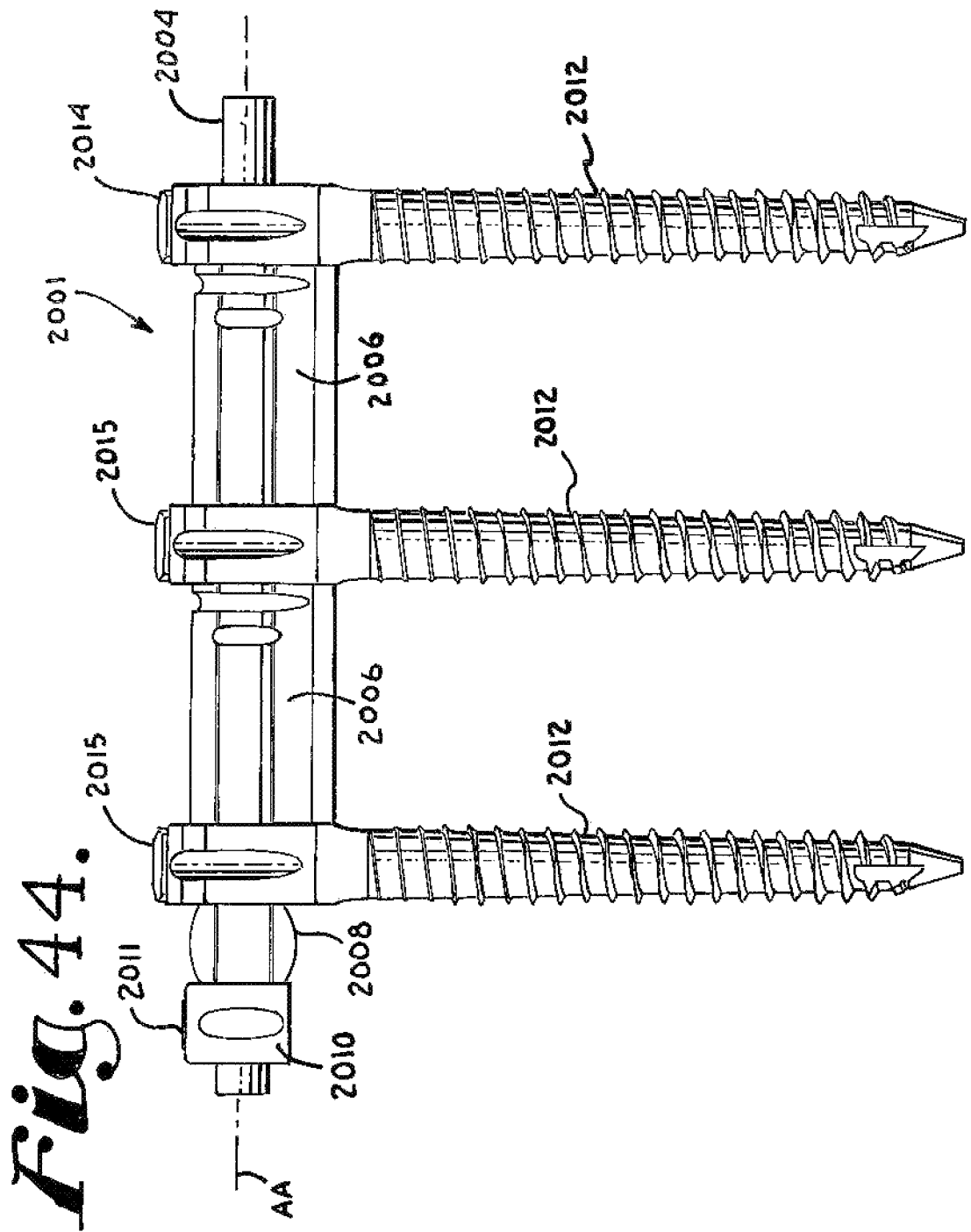
FIG. 44 is a front elevational view of another soft dynamic stabilization connector of the invention having an inner cord, an elastic bumper and a blocking structure, two spacers and shown with three open monoaxial screws and cooperating closure tops.
Figure 45:
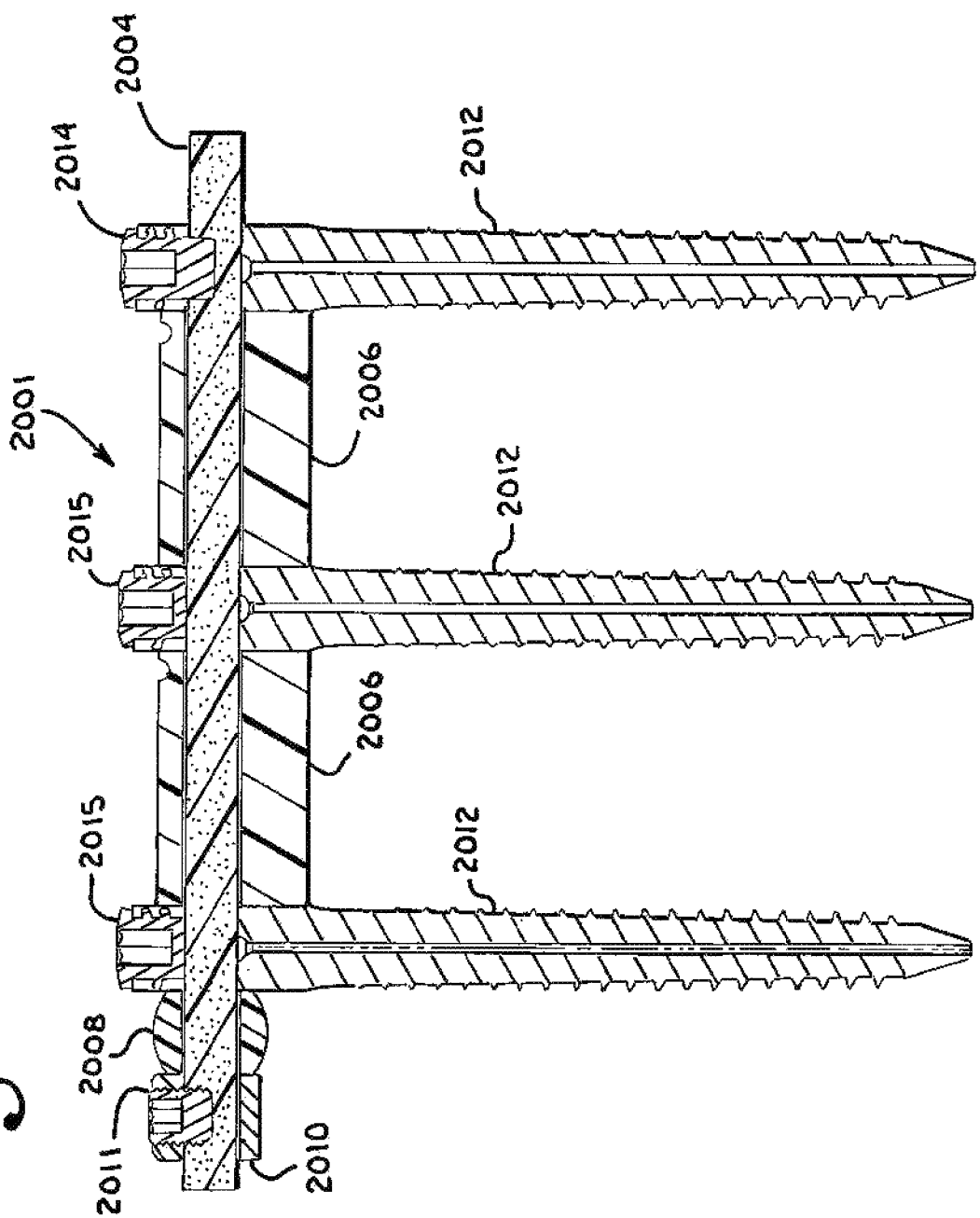
FIG. 45 is another front elevational view of the connector of FIG. 44 with portions broken away to show the detail thereof.
Figure 46:
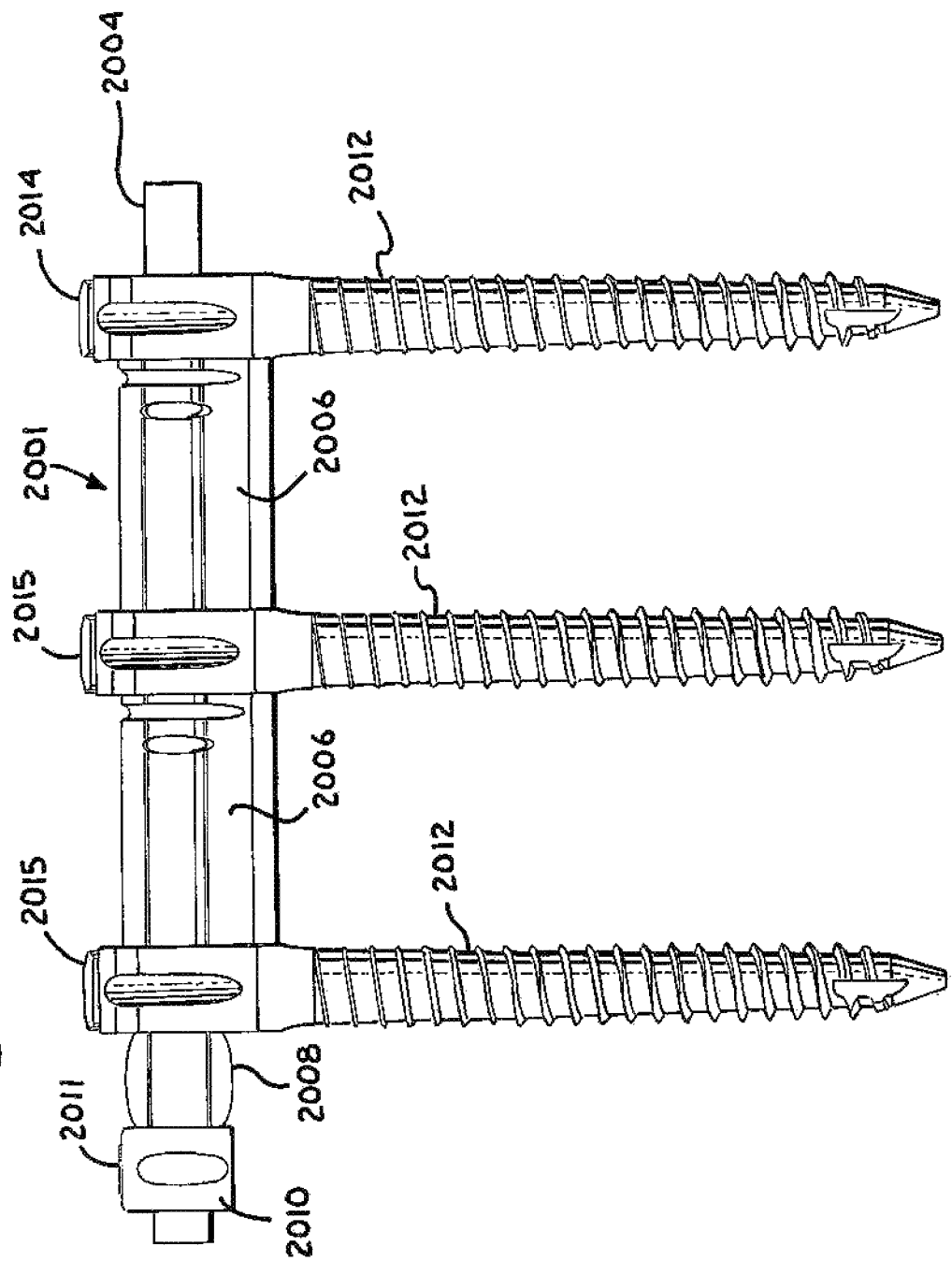
FIG. 46 is another front elevational view of the connector of FIG. 44 shown in a compressed state.
Figure 47:
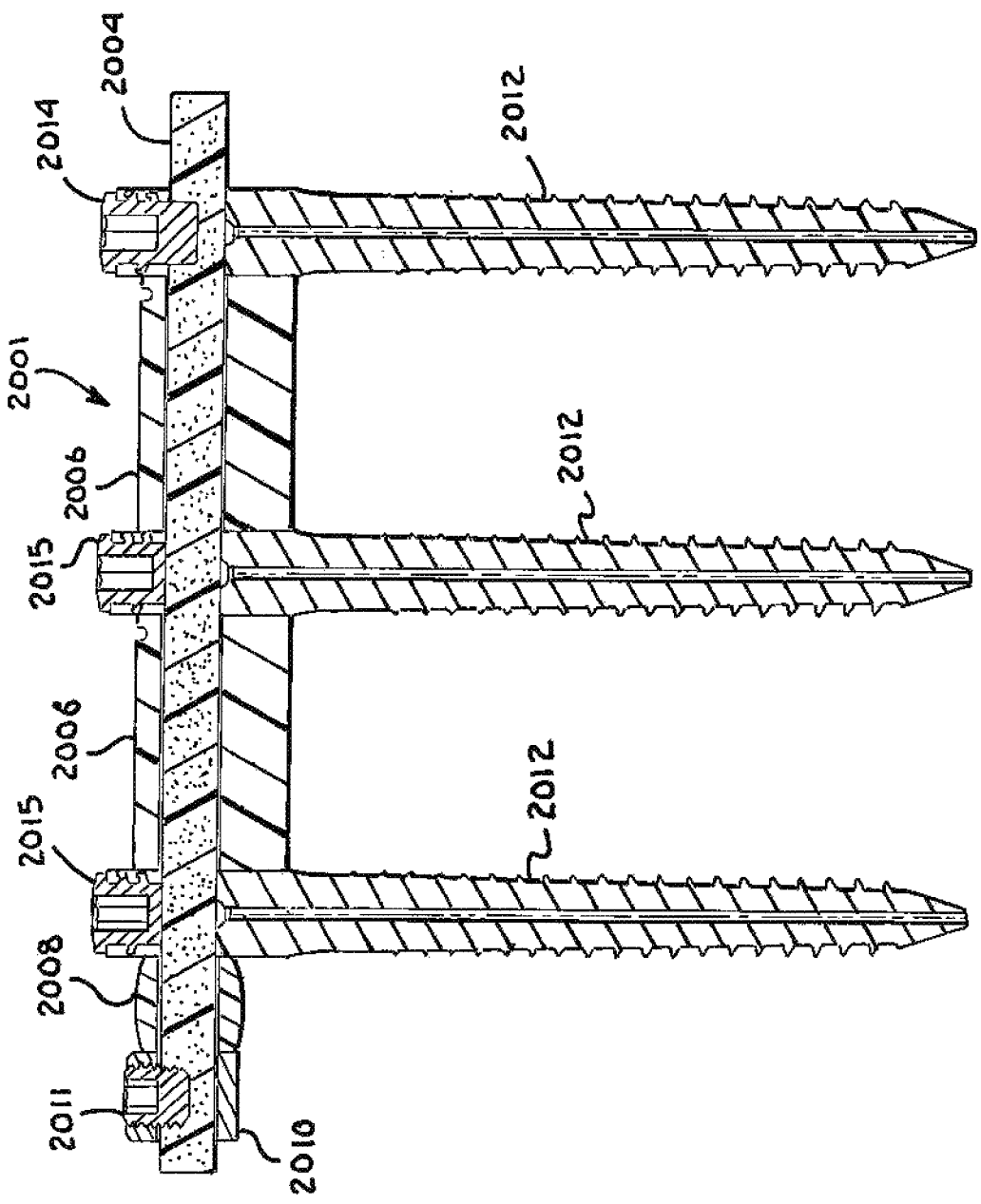
FIG. 47 is a front elevational view of the connector of FIG. 46 with portions broken away to show the detail thereof.
Figure 48:
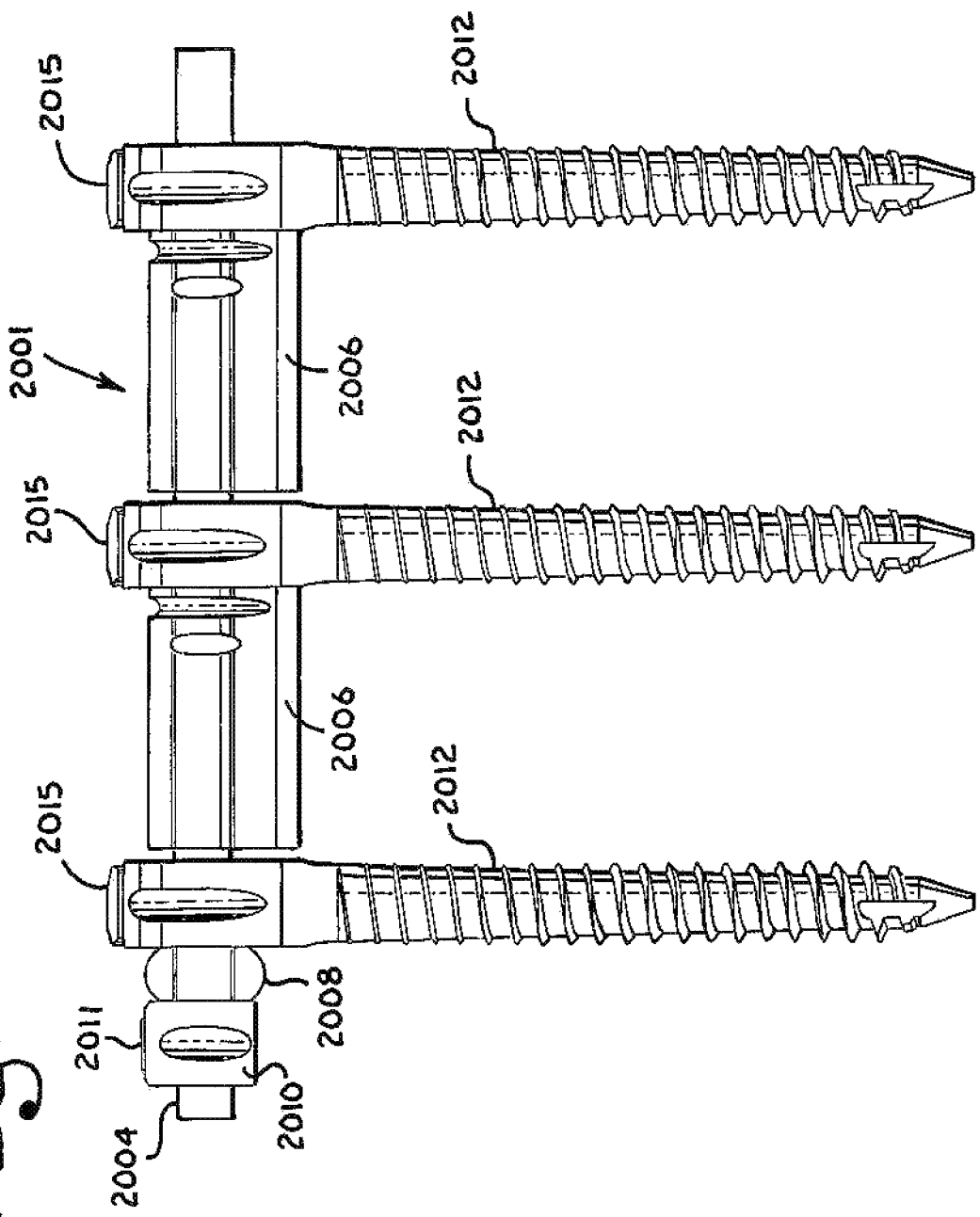
FIG. 48 is another front elevational view of the connector of FIG. 44 shown in a distracted state.
Figure 49:
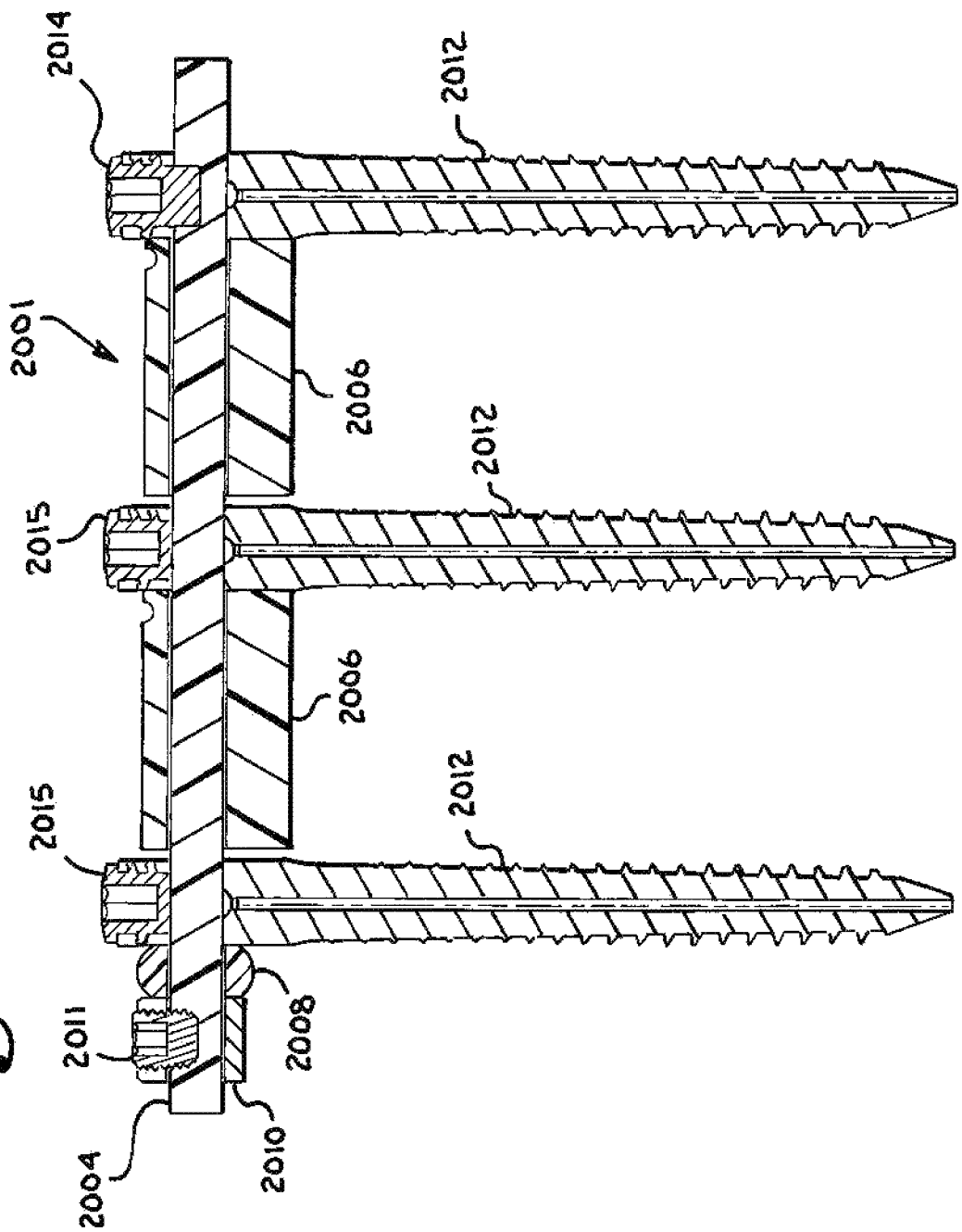
FIG. 49 is a front elevational view of the connector of FIG. 48 with portions broken away to show the detail thereof.

With further reference to FIGS. 44 and 45, the assembly 2001 is shown in a nominal state, as, for example, the assembly would be in after the cord 2004 is tensioned (in some embodiments, after the cord 2004 has had some extension after creep and wherein the cord 2004 may have been re-tensioned and recaptured at either the bumper 2010 or the closure top 2014). As shown, tensioning of the cord 2004 also results in some compression placed on the bumper 2008 as well as the two spacers 2006. As best shown in FIG. 45, the cord 2004 is in tension between the blocker 2010 and the end screw 2012 that has the closure top 2014 pressing against the cord 2004. The cord 2004 is free to slide with respect to the other two screws 2012 that are mated with the slip closure tops 2015. With reference to FIGS. 46 and 47, the assembly 2001 is shown responding to a compressive force on vertebrae (not shown) attached to the three bone screws 2012. In such instance, the elastic bumper 2008 is allowed to expand to a near neutral state, with the cord 2004 and spacers 2006 moving in response to such force. With reference to FIGS. 48 and 49, the assembly 2001 is shown responding to a distractive force, pushing the bumper 2008 into further compression and resulting in only a slight gap between the spacers 2006 and the bone screws 2012.

Figure 50:
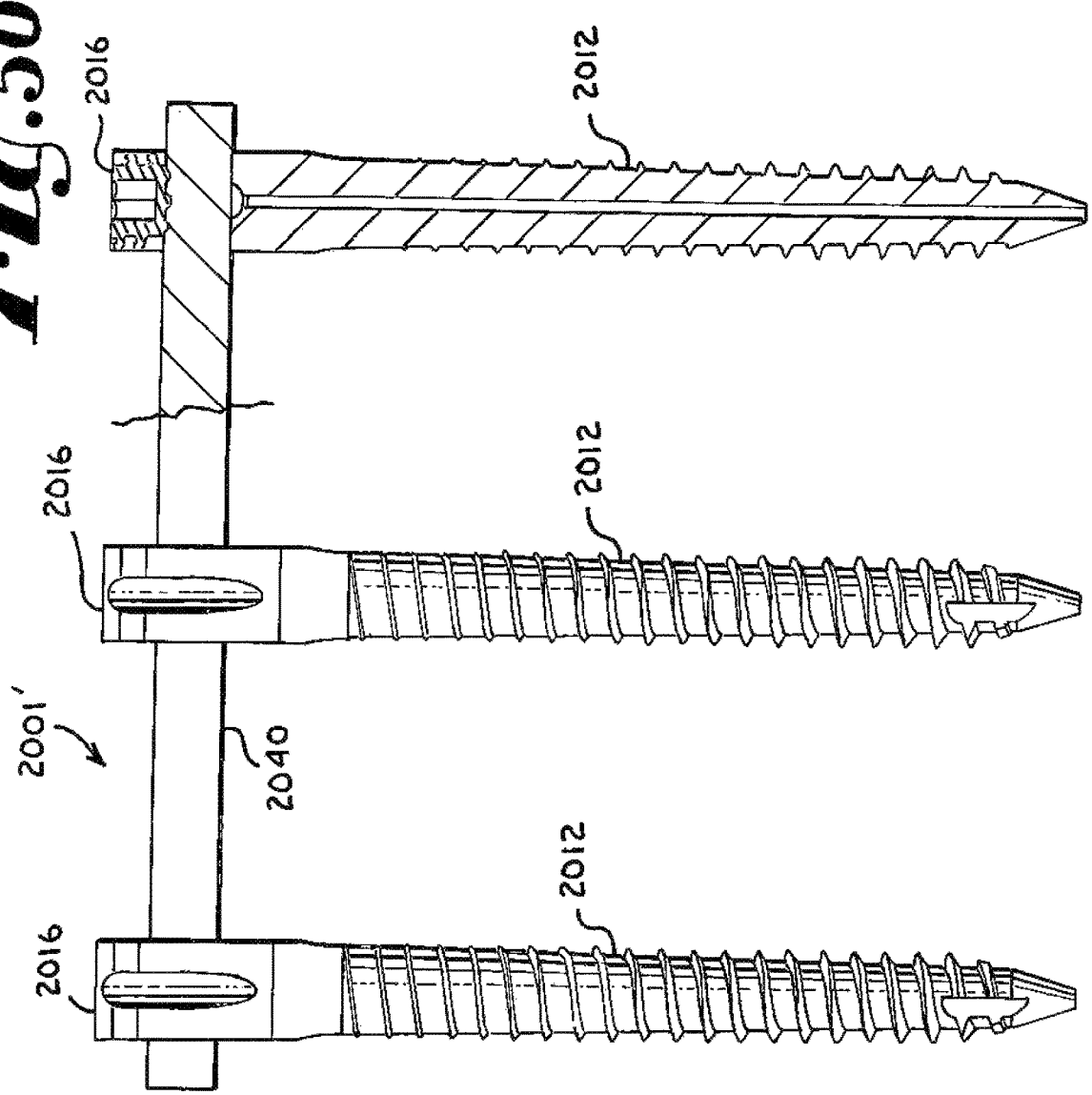
FIG. 50 is a front elevational view with portions broken away to show the detail thereof of a replacement assembly wherein the soft cord, blocker, bumper and spacers of the connector of FIG. 44 have been removed and replaced with a hard rod.

With reference to FIG. 50, the assembly 2001 has been modified to create the assembly 2001' wherein the cord 2004, the spacers 2006, the bumper 2009 and the blocker 2010 are replaced with a hard rod 2040 and each of the bone screws 2012 are attached to the rod 2040 with the closure top 2016.

Figure 51:
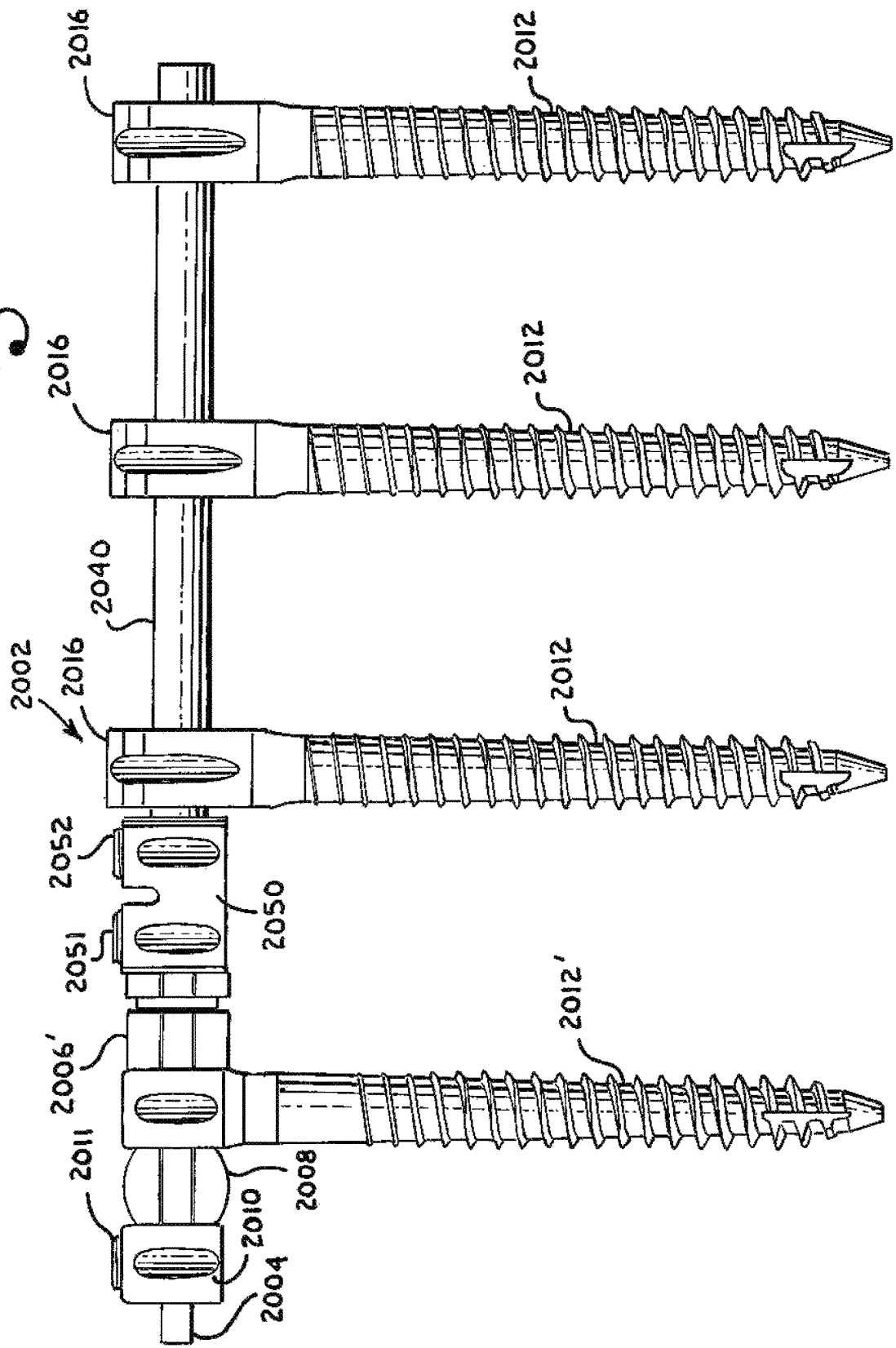
FIG. 51 is a front elevational view of another soft dynamic stabilization connector of the invention having an inner cord, an elastic bumper and a blocking structure, a spacer, a rod/cord connector, a rod and shown with four open monoaxial screws and cooperating closure tops.
Figure 52:
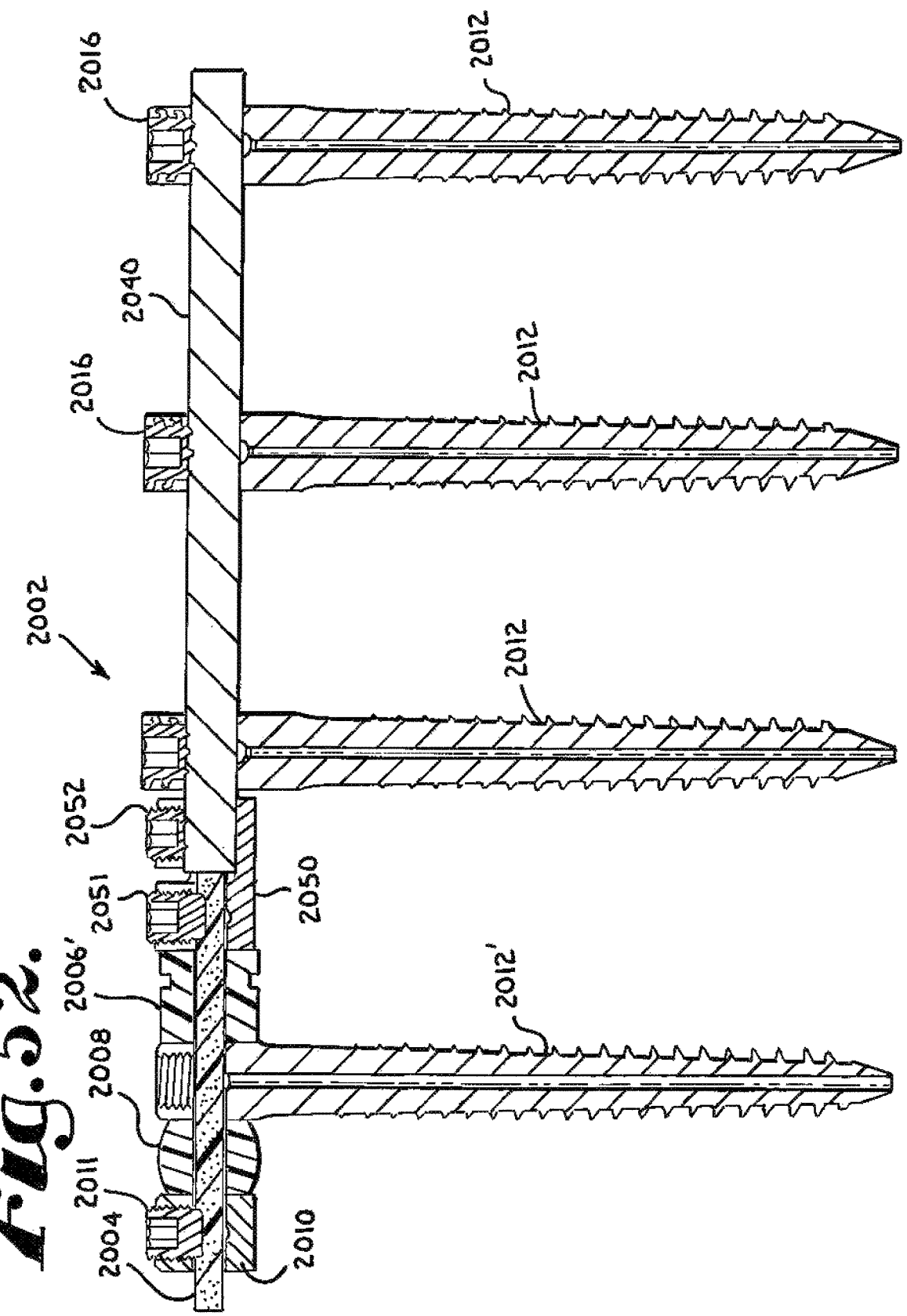
FIG. 52 is another front elevational view of the connector of FIG. 51 with portions broken away to show the detail thereof.

FIGS. 51 and 52 illustrated an alternative assembly 2002 wherein a cord 2004 is attached to a hard rod 2040 using a rod/cord connector or blocker 2050 that cooperates with a set screw 2051 and a set screw 2052. The rod/cord blocker 2050 is sized and shaped like a double-wide blocker 2010 with a first bore for slidingly receiving the cord 2004 at an end thereof communicating with a larger bore for receiving the rod 2040 at an end thereof. Running perpendicular to the cord and rod through bore are two threaded apertures allowing for connection and capture of the cord 2004 by rotation and downward movement of the longer set screw 2041 and connection and capture of the hard rod 2040 by downward rotation of the shorter set screw 2052 (see also FIG. 61). It is noted that the set screw 2051 and the set screw 2011 may be identical. The cord is tensioned between the set screw 2051 and rod/cord connector 2050 and the blocker 2010 with set screw 2011. A bumper 2008 is located next to the blocker and is also adjacent to a closed bone screw 2012' that will be described in greater detail below. On the other side of the screw 2012' is a small on-axis tubular spacer 2006' (that will also be described in more detail below) that in turn is adjacent to the rod/cord blocker 2050. The hard rod 2040 is then shown attached to three bone screws 2012, each cooperating with a closure top 2016. Thus, the cord 2004 is in slidable cooperating with the bone screw 2012', providing some soft stabilization in an otherwise more hard or rigid assembly 2002.

Figure 53:
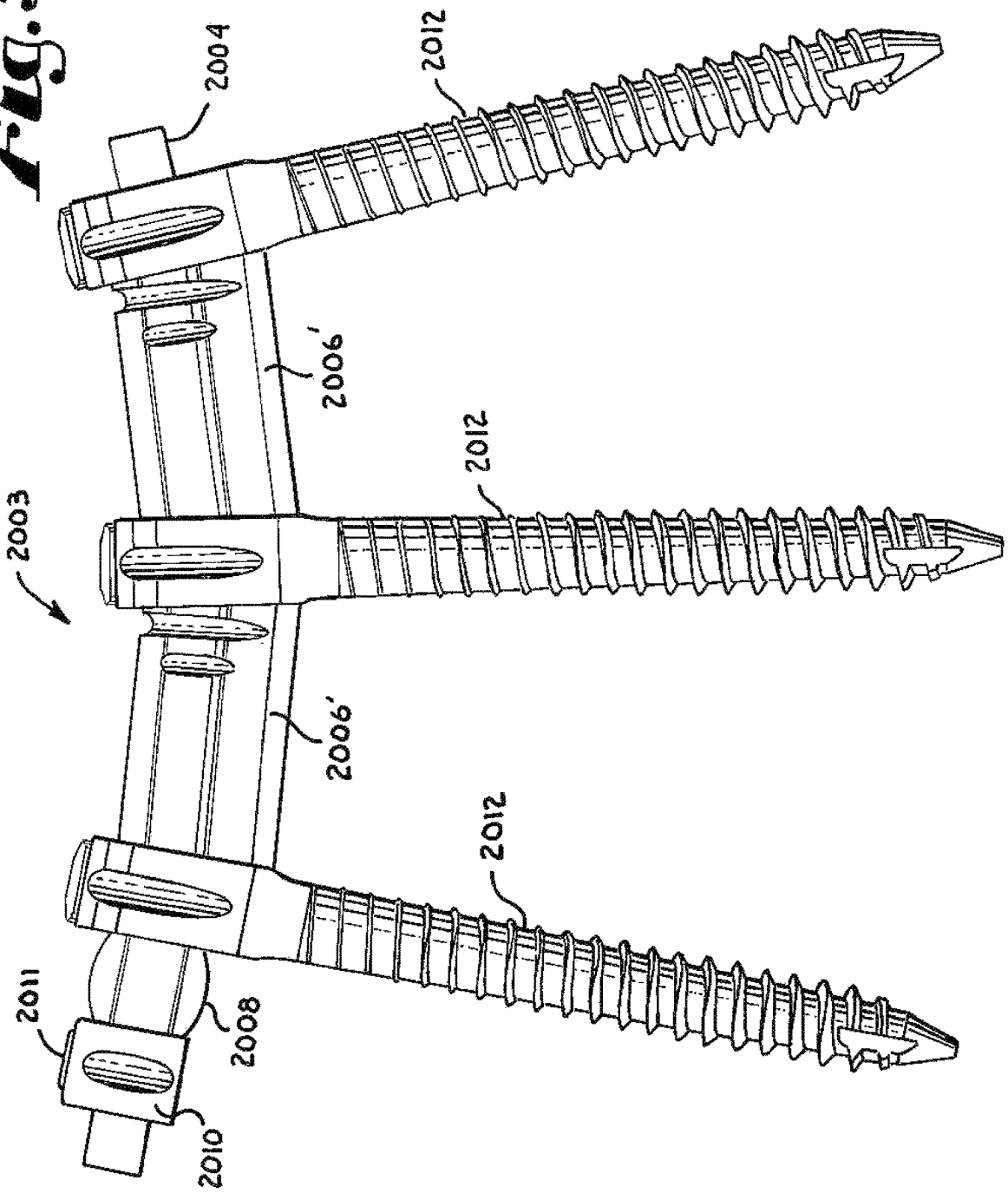
FIG. 53 is a front elevational view of another soft dynamic stabilization connector of the invention having an inner cord, an elastic bumper and a blocking structure, two lordotic spacers, and shown with three open monoaxial screws and cooperating closure tops.
Figure 54:
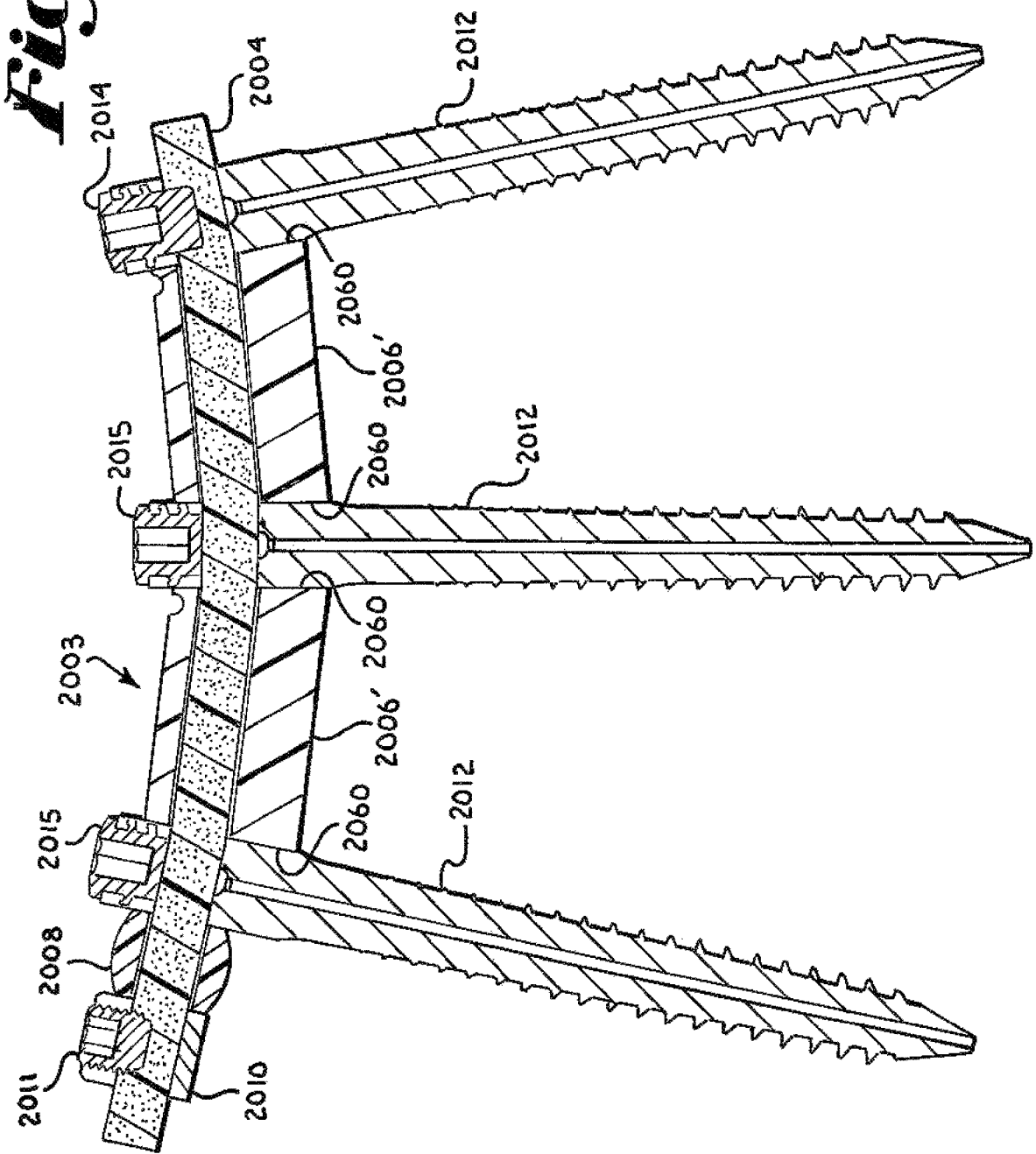
FIG. 54 is another front elevational view of the connector of FIG. 53 with portions broken away to show the detail thereof.
Figure 55:
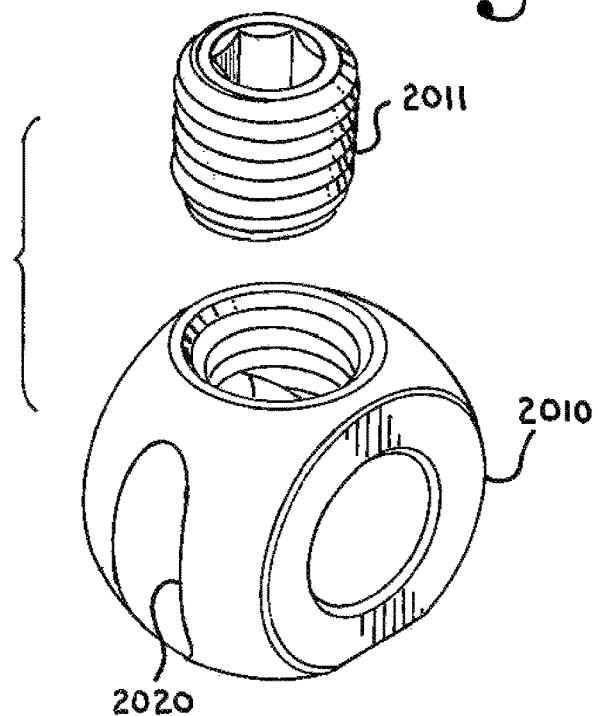
FIG. 55 is an enlarged, exploded and perspective view of the blocker and cooperating set screw shown in FIG. 44.
Figure 56:
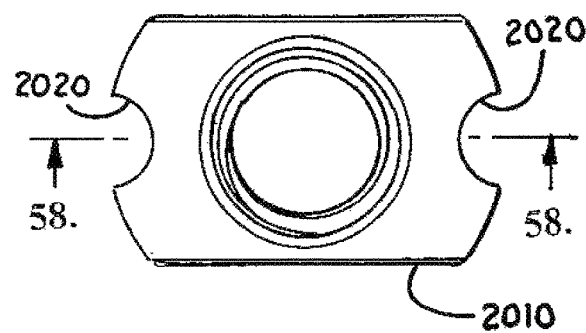
FIG. 56 is a top plan view of the blocker of FIG. 55.
Figure 58:
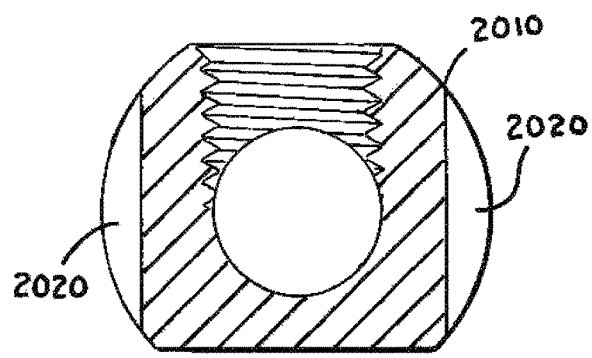
FIG. 58 is a cross-sectional view taken along the line 58-58 of FIG. 56.
Figure 57:
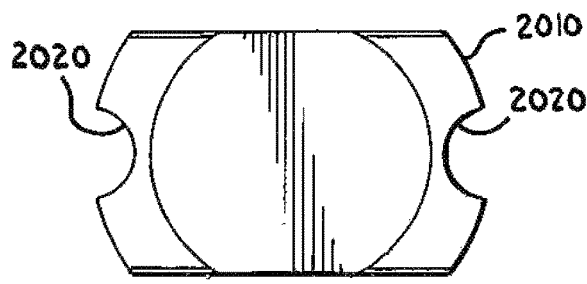
FIG. 57 is a bottom plan view of the blocker of FIG. 55.

With reference to FIGS. 53 and 54, a soft stabilization connector 2003 is illustrated that includes the cord 2004, bumper 2008, blocker 2010 and bone screws 2012 previously described herein. In this embodiment the spacers 2006 of the assembly 2001 are replaced with lordotic spacers 2006'. The spacers 2006' are identical to the spacers 2006 with the exception of planar end surfaces 2060 that are formed or cut at an angle, resulting in a desired lordotic arrangement of the assembly components.

With reference to FIGS. 62-63, another soft stabilization connector 3001 is shown. The assembly 3001 is identical to the assembly 2001 with the exception that tubular on-axis spacers 2006' replace the off-axis spacers 2006 and closed screws 2012' replace the open screws 2012. The closed screw 2012' with cooperating set screw 2011' is shown in greater detail in FIGS. 69-71. The closed screws 2012' differ from the open screws 2012 in that the closed screws 2012' cooperate with the smaller set screw 2011' (that may be identical to the blocker set screw 2011), requiring threading of the cord 2004 through a through bore 3010 of the screw 2012' as opposed to the open channel provided by the open screw 2012 that receives the cord 2004 through an upper opening of the channel. The closed screws 2012' however, advantageously allow for complete capture of the cord 2004 as well as slidable movement between the cord 2004 and the screw 2012'. Thus, no set screw is needed when a slidable relationship between the cord 2004 and the screw 2012' is desired.

The assembly 3001 shown in FIGS. 62 (A-C) and 63 (A-C) includes a pre-tensioned cord 2004 fixed between the blocker 2010 and the bone screw 2012' that is cooperating with the set screw 2011'. The cord is slidable with respect to the other two bone screws 2012' that are not cooperating with any set screws 2011'. Pre-tensioning of the cord 2004 also results in some compression of the bumper 2008 and the two spacers 2006'. Also, with further reference to FIGS. 62 (A-C- and 63 (A-C), three states or positions of the assembly components are shown in these figures. In the state or position identified by the letter X in FIGS. 62A and 63A, a distracted state or position of the vertebrae (not shown) is demonstrated wherein the bumper 2008 is fully compressed while the spacers 2006' are axially extended to a near neutral or nominal state. In the state or position identified by the letter Y in FIGS. 62B and 63B, the vertebrae (not shown) are compressed together, resulting in the bumper 2008 expanding to a near neutral state with the spacers 2006' being fully compressed. The state or position identified by the letter Z in FIGS. 62C and 63C is a nominal or neutral position in which the bumper 2008 and the spacers 2006' are slightly compressed and are holding the cord 2004 in a steady-state tension.

Figure 65:
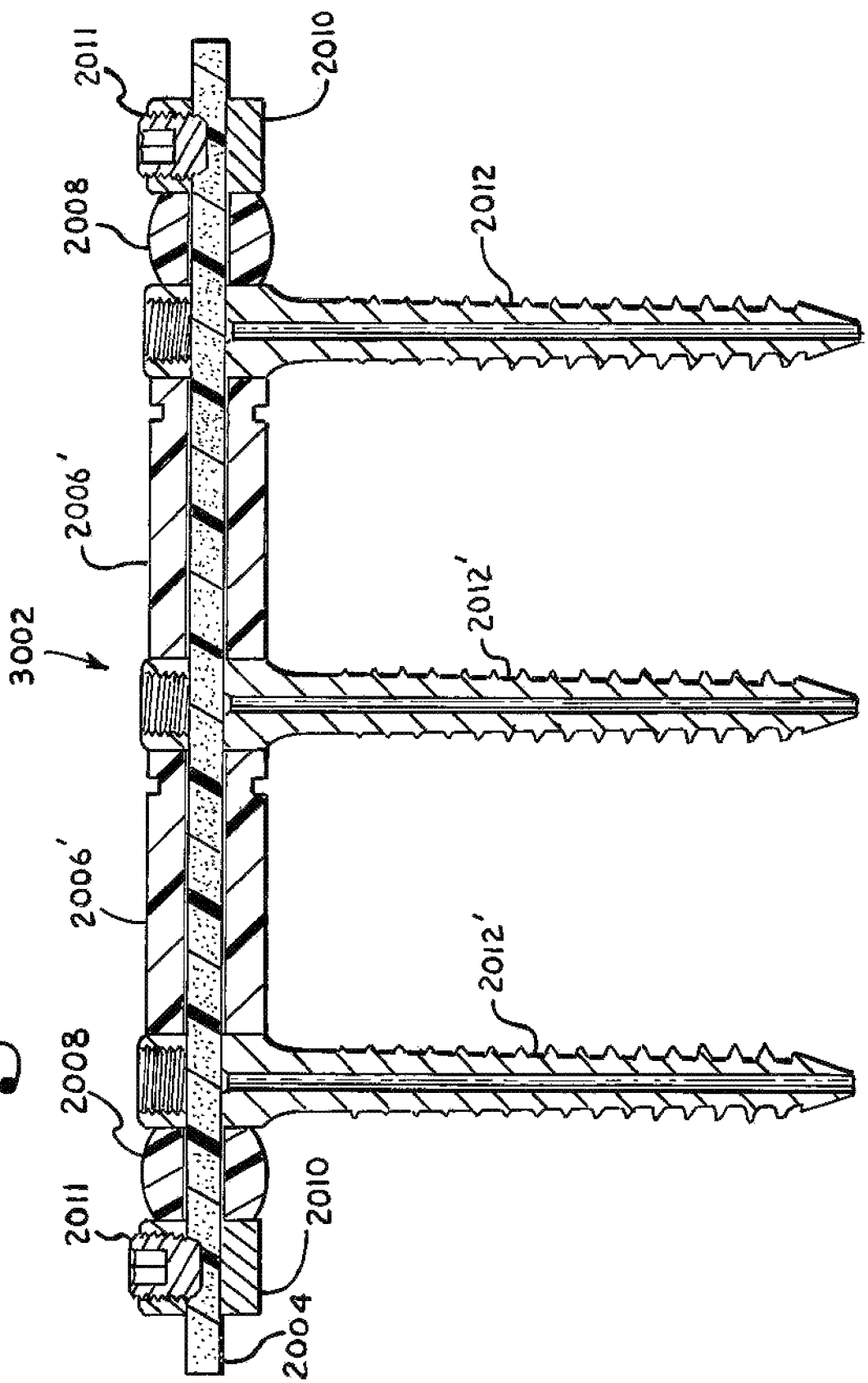
FIG. 65 is a partial front elevational view with portions broken away of the connector of FIG. 64.

With reference to FIGS. 64 and 65, another embodiment of a soft stabilization connector 3002 is shown that includes a blocker 2010/set screw 2011 combination on either side thereof, the blockers holding a pre-tensioned cord 2004 in tension along and with respect to three closed bone screws 2012', none of which are cooperating with a set screw. Thus, the cord 2004 is in slidable relationship with each of the three bone screws 2012'. Located adjacent each blocker 2010 is a bumper 2008 and on-axis spacers 2006' are located between each of the screws 2012'. It is noted that one or both of the bumpers 2008 may be omitted in certain embodiments.

Figure 66:
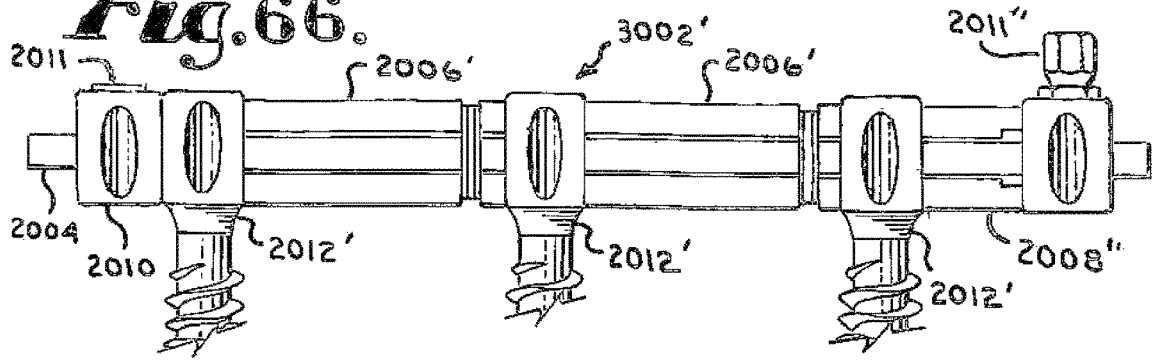
FIG. 66 is a partial front elevational view of another soft dynamic stabilization connector of the invention having an inner cord, one elastic bumper, two blocking structures, one having a break-off head, two spacers and shown with three closed monoaxial screws with no set screws.
Figure 67:
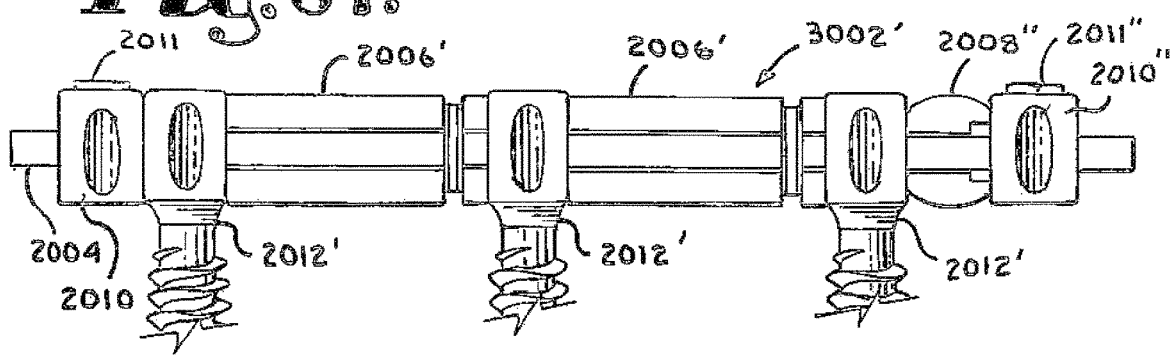
FIG. 67 is another partial front elevational view of the connector of FIG. 66, showing the spacer compressed and the blocking structure break-off head removed.
Figure 68:
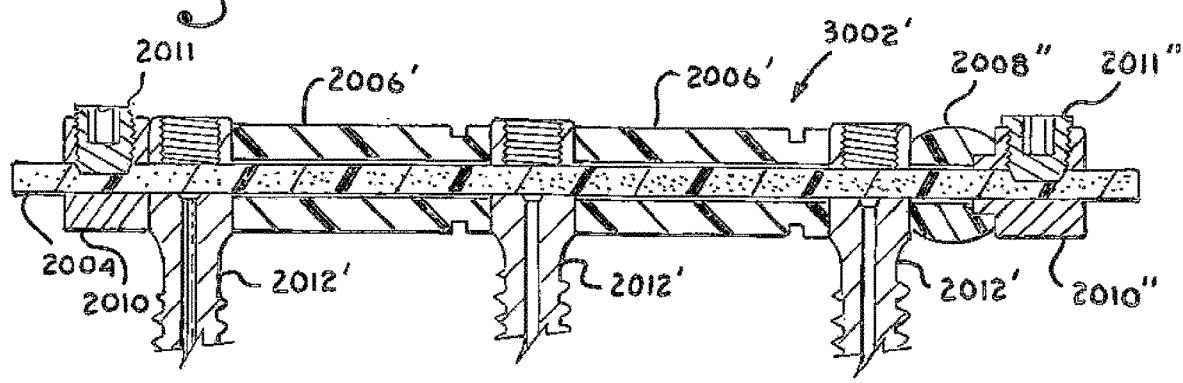
FIG. 68 is a partial front elevational view with portions broken away of the connector of FIG. 67.

With reference to FIGS. 66-68, another embodiment of a soft stabilization connector 3002' is shown that includes a blocker 2010/set screw 2011 combination on one side thereof and a blocker 2010"/break-off head set screw 2011" on the other side thereof, the blockers holding a pre-tensioned cord 2004 in tension along and with respect to three closed bone screws 2012', none of which are cooperating with a set screw. Thus, the cord 2004 is in slidable relationship with each of the three bone screws 2012'. Located adjacent the blocker 2010" is a bumper 2008" and on-axis spacers 2006' are located between each of the screws 2012'. It is noted that there is no bumper between the blocker 2010 and the bone screw 2012'. However, in some embodiments, such a bumper may be included. The bumper 2008" overlaps an inner portion of the blocker 2010" as best shown in FIG. 68. FIG. 66 illustrates the connector 3002' prior to tensioning the cord 2004. FIGS. 67 and 68 illustrate the connector 3002' in a tensioned state with the bumper 2008" in compression and the blocker break-off head already removed, exposing an inner drive of the set screw 2011" if loosening and removal or repositioning and further tightening of the cord 2004 is required.

It is to be understood that while certain forms of the present invention have been illustrated and described herein, it is not to be limited to the specific forms or arrangement of parts described and shown.

What is claimed and desired to be secured by Letters Patent is as follows:

1. A longitudinal connecting member assembly configured to support a portion of a spine of a patient, the assembly comprising:
    a first and a second bone anchor, each configured to be locked by a closure;
    a tensionable cord extending between the first and second bone anchors and being in slidable relation with respect to the second bone anchor when the first and second bone anchors are locked by the respective closures;
    an end structure configured to be releasably secured to the tensionable cord at least while a portion of the tensionable cord is under tension, the portion of the tensionable cord being located between the first bone anchor and the end structure and between the second bone anchor and the end structure, the end structure having a non-threaded through-bore configured to receive the tensionable cord along a longitudinal axis extending through the end structure and having a cylindrical outer surface coaxial with the longitudinal axis and a planar outer end surface orthogonal to the cylindrical outer surface; and
    a spacer slidably positioned on the tensionable cord between the end structure and the second bone anchor, the spacer configured to be compressed and space the planar outer end surface from the second bone anchor when the tensionable cord is tensioned and secured to the end structure,
    wherein the tensionable cord is retensionable after the end structure has been secured to the tensionable cord and the first and second bone anchors have been locked,
    wherein the end structure includes a planar inner end surface orthogonal to the cylindrical outer surface and is configured to directly engage the spacer, and
    wherein the planar inner end surface is spaced inwardly apart from the planar outer end surface.

2. The assembly of claim 1, wherein the end structure is positioned entirely outside of the first and second bone anchors.

3. The assembly of claim 1, wherein the end structure has a portion configured to be moved toward the tensionable cord, thereby fixing the tensionable cord within the through-bore.

4. The assembly of claim 1, further comprising a second spacer located between the first and second bone anchors, the second spacer having a through-bore that slidingly receives the tensionable cord.

5. The assembly of claim 4, wherein the second spacer is compressible.

6. The assembly of claim 1, wherein at least one of the first and second bone anchors is a polyaxial screw, the polyaxial screw having a shank and a receiver for holding the tensionable cord, the receiver being pivotable with respect to the shank, and the closure is configured to capture the tensionable cord within the receiver.

7. The assembly of claim 1, wherein the end structure includes an elongate opening on the cylindrical outer surface, the elongate opening having planar side surfaces parallel to the planar outer end surface.

8. The assembly of claim 1, wherein the end structure is configured to secure the tensionable cord with at least one indentation within the through-bore.

9. The assembly of claim 1, wherein the end structure is configured to secure the tensionable cord by deforming the tensionable cord against an inner surface of the through-bore.

10. The assembly of claim 1, wherein the end structure is configured to secure the tensionable cord without penetrating the tensionable cord.

11. An end blocker subassembly configured to be used with a longitudinal connecting member assembly, the assembly including first and second bone anchors supporting a portion of a spine of a patient, each bone anchor including a receiver configured to hold a tensionable cord and a closure configured to capture the tensionable cord in the receiver, the tensionable cord extending between the first and second bone anchors and being in slidable relation with respect to the second bone anchor when the first and second bone anchors are locked by the respective closures, the end blocker subassembly comprising:
- a rigid end structure configured to be releasably secured to the tensionable cord at least while a portion of the tensionable cord is under tension, the portion of the tensionable cord being located between the first bone anchor and the rigid end structure and between the second bone anchor and the rigid end structure, the rigid end structure having a non-threaded through-bore configured to receive the tensionable cord along a longitudinal axis extending through the rigid end structure and having a cylindrical outer surface coaxial with the longitudinal axis and a planar outer end surface orthogonal to the cylindrical outer surface; and
- a compressible spacer slidably positioned on the tensionable cord between the rigid end structure and the second bone anchor, the compressible spacer configured to be compressed and separate the planar outer end surface from the second bone anchor when the tensionable cord is tensioned and secured to the rigid end structure,
- wherein the tensionable cord is retensionable with a cord pulling tool after the end structure has been secured to the tensionable cord and the first and second bone anchors are in a locked position by their respective closures,
- wherein the rigid end structure includes a planar inner end surface orthogonal to the cylindrical outer surface and is configured to directly engage the compressible spacer, and
- wherein the planar inner end surface is spaced inwardly apart from the planar outer end surface.

12. The subassembly of claim 11, wherein the rigid end structure is positioned entirely outside of the first and second bone anchors.

13. The subassembly of claim 11, wherein the rigid end structure has at least one portion that is configured to be moved toward the tensionable cord, thereby fixing the tensionable cord within the through-bore.

14. The subassembly of claim 11, further comprising a second spacer located between the first and second bone anchors, the second spacer having a through-bore that slidingly receives the tensionable cord.

15. The subassembly of claim 14, wherein the second spacer is compressible.

16. The subassembly of claim 11, wherein at least one of the first and second bone anchors is a polyaxial screw.

17. The subassembly of claim 11, wherein the rigid end structure includes an elongate opening on the cylindrical outer surface, the elongate opening having planar side surfaces parallel to the planar outer end surface.

18. The subassembly of claim 11, wherein the rigid end structure is configured to secure the tensionable cord with at least one indentation within the through-bore.

19. The subassembly of claim 11, wherein the rigid end structure is configured to secure the tensionable cord by deforming the tensionable cord against an inner surface of the through-bore.

20. The subassembly of claim 11, wherein the rigid end structure is configured to secure the tensionable cord without penetrating the tensionable cord.

* * * * *